(12) United States Patent
Bissantz et al.

(10) Patent No.: US 8,022,099 B2
(45) Date of Patent: *Sep. 20, 2011

(54) N-BENZYL PYRROLIDINE DERIVATIVES

(75) Inventors: Caterina Bissantz, Village-Neuf (FR); Philippe Jablonski, Steinbrunn-le-Haut (FR); Henner Knust, Rheinfelden (DE); Matthias Nettekoven, Grenzach-Wyhlen (DE); Hasane Ratni, Habsheim (FR); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/604,429

(22) Filed: Oct. 23, 2009

(65) Prior Publication Data

US 2010/0113424 A1 May 6, 2010

(30) Foreign Application Priority Data

Nov. 3, 2008 (EP) .................................. 08168213

(51) Int. Cl.
*A61K 31/40* (2006.01)
*C07D 207/14* (2006.01)

(52) U.S. Cl. ........................ 514/426; 548/557

(58) Field of Classification Search .................. 548/557
See application file for complete search history.

(56) References Cited

FOREIGN PATENT DOCUMENTS

| EP | 1553084 | 7/2005 |
|---|---|---|
| WO | 2008/128891 | 10/2008 |
| WO | 2009/072643 | 6/2009 |

OTHER PUBLICATIONS

Tooney et al., Neurosci. Lett. 2000, vol. 283 pp. 185-188.
Giardina, et al., Exp. Opin. Ther. Patents, 2000, vol. 10, pp. 939-960.
Jung et al., Neurosci. 1996, vol. 74, pp. 403-414.
Marco et al., Neuropeptides, 1998 vol. 32 pp. 481-488.
Kamali, F., Curr. Opinion in Investigational Drugs, 2001, pp. 950-956.

*Primary Examiner* — Shawquia Young
(74) *Attorney, Agent, or Firm* — George W. Johnston; Patricia S. Rocha-Tramaloni; Kimberly J. Prior

(57) ABSTRACT

The present invention relates to a compound of formula I

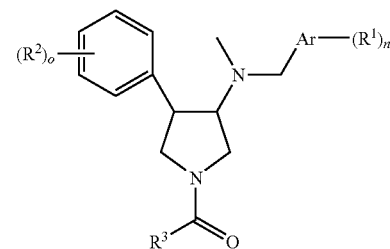

wherein
Ar, $R^1$, $R^2$, $R^3$, n, and o are as defined herein
or to a pharmaceutically active salt, a racemic mixture, an enantiomer, an optical isomer or a tautomeric form thereof. The present compounds are high potential NK-3 receptor antagonists for the treatment of depression, pain, psychosis, Parkinson's disease, schizophrenia, anxiety and attention deficit hyperactivity disorder (ADHD).

53 Claims, No Drawings

N-BENZYL PYRROLIDINE DERIVATIVES

PRIORITY TO RELATED APPLICATION(S)

This application claims the benefit of European Patent Application No. 08168213.0, filed Nov. 3, 2008, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS, and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorder, due to a wide array of symptoms, has hampered those efforts. There are no specific focal characteristics for the diagnosis of schizophrenia, and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001,2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.).

SUMMARY OF THE INVENTION

The present invention provides a compounds of formula I

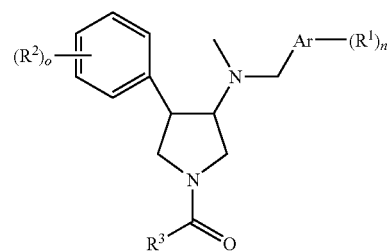

wherein
Ar is aryl;
R$^1$ is hydrogen, halogen, lower alkyl, lower alkoxy, lower alkyl substituted by halogen, lower alkoxy substituted by halogen, cyano, amino, mono or di-lower alkyl amino, C(O)-lower alkyl, aryl or heteroaryl;
R$^2$ is hydrogen or halogen;
R$^3$ is —(CH$_2$)$_p$-heterocyclyl optionally substituted by one or two substituents R$^4$; or is lower alkyl,
  lower alkoxy,
  —(CH$_2$)$_p$—O-lower alkyl,
  —(CH$_2$)$_p$—CN,
  —O—(CH$_2$)$_p$—CN,
  —(CH$_2$)$_p$-heteroaryl,
  —(CH$_2$)$_p$—C(O)-heteroaryl,
  —O—(CH$_2$)$_p$-heterocyclyl,
  —(CH$_2$)$_p$-aryl optionally substituted by lower alkoxy or halogen,
  —(CH$_2$)$_p$—O-aryl optionally substituted by lower alkyl,
  —(CH$_2$)$_p$—NR'-heterocyclyl optionally substituted by lower alkyl,
  —CH$_2$)$_p$—NR'R",
  —CH$_2$)$_p$—NR'—CH$_2$)$_{p'}$—NR'R",
  —CH$_2$)$_p$—NR'—CH$_2$)$_{p'}$CN,
  —CH$_2$)$_p$—C(O)—NR'R" or
  —O—(CH$_2$)$_p$—NR'R";
R$^4$ is hydroxy, lower alkyl, —(CH$_2$)$_p$—OH, —(CH$_2$)$_p$—NR'R", —NR'—C(O)-lower alkyl, —(CH$_2$)$_p$—CN, —S(O)$_2$-lower alkyl, —NR'—S(O)$_2$-lower alkyl, —S(O)$_2$—NR'R", —C(O)-lower alkyl, —C(O)-lower cycloalkyl wherein the cycloalkyl is optionally substituted by lower alkyl, —C(O)—NR'R", heterocyclyl which is optionally substituted by =O, heteroaryl which is optionally substituted by alkoxy or cyano, aryl which is optionally substituted by alkoxy or cyano, or is 2-oxa-5-aza-bicyclo[2.2.1]hept-5-yl;

R' and R" are each independently hydrogen, lower alkyl or —(CH$_2$)$_p$—OH;

n is 1 or 2; wherein when n is 2, each R$^1$ is the same or different;

o is 1 or 2; wherein when o is 2, each R$^2$ is the same or different;

p and p' are each independently 0, 1, 2, 3 or 4;

or a pharmaceutically active salt, a racemic mixture, an enantiomer, an optical isomer or a tautomeric form thereof.

The invention includes all stereoisomeric forms, including individual diastereoisomers and enantiomers of the compound of formula (I) as well as racemic and non-racemic mixtures thereof.

The present invention also provides pharmaceutical compositions containing a therapeutically effective amount of a compound of formula I or a pharmaceutically acceptable salt thereof and a pharmaceutically acceptable carrier. The invention further provides methods for the production of the compounds and compositions of the invention.

The present compounds are high potential NK-3 receptor antagonists for the treatment of depression, pain, bipolar disorders, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes a lower alkyl group as defined above, wherein at least one hydrogen atom is replaced by halogen, for example —CF$_3$, —CHF$_2$, —CH$_2$F, —CH$_2$CF$_3$, —CH$_2$CH$_2$CF$_3$, —CH$_2$CF$_2$CF$_3$ and the like. Preferred lower alkyl substituted by halogen groups are groups having 1-4 carbon atoms.

The term "halogen" denotes chlorine, iodine, fluorine and bromine.

The term "lower alkoxy" denotes a group —O—R wherein R is a lower alkyl group as defined above, preferably methoxy.

The term "lower alkoxy substituted by halogen" denotes a lower alkoxy group as defined above, wherein at least one hydrogen atom on the lower alkyl group is replaced by halogen, for example —OCF$_3$, —OCHF$_2$, —OCH$_2$F, —OCH$_2$CF$_3$, —OCH$_2$CH$_2$CF$_3$, —OCH$_2$CF$_2$CF$_3$ and the like.

The term "lower cycloalkyl" denotes a saturated carbon ring containing from 3-7 carbon atoms, for example, cyclopropyl, cyclobutyl, cyclopentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazin-2-yl, pyrazol-1-yl, 2,4-dihydro-pyrazol-3-one, pyridinyl, isoxazolyl, benzo[1,3]dioxol, pyridyl, pyrimidin-4-yl, pyrimidin-5-yl, benzotriazol-5-yl, benzoimidazol-5-yl, [1,3,4]-oxadiazol-2-yl, [1,2,4]triazol-1-yl, [1,6]naphthyridin-2-yl, imidazo[4,5-b]pyridine-6-yl, tetrazolyl, thiazolyl, thiadiazolyl, thienyl, furyl, imidazol-1-yl, or benzofuranyl. Preferred heteroaryl group is pyridine-2, 3 or 4-yl.

The term heterocyclyl denotes a five or six membered nonaromatic ring system, containing one or two heteroatoms selected from N, S and O, for example the following groups: morpholinyl, [1,4]diazepam-1-yl, piperazinyl, pyrrolidin-1-yl, piperidin-1-yl, piperidin-4-yl or 1,1-dioxo-$\lambda^6$-thiomorpholinyl.

"Pharmaceutically acceptable," such as pharmaceutically acceptable carrier, excipient, etc., means pharmacologically acceptable and substantially non-toxic to the subject to which the particular compound is administered.

The terms "pharmaceutically acceptable acid addition salts" and "pharmaceutically active salts" are synonymous and embrace salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Compounds of formula I, wherein Ar is phenyl, are preferred.

Compounds of formula I, wherein R$^3$ is optionally substituted —(CH$_2$)$_p$-heterocyclyl.

Preferred compounds of formula I are those, wherein R$^3$ is unsubstituted —(CH$_2$)$_p$-heterocyclyl, for example the following compounds:

1-{(3SR,4RS)-3-(3,4-dichloro-phenyl)-4-[(3-fluoro-4-trifluoromethyl-benzyl)-methyl-amino]-pyrrolidin-1-yl}-5-morpholin-4-yl-pentan-1-one;

1-{(3SR,4RS)-3-(3,4-dichloro-phenyl)-4-[methyl-(4-trifluoromethyl-benzyl)-amino]-pyrrolidin-1-yl}-5-morpholin-4-yl-pentan-1-one;

1-{(3SR,4RS)-3-(3,4-dichloro-phenyl)-4-[(3-fluoro-4-trifluoromethyl-benzyl)-methyl-amino]-pyrrolidin-1-yl}-5-piperazin-1-yl-pentan-1-one;

1-{(3SR,4RS)-3-(3,4-dichloro-phenyl)-4-[(3-fluoro-4-trifluoromethyl-benzyl)-methyl-amino]-pyrrolidin-1-yl}-5-pyrrolidin-1-yl-pentan-1-one;

1-{(3SR,4RS)-3-(3-chloro-phenyl)-4-[(3-fluoro-4-trifluoromethyl-benzyl)-methyl-amino]-pyrrolidin-1-yl}-5-morpholin-4-yl-pentan-1-one;

1-{(3S,4R)-3-(3,4-dichloro-phenyl)-4-[(3-fluoro-4-trifluoromethyl-benzyl)-methyl-amino]-pyrrolidin-1-yl}-3-morpholin-4-yl-propan-1-one;

1-{(3SR,4RS)-3-(3,4-dichloro-phenyl)-4-[(3-fluoro-4-trifluoromethyl-benzyl)-methyl-amino]-pyrrolidin-1-yl}-2-morpholin-4-yl-ethanone;

1-{(3SR,4RS)-3-(3,4-dichloro-phenyl)-4-[(3-fluoro-4-trifluoromethyl-benzyl)-methyl-amino]-pyrrolidin-1-yl}-2-piperazin-1-yl-ethanone; and 1-{(3S,4R)-3-(3,4-dichloro-phenyl)-4-[(3-fluoro-4-trifluoromethyl-benzyl)-methyl-amino]-pyrrolidin-1-yl}-2-(1,1-dioxo-$\lambda^6$-thiomorpholin-4-yl)-ethanone.

Preferred compounds of formula I are further those, wherein $R^3$ is —$(CH_2)_p$-heterocyclyl, substituted by one or two substituents $R^4$.

Preferred compounds of formula I are those, wherein $R^4$ is —$S(O)_2$-lower alkyl, for example the following compounds:

{(3SR,4SR)-3-[(3-fluoro-4-trifluoromethyl-benzyl)-methyl-amino]-4-phenyl-pyrrolidin-1-yl}-(4-methanesulfonyl-piperazin-1-yl)-methanone;

{(3SR,4RS)-3-(4-chloro-phenyl)-4-[(3,4-dichloro-benzyl)-methyl-amino]-pyrrolidin-1-yl}-(4-methanesulfonyl-piperazin-1-yl)-methanone;

[(3RS,4SR)-3-(biphenyl-4-ylmethyl-methyl-amino)-4-(4-chloro-phenyl)-pyrrolidin-1-yl]-(4-methanesulfonyl-piperazin-1-yl)-methanone;

[(3RS,4 SR)-3-[(4-chloro-3-fluoro-benzyl)-methyl-amino]-4-(4-chloro-phenyl)-pyrrolidin-1-yl]-(4-methanesulfonyl-piperazin-1-yl)-methanone;

{(3SR,4RS)-3-(4-chloro-phenyl)-4-[(3-fluoro-4-trifluoromethyl-benzyl)-methyl-amino]-pyrrolidin-1-yl}-(4-methanesulfonyl-piperazin-1-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-methanesulfonyl-piperazin-1-yl)-methanone;

[(3RS,4SR)-3-[(3,4-dichloro-benzyl)-methyl-amino]-4-(3,4-dichloro-phenyl)-pyrrolidin-1-yl]-(4-methanesulfonyl-piperazin-1-yl)-methanone;

[(3RS,4SR)-3-[(4-chloro-benzyl)-methyl-amino]-4-(3,4-dichloro-phenyl)-pyrrolidin-1-yl]-(4-methanesulfonyl-piperazin-1-yl)-methanone;

4-({[(3RS,4SR)-4-(3,4-dichloro-phenyl)-1-(4-methanesulfonyl-piperazine-1-carbonyl)-pyrrolidin-3-yl]-methyl-amino}-methyl)-benzonitrile;

{(3SR,4RS)-3-(3,4-dichloro-phenyl)-4-[(3,4-difluoro-benzyl)-methyl-amino]-pyrrolidin-1-yl}-(4-methanesulfonyl-piperazin-1-yl)-methanone;

{(3SR,4RS)-3-(3,4-dichloro-phenyl)-4-[(2,3-dihydro-benzofuran-6-ylmethyl)-methyl-amino]-pyrrolidin-1-yl}-(4-methanesulfonyl-piperazin-1-yl)-methanone;

{(3SR,4RS)-3-(3,4-dichloro-phenyl)-4-[(4-fluoro-3-methyl-benzyl)-methyl-amino]-pyrrolidin-1-yl}-(4-methanesulfonyl-piperazin-1-yl)-methanone;

{(3SR,4RS)-3-(3,4-dichloro-phenyl)-4-[(1H-indol-6-ylmethyl)-methyl-amino]-pyrrolidin-1-yl}-(4-methanesulfonyl-piperazin-1-yl)-methanone;

4-({[(3RS,4SR)-4-(3,4-dichloro-phenyl)-1-(4-methanesulfonyl-piperazine-1-carbonyl)-pyrrolidin-3-yl]-methyl-amino}-methyl)-2-fluoro-benzonitrile;

{(3SR,4RS)-3-(3,4-dichloro-phenyl)-4-[(3-fluoro-4-trifluoromethyl-benzyl)-methyl-amino]-pyrrolidin-1-yl}-((S)-4-methanesulfonyl-3-methyl-piperazin-1-yl)-methanone;

{(3SR,4RS)-3-(3,4-dichloro-phenyl)-4-[(3-fluoro-4-trifluoromethyl-benzyl)-methyl-amino]-pyrrolidin-1-yl}-((R)-4-methanesulfonyl-3-methyl-piperazin-1-yl)-methanone;

{(3SR,4RS)-3-(4-chloro-3-fluoro-phenyl)-4-[(3-fluoro-4-trifluoromethyl-benzyl)-methyl-amino]-pyrrolidin-1-yl}-(4-methanesulfonyl-piperazin-1-yl)-methanone;

{(3SR,4RS)-3-(4-chloro-3-fluoro-phenyl)-4-[(3-fluoro-4-trifluoromethyl-benzyl)-methyl-amino]-pyrrolidin-1-yl}-(4-methanesulfonyl-[1,4]diazepan-1-yl)-methanone;

{(3SR,4RS)-3-(3,4-dichloro-phenyl)-4-[methyl-(4-trifluoromethyl-benzyl)-amino]-pyrrolidin-1-yl}-(4-methanesulfonyl-piperazin-1-yl)-methanone; and 1-{(3SR,4RS)-3-(3,4-dichloro-phenyl)-4-[(3-fluoro-4-trifluoromethyl-benzyl)-methyl-amino]-pyrrolidin-1-yl}-2-(4-methanesulfonyl-piperazin-1-yl)-ethanone.

Preferred compounds of formula I are those, wherein $R^4$ is lower alkyl, for example the following compounds:

1-{(3SR,4RS)-3-(3,4-dichloro-phenyl)-4-[(3-fluoro-4-trifluoromethyl-benzyl)-methyl-amino]-pyrrolidin-1-yl}-5-(4-methyl-piperazin-1-yl)-pentan-1-one;

1-{(3SR,4RS)-3-(3,4-dichloro-phenyl)-4-[(3-fluoro-4-trifluoromethyl-benzyl)-methyl-amino]-pyrrolidin-1-yl}-2-(4-methyl-piperazin-1-yl)-ethanone;

1-{(3SR,4RS)-3-(3,4-dichloro-phenyl)-4-[(3-fluoro-4-trifluoromethyl-benzyl)-methyl-amino]-pyrrolidin-1-yl}-2-(3,5-dimethyl-piperazin-1-yl)-ethanone;

1-{(3SR,4RS)-3-(3,4-dichloro-phenyl)-4-[(3-fluoro-4-trifluoromethyl-benzyl)-methyl-amino]-pyrrolidin-1-yl}-2-((S)-3-methyl-piperazin-1-yl)-ethanone;

1-{(3SR,4RS)-3-(3,4-dichloro-phenyl)-4-[(3-fluoro-4-trifluoromethyl-benzyl)-methyl-amino]-pyrrolidin-1-yl}-2-((R)-3-methyl-piperazin-1-yl)-ethanone; and 1-{(3SR,4RS)-3-(3,4-dichloro-phenyl)-4-[(3-fluoro-4-trifluoromethyl-benzyl)-methyl-amino]-pyrrolidin-1-yl}-2-(2,6-dimethyl-morpholin-4-yl)-ethanone.

Preferred compounds of formula I are those, wherein $R^4$ is —$S(O)_2$—NR'R", for example the following compounds:

4-{(3SR,4RS)-3-(3,4-dichloro-phenyl)-4-[(3-fluoro-4-trifluoromethyl-benzyl)-methyl-amino]-pyrrolidine-1-carbonyl}-piperazine-1-sulfonic acid dimethylamide;

4-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperazine-1-sulfonic acid dimethylamide; and 4-(5-{(3SR,4RS)-3-(3,4-dichloro-phenyl)-4-[(3-fluoro-4-trifluoromethyl-benzyl)-methyl-amino]-pyrrolidin-1-yl}-5-oxo-pentyl)-piperazine-1-sulfonic acid dimethylamide.

Preferred compounds of formula I are those, wherein $R^4$ is —NR'—$S(O)_2$-lower alkyl, for example the following compounds:

N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-methanesulfonamide and N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-N-methyl-methanesulfonamide.

Preferred compounds of formula I are those, wherein $R^4$ is —C(O)-lower alkyl, for example the following compounds:

1-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-ethanone and 2-(4-acetyl-piperazin-1-yl)-1-{(3SR,4RS)-3-(3,4-dichloro-phenyl)-4-[(3-fluoro-4-trifluoromethyl-benzyl)-methyl-amino]-pyrrolidin-1-yl}-ethanone.

Preferred compounds of formula I are those, wherein $R^4$ is —NR'—C(O)-lower alkyl, for example the following compounds:

N-[1-(5-{(3SR,4RS)-3-(3,4-dichloro-phenyl)-4-[(3-fluoro-4-trifluoromethyl-benzyl)-methyl-amino]-pyrrolidin-1-yl}-5-oxo-pentyl)-piperidin-4-yl]-acetamide;

N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-N-methyl-acetamide;
N-[(S)-1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-pyrrolidin-3-yl]-acetamide;
N-[(R)-1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-pyrrolidin-3-yl]-acetamide; and
N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-acetamide.

Preferred compounds of formula I are those, wherein $R^4$ is —$(CH_2)_p$—NR'R"—, for example the following compounds:
{(3SR,4RS)-3-(3,4-dichloro-phenyl)-4-[(3-fluoro-4-trifluoromethyl-benzyl)-methyl-amino]-pyrrolidin-1-yl}-((R)-3-dimethylamino-pyrrolidin-1-yl)-methanone;
1-{(3SR,4RS)-3-(3,4-dichloro-phenyl)-4-[(3-fluoro-4-trifluoromethyl-benzyl)-methyl-amino]-pyrrolidin-1-yl}-2-[4-(2-dimethylamino-ethyl)-piperazin-1-yl]-ethanone;
{(3SR,4RS)-3-(3,4-dichloro-phenyl)-4-[(3-fluoro-4-trifluoromethyl-benzyl)-methyl-amino]-pyrrolidin-1-yl}-[4-(3-dimethylamino-propyl)-piperazin-1-yl]-methanone;
{(3SR,4RS)-3-(3,4-dichloro-phenyl)-4-[(3-fluoro-4-trifluoromethyl-benzyl)-methyl-amino]-pyrrolidin-1-yl}-[4-(2-dimethylamino-ethyl)-piperazin-1-yl]-methanone; and
1-{(3SR,4RS)-3-(3,4-dichloro-phenyl)-4-[(3-fluoro-4-trifluoromethyl-benzyl)-methyl-amino]-pyrrolidin-1-yl}-2-(4-dimethylamino-piperidin-1-yl)-ethanone.

Preferred compounds of formula I are those, wherein $R^4$ is heteroaryl, optionally substituted by alkoxy or cyano, for example the following compounds:
{(3SR,4RS)-3-(3,4-dichloro-phenyl)-4-[(3-fluoro-4-trifluoromethyl-benzyl)-methyl-amino]-pyrrolidin-1-yl}-(4-pyrimidin-2-yl-piperazin-1-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-pyridin-2-yl-piperazin-1-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-pyridin-4-yl-piperazin-1-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(2,3,5,6-tetrahydro-[1,2]bipyrazinyl-4-yl)-methanone;
2-(4-{(3S,4R)-3-(3,4-dichloro-phenyl)-4-[(3-fluoro-4-trifluoromethyl-benzyl)-methyl-amino]-pyrrolidine-1-carbonyl}-piperazin-1-yl)-nicotinonitrile;
6-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-nicotinonitrile; and
{(3SR,4RS)-3-(3,4-dichloro-phenyl)-4-[(3-fluoro-4-trifluoromethyl-benzyl)-methyl-amino]-pyrrolidin-1-yl}-[4-(6-methoxy-pyridin-2-yl)-piperazin-1-yl]-methanone.

Preferred compounds of formula I are those, wherein $R^4$ is aryl, optionally substituted by alkoxy or cyano, for example the following compounds:
{(3SR,4RS)-3-(3,4-dichloro-phenyl)-4-[(3-fluoro-4-trifluoromethyl-benzyl)-methyl-amino]-pyrrolidin-1-yl}-[4-(4-methoxy-phenyl)-piperazin-1-yl]-methanone;
2-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-benzonitrile; and
4-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-benzonitrile.

Preferred compounds of formula I are those, wherein $R^4$ is —$(CH_2)_p$OH—, for example the following compounds:
{(3SR,4RS)-3-(3,4-dichloro-phenyl)-4-[(3-fluoro-4-trifluoromethyl-benzyl)-methyl-amino]-pyrrolidin-1-yl}-[4-(3-hydroxy-propyl)-piperazin-1-yl]-methanone;
{(3SR,4RS)-3-(3,4-dichloro-phenyl)-4-[(3-fluoro-4-trifluoromethyl-benzyl)-methyl-amino]-pyrrolidin-1-yl}-[4-(2-hydroxy-ethyl)-piperazin-1-yl]-methanone;
1-{(3SR,4RS)-3-(3,4-dichloro-phenyl)-4-[(3-fluoro-4-trifluoromethyl-benzyl)-methyl-amino]-pyrrolidin-1-yl}-2-[4-(3-hydroxy-propyl)-piperazin-1-yl]-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-(4-hydroxy-piperidin-1-yl)-ethanone; and
{(3SR,4RS)-3-(3,4-dichloro-phenyl)-4-[(3-fluoro-4-trifluoromethyl-benzyl)-methyl-amino]-pyrrolidin-1-yl}-(4-hydroxy-3,4,5,6-tetrahydro-2H-[4,4']bipyridinyl-1-yl)-methanone.

Preferred compounds of formula I are those, wherein $R^4$ is —C(O)—NR'R", for example the following compound:
4-{(3SR,4RS)-3-(3,4-dichloro-phenyl)-4-[(3-fluoro-4-trifluoromethyl-benzyl)-methyl-amino]-pyrrolidine-1-carbonyl}-piperazine-1-carboxylic acid diethylamide.

Preferred compounds of formula I are those, wherein $R^4$ is —$(CH_2)_p$CN—, for example the following compounds:
3-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-propionitrile;
3-[4-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperazin-1-yl]-propionitrile; and
1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidine-4-carbonitrile.

Preferred compounds of formula I are those, wherein $R^4$ is heterocyclyl, optionally substituted by =O, for example the following compounds:
4-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-morpholin-3-one and
1'-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-[1,4']bipiperidinyl-2-one.

Preferred compounds of formula I are those, wherein $R^4$ is 2-oxa-5-aza-bicyclo[2.2.1]hept-5-yl, for example the following compound:
1-{(3SR,4RS)-3-(3,4-dichloro-phenyl)-4-[(3-fluoro-4-trifluoromethyl-benzyl)-methyl-amino]-pyrrolidin-1-yl}-2-(1S,4R)-2-oxa-5-aza-bicyclo[2.2.1]hept-5-yl-ethanone.

Preferred compounds of formula I are those, wherein $R^4$ is —C(O)-lower cycloalkyl, substituted by lower alkyl, for example the following compound:
(3SR,4RS)-3-(3,4-dichloro-phenyl)-4-[(3-fluoro-4-trifluoromethyl-benzyl)-methyl-amino]-pyrrolidin-1-yl}-[1-(1-methyl-cyclopropanecarbonyl)-piperidin-4-yl]-methanone.

Preferred compounds of formula I are those, wherein $R^3$ is —$(CH_2)_p$NR'R", for example the following compounds:
1-{(3SR,4RS)-3-(3,4-dichloro-phenyl)-4-[(3-fluoro-4-trifluoromethyl-benzyl)-methyl-amino]-pyrrolidin-1-yl}-5-methylamino-pentan-1-one and
1-{(3 SR,4RS)-3-(3,4-dichloro-phenyl)-4-[(3-fluoro-4-trifluoromethyl-benzyl)-methyl-amino]-pyrrolidin-1-yl}-5-dimethylamino-pentan-1-one Preferred compounds of formula I are those, wherein $R^3$ is —$(CH_2)_p$-heteroaryl, for example the following compound:
1-{(3SR,4RS)-3-(3,4-dichloro-phenyl)-4-[(3-fluoro-4-trifluoromethyl-benzyl)-methyl-amino]-pyrrolidin-1-yl}-5-imidazol-1-yl-pentan-1-one.

Preferred compounds of formula I are those, wherein $R^3$ is —$(CH_2)_p$—C(O)-heteroaryl, for example the following compounds:
1-{(3SR,4RS)-3-(3,4-dichloro-phenyl)-4-[(3-fluoro-4-trifluoromethyl-benzyl)-methyl-amino]-pyrrolidin-1-yl}-6-pyridin-2-yl-hexane-1,6-dione.

Preferred compounds of formula I are those, wherein $R^3$ is —$(CH_2)_p$—C(O)—NR'R", for example the following compound:
6-{(3SR,4RS)-3-(3,4-dichloro-phenyl)-4-[(3-fluoro-4-trifluoromethyl-benzyl)-methyl-amino]-pyrrolidin-1-yl}-6-oxo-hexanoic acid amide.

Preferred compounds of formula I are those, wherein $R^3$ is —$(CH_2)_p$—O-lower alkyl, for example the following compound:
1-{(3S,4R)-3-(3,4-dichloro-phenyl)-4-[(3-fluoro-4-trifluoromethyl-benzyl)-methyl-amino]-pyrrolidin-1-yl}-5-methoxy-pentan-1-one.

Preferred compounds of formula I are those, wherein $R^3$ is —$(CH_2)_p$—CN, for example the following compound:
6-{(3SR,4RS)-3-(3,4-dichloro-phenyl)-4-[(3-fluoro-4-trifluoromethyl-benzyl)-methyl-amino]-pyrrolidin-1-yl}-6-oxo-hexanenitrile.

Preferred compounds of formula I are those, wherein $R^3$ is —$(CH_2)_p$—NR'—$(CH_2)_p$NR'R", for example the following compounds:
1-{(3SR,4RS)-3-(3,4-dichloro-phenyl)-4-[(3-fluoro-4-trifluoromethyl-benzyl)-methyl-amino]-pyrrolidin-1-yl}-2-(2-dimethylamino-ethylamino)-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-(3-dimethylamino-propylamino)-ethanone; and
1-{(3SR,4RS)-3-(3,4-dichloro-phenyl)-4-[(3-fluoro-4-trifluoromethyl-benzyl)-methyl-amino]-pyrrolidin-1-yl}-2-[(3-dimethylamino-propyl)-methyl-amino]-ethanone.

Preferred compounds of formula I are those, wherein $R^3$ is —$(CH_2)_p$—NR'—$(CH_2)$p'-CN, for example the following compounds:
3-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethylamino)-propionitrile and
3-[(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-methyl-amino]-propionitrile.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, and, depending on the starting materials and their respective reactivity, the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises a) coupling a compound of formula

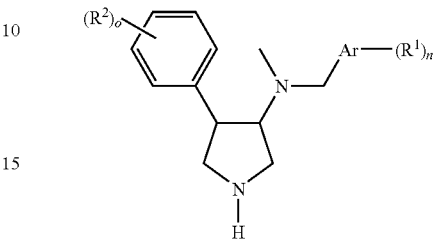

with a suitable acid chloride or carboxylic acid of formula

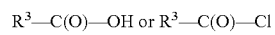

to obtain a compound of formula

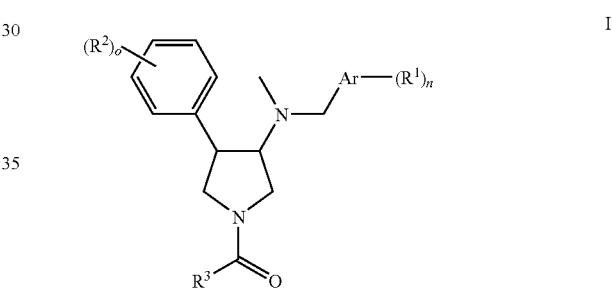

wherein the groups Ar, $R^1$, $R^2$ and $R^3$ and the definitions o and n are described above, or b) alkylating a compound of formula

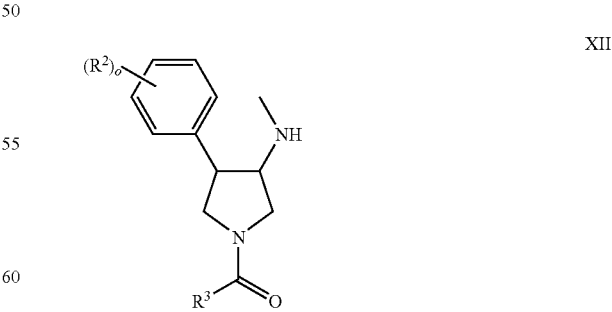

with a compound of formula

to obtain a compound of formula

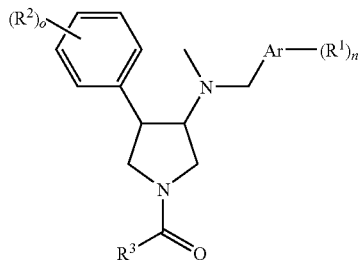

wherein the groups Ar, $R^1$, $R^2$ and $R^3$ and the definitions o and n are described above, and, if desired, converting the compounds obtained into pharmaceutically acceptable acid addition salts.

The preparation of compounds of formula I is further described in more detail in general schemes 1-4, in general procedures I-VIII and in examples 1-149.

As mentioned earlier, the compounds of formula I and their pharmaceutically usable addition salts possess valuable pharmacological properties. Compounds of the present invention are antagonists of neurokinin 3 (NK-3) receptors. The compounds were investigated in accordance with the tests given hereinafter.

Experimental Procedure

The compounds were investigated in accordance with the tests given hereinafter.

General scheme 1

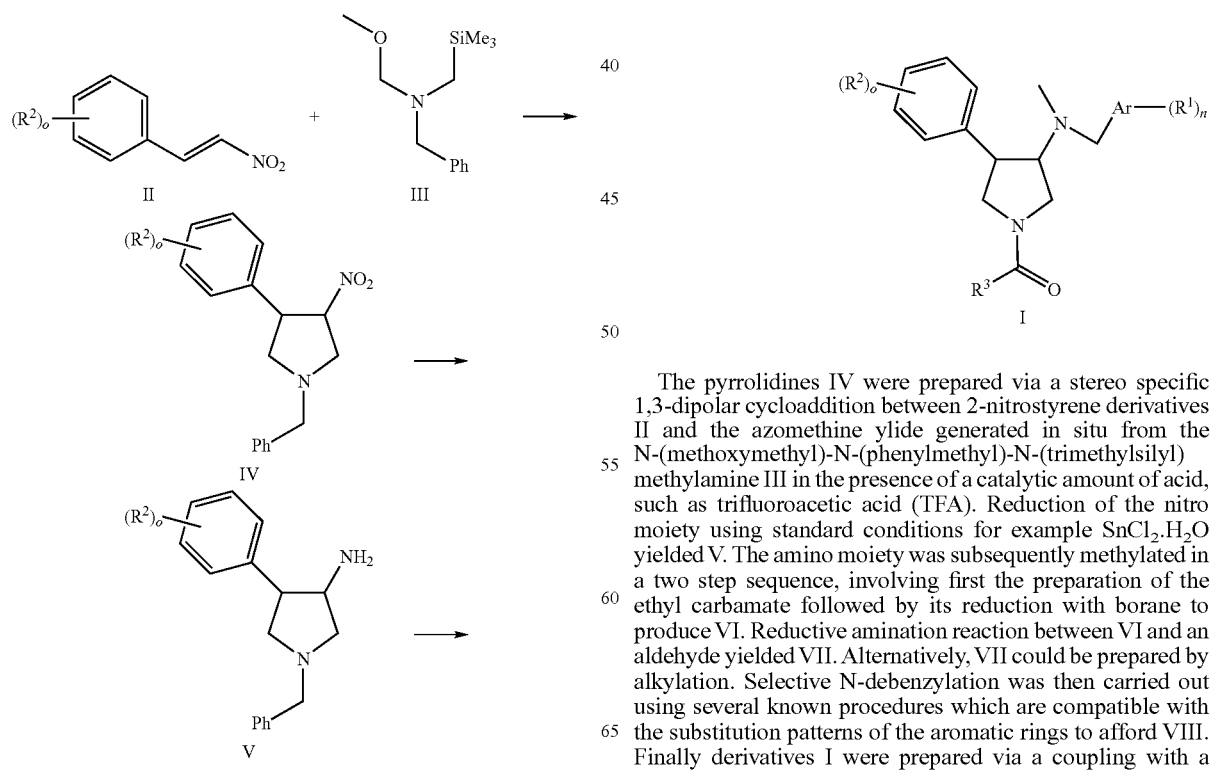

The pyrrolidines IV were prepared via a stereo specific 1,3-dipolar cycloaddition between 2-nitrostyrene derivatives II and the azomethine ylide generated in situ from the N-(methoxymethyl)-N-(phenylmethyl)-N-(trimethylsilyl) methylamine III in the presence of a catalytic amount of acid, such as trifluoroacetic acid (TFA). Reduction of the nitro moiety using standard conditions for example $SnCl_2.H_2O$ yielded V. The amino moiety was subsequently methylated in a two step sequence, involving first the preparation of the ethyl carbamate followed by its reduction with borane to produce VI. Reductive amination reaction between VI and an aldehyde yielded VII. Alternatively, VII could be prepared by alkylation. Selective N-debenzylation was then carried out using several known procedures which are compatible with the substitution patterns of the aromatic rings to afford VIII. Finally derivatives I were prepared via a coupling with a corresponding acid chloride or carboxylic acid.

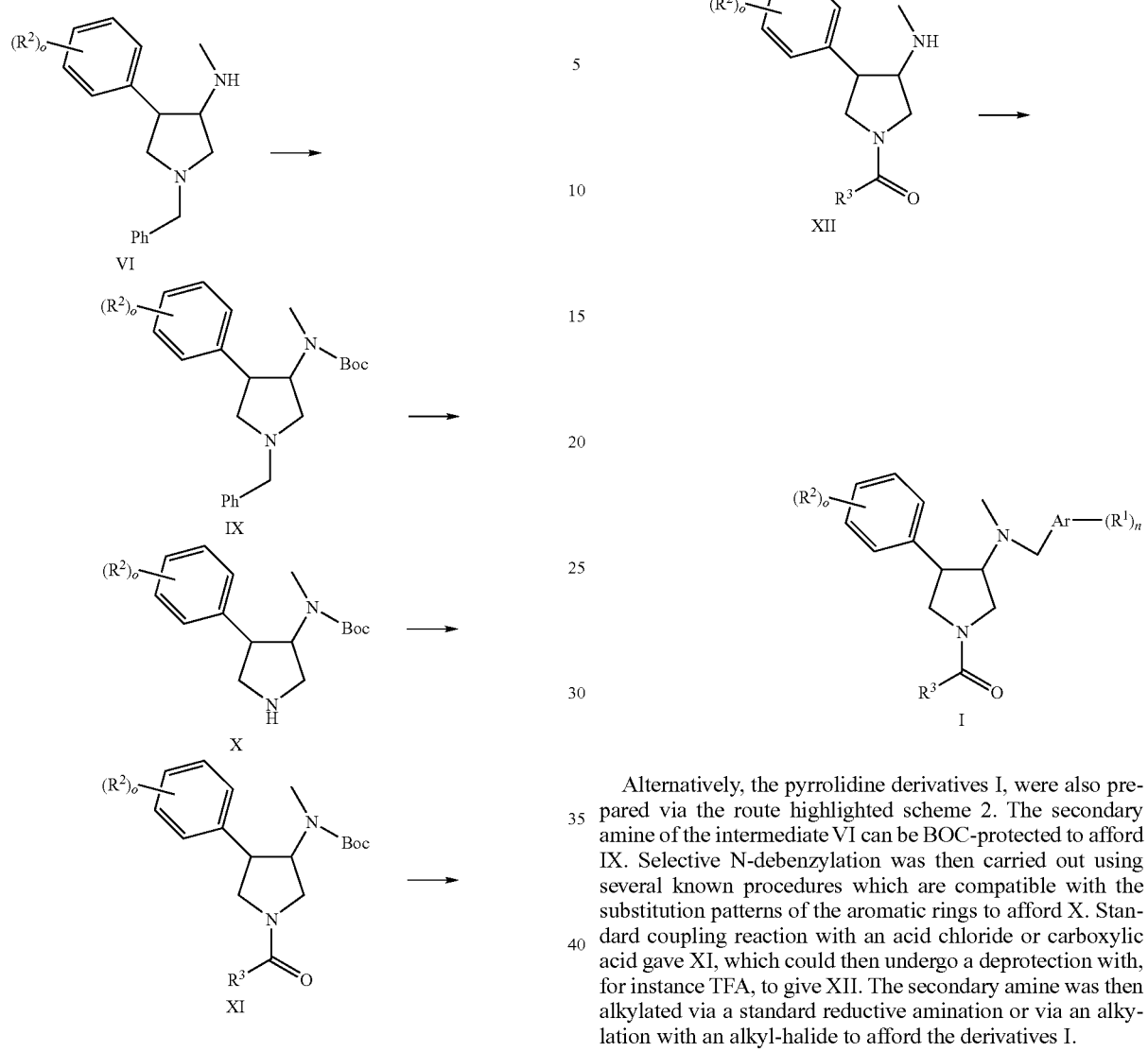

Alternatively, the pyrrolidine derivatives I, were also prepared via the route highlighted scheme 2. The secondary amine of the intermediate VI can be BOC-protected to afford IX. Selective N-debenzylation was then carried out using several known procedures which are compatible with the substitution patterns of the aromatic rings to afford X. Standard coupling reaction with an acid chloride or carboxylic acid gave XI, which could then undergo a deprotection with, for instance TFA, to give XII. The secondary amine was then alkylated via a standard reductive amination or via an alkylation with an alkyl-halide to afford the derivatives I.

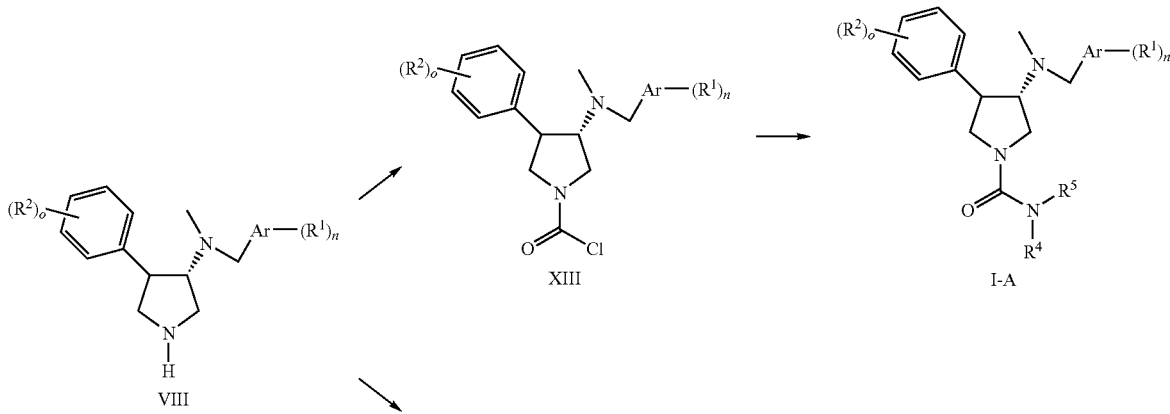

-continued

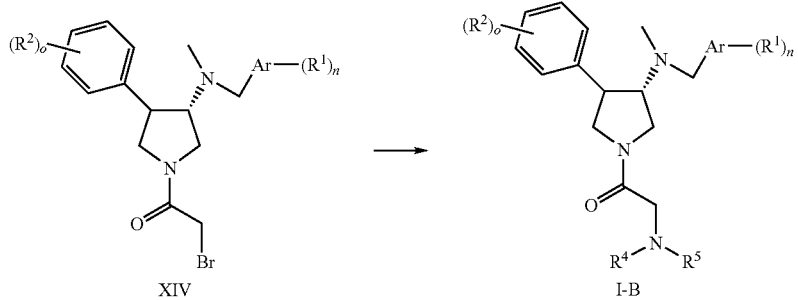

Alternatively, intermediates VIII could be converted in a two step sequence into final compound I-A or I-B. For instance, the treatment of derivatives VIII with triphosgene in the presence of a base, preferably pyridine, and at low temperature yielded pyrrolidine-1-carbonyl chloride derivatives XIII. The coupling between compounds XIII and a primary or secondary amine gave access to urea of formula I-A. The treatment of derivatives VIII with bromo-acetyl chloride in the presence of a base yielded intermediates XIV. A nucleophilic substitution reaction between XIV and a primary or secondary amine gave access to amide of formula I-B.

derivatives of the types I-C. The treatment of derivatives VIII with 3-chloropropyl chloroformate in the presence of a base yielded intermediates XVI. A nucleophilic substitution reaction yielded pyrrolidine derivatives of the types I-D. Nucleophiles could be a primary or secondary amine.

Experimental Part

Abbreviations $CH_2Cl_2$=dichloromethane;
DMAP=dimethylaminopyridine;

General scheme 4

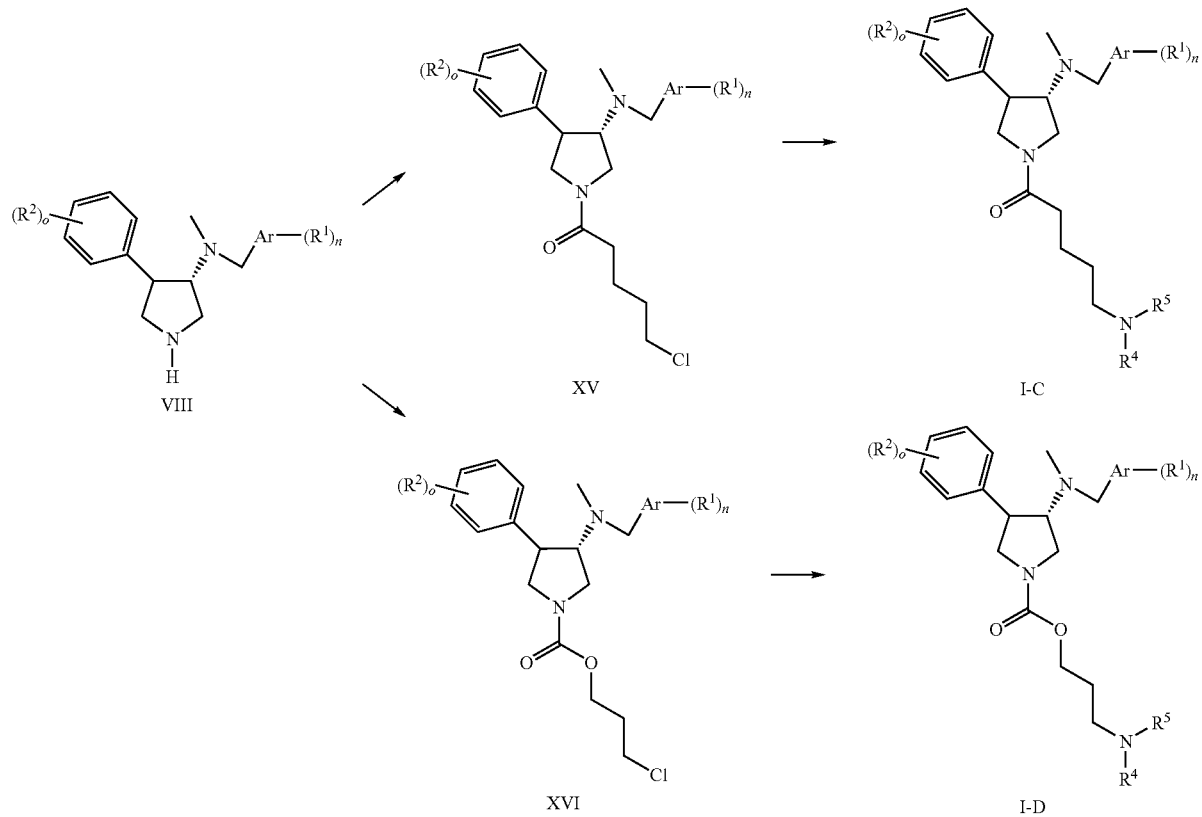

Alternatively, intermediates VIII could be converted in a two step sequence into final compound I-C or I-D. For instance, the treatment of derivatives VIII with 5-Bromopentanoyl chloride yielded pyrrolidine derivatives of general formula XV. A nucleophilc substitution reaction yielded final HOBt=1-hydroxy-benzotriazol hydrat;
EDC=1-(3-dimethylaminopropyl)-3-ethylcarbodiimide hydrochloride;
$Et_3N$=triethylamine;
EtOAc=ethyl acetate;

H=hexane;
RT=room temperature;
General Procedure I (Amide Coupling)

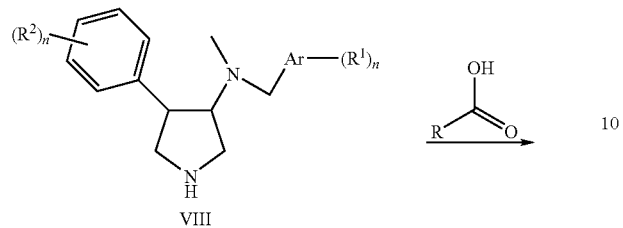

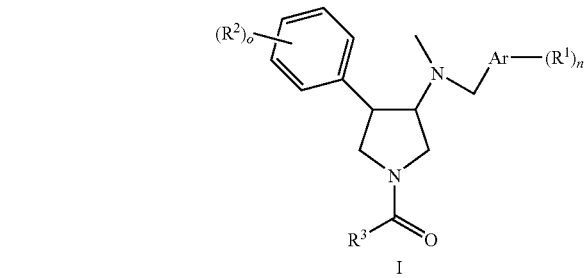

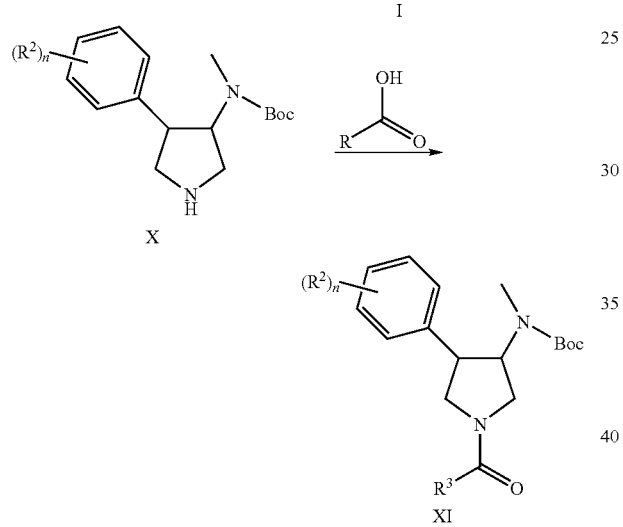

To a stirred solution of a carboxylic acid derivative (commercially available or known in the literature) (1 mmol) in 10 mL of $CH_2Cl_2$ was added (1.3 mmol) of EDC, (1.3 mmol) of HOBt and $Et_3N$ (1.3 mmol). After one hour at RT, was added a pyrrolidine intermediate of general formula (VIII or X). The mixture was stirred at RT overnight and then poured onto water and extracted with $CH_2Cl_2$. The combined organic phases were dried over $Na_2SO_4$ and concentrated under vacuo. Flash chromatography or preparative HPLC afforded the title compound.

General Procedure II (Amid or Urea Preparation)

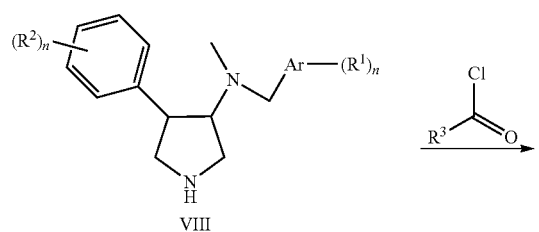

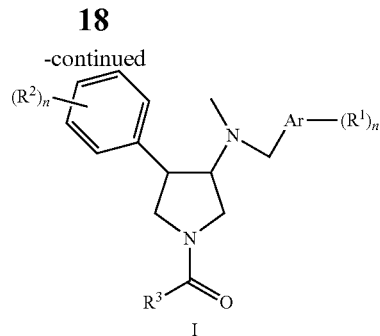

To a stirred solution of a pyrrolidine intermediate VIII (1 mmol) in $CH_2Cl_2$ (15 ml) at RT were added ethyl-diisopropyl-amine (2 mmol) and an acid chloride or carbamoyl chloride or chloroformate derivative of formula RCOCl (1.1 mmol). Stirring was continued until completion of the reaction. The reaction mixture was then concentrated under vacuo and purified by flash chromatography on $SiO_2$ or by preparative HPLC.

General Procedure III (Reductive Amination)

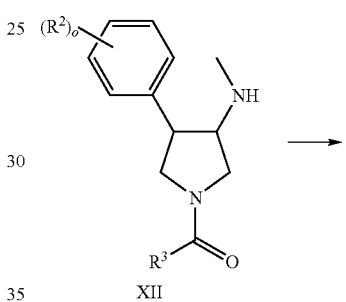

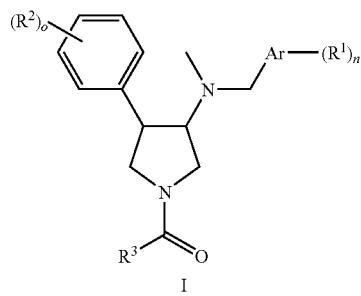

To a stirred solution of a pyrrolidine intermediate XII (1.00 mmol) in MeOH (6 ml) was added the aldehyde (1.20 mmol). Then a solution of $NaBH_3CN$ (1.3 mol) in MeOH (1.5 ml) and AcOH (0.01 ml) were added. The reaction mixture was stirred overnight at RT, concentrated under vacuo, diluted with EtOAc, washed with $H_2O$. The organic phases were dried over $Na_2SO_4$ and the product purified by flash chromatography ($SiO_2$) or by preparative HPLC to afford the desired compound.

General Procedure IV (Alkylation)

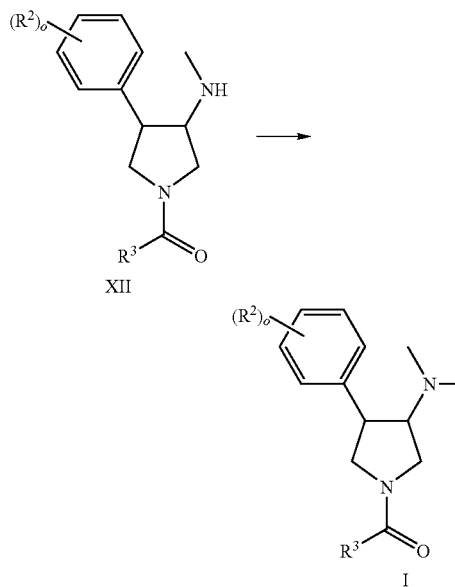

To a stirred solution of a pyrrolidine intermediate XII (1.00 mmol) in CH$_2$Cl$_2$ (6 ml) was added a substituted benzyl bromide derivative (1.20 mmol) and N,N-diisopropylethylamine (1.50 mmol). The reaction mixture was stirred at 45° C. overnight, washed with H$_2$O. The organic phases were dried over Na$_2$SO$_4$ and the product purified by flash chromatography (SiO$_2$) or by preparative HPLC to afford the desired compound.

General Procedure V:

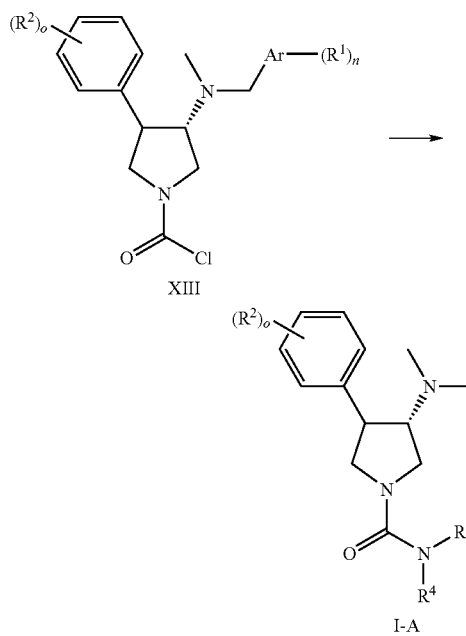

To a stirred solution of a pyrrolidine carbonyl chloride intermediate XIII (1 mmol) in CH$_2$Cl$_2$ (15 ml) at RT were added ethyl-diisopropyl-amine (1.2 mmol) and a primary or secondary amine (1.1 mmol). Stirring was continued until completion of the reaction. The reaction mixture was then concentrated under vacuo and purified by flash chromatography on SiO$_2$ or by preparative HPLC to yield I-A.

General Procedure VI:

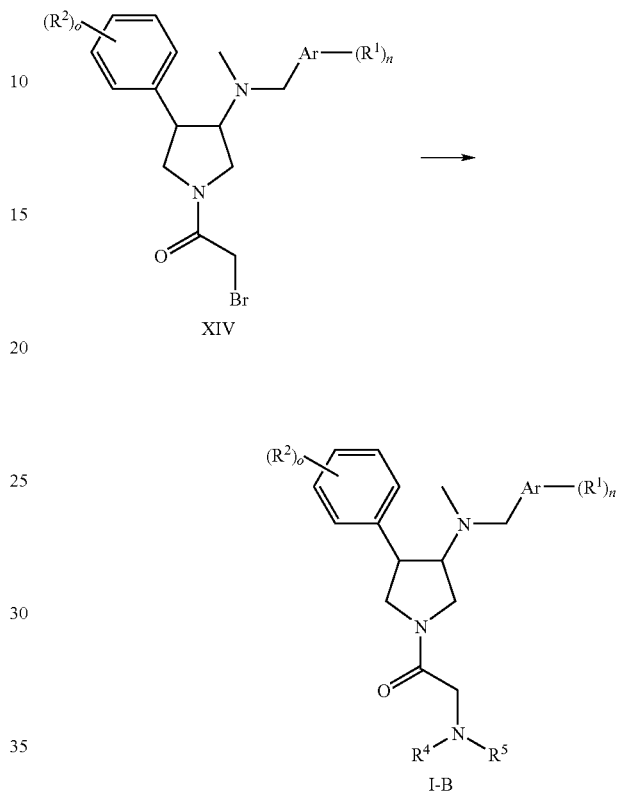

To a stirred solution of a pyrrolidine acetyl bromid intermediate XIV (1 mmol) in THF (15 ml) at RT were added ethyl-diisopropyl-amine (1.2 mmol) and a primary or secondary amine (4 mmol). Stirring was continued until completion of the reaction. The reaction mixture was then concentrated under vacuo and purified by flash chromatography on SiO$_2$ or by preparative HPLC to yield I-B.

General Procedure VII:

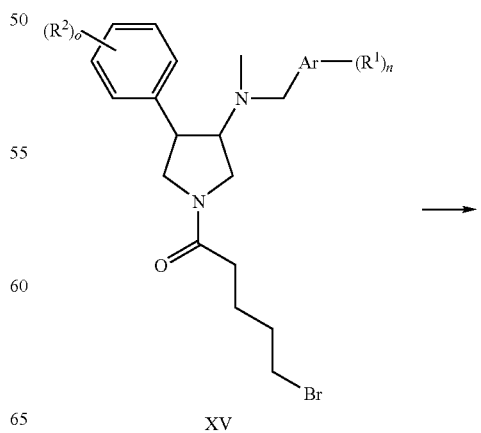

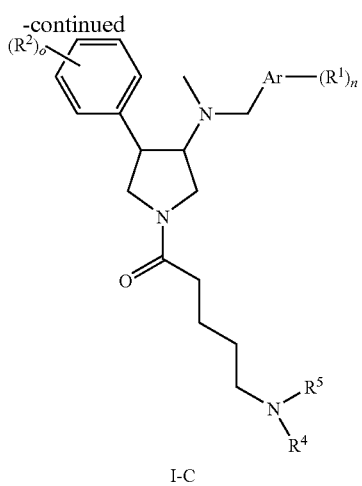

I-C

To a stirred solution of a pyrrolidine intermediate XV (1 mmol) in THF (15 ml) at RT were added ethyl-diisopropyl-amine (1.2 mmol) and a primary or secondary amine (4 mmol). Stirring was continued until completion of the reaction. The reaction mixture was then concentrated under vacuo and purified by flash chromatography on SiO$_2$ or by preparative HPLC to yield I-C.

General Procedure VIII:

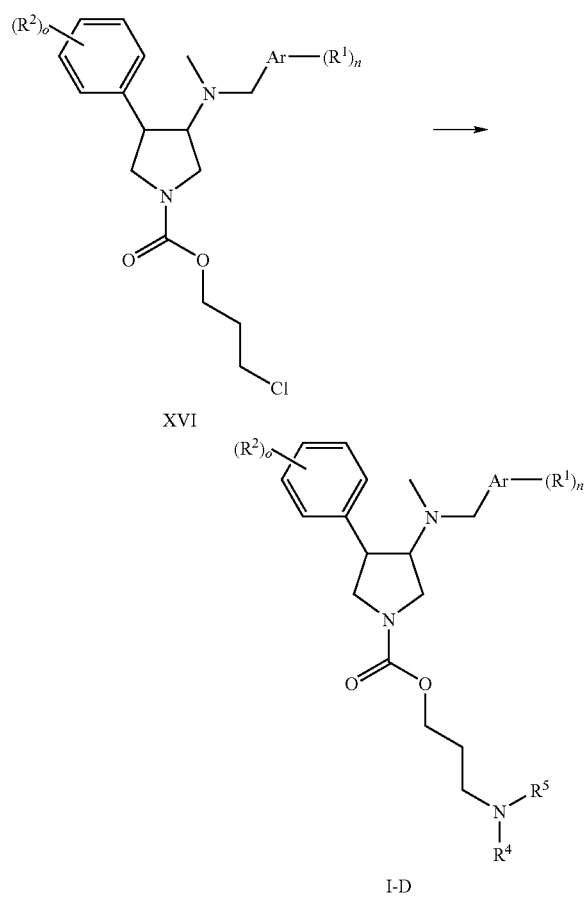

To a stirred solution of a pyrrolidine intermediate XVI (1 mmol) in THF (15 ml) at RT were added ethyl-diisopropyl-amine (1.2 mmol) and a primary or secondary amine (4 mmol). Stirring was continued until completion of the reaction. The reaction mixture was then concentrated under vacuo and purified by flash chromatography on SiO$_2$ or by preparative HPLC to yield I-D.

Process for Preparation of Pyrrolidine Intermediates of Formula VIII

Pyrrolidine VIII-1

[(3RS,4SR)-4-(3,4-Dichloro-phenyl)-pyrrolidin-3-yl]-(3-fluoro-4-trifluoromethyl-benzyl)-methyl-amine

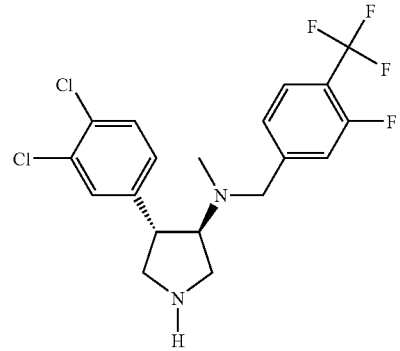

a) (3SR,4RS)-1-Benzyl-3-(3,4-dichloro-phenyl)-4-nitro-pyrrolidine

A solution of N-(methoxymethyl)-N-(phenylmethyl)-N-(trimethylsilyl)methylamine (1.96 g, 8.2 mmol) in CH$_2$Cl$_2$ (10 ml) was added drop wise, over a 30 minutes period, to a stirred solution of 1,2-dichloro-4-((E)-2-nitro-vinyl)-benzene (1.0 g, 4.58 mmol) and trifluoroacetic acid (52 mg, 4.45 mmol) in CH$_2$Cl$_2$ (5 ml) at 0° C. The ice bath was removed, and the solution was stirred at 25° C. for an additional 48 h. It was then concentrated and purification by flash chromatography (SiO$_2$, EtOAc/H 1:4) afforded 1.00 g (62%) of the title compound as a colorless oil. ES-MS m/e: 351.4 (M+H$^+$).

b) (3RS,4SR)-1-Benzyl-4-(3,4-dichloro-phenyl)-pyrrolidin-3-ylamine

To a stirred solution of (3SR,4RS)-1-benzyl-3-(3,4-dichloro-phenyl)-4-nitro-pyrrolidine (15.0 g, 0.0427 mol) in EtOAc (200 ml) was added portionwise SnCl$_2$.2H$_2$O (43.36 g, 0.192 mol). The reaction mixture was then heated at reflux for 4 hours, cooled down to RT and a saturated aqueous solution of NaHCO$_3$ (500 ml) was added. The salts were filtered off and the product extracted with EtOAc. The organic phases were then dried over Na$_2$SO$_4$, and concentration under vacuum gave 9.30 g (75%) of the title compound as a light yellow oil. The product was then used in the next step without further purification. ES-MS m/e: 321.1 (M+H$^+$).

c) [(3RS,4SR)-1-Benzyl-4-(3,4-dichloro-phenyl)-pyrrolidin-3-yl]-methyl-amine To a solution of (3RS,4SR)-1-benzyl-4-(3,4-dichloro-phenyl)-pyrrolidin-3-ylamine (9.2 g, 0.028 mol) in THF (100 ml) was added a solution of $K_2CO_3$ (7.91 g, 0.057 mol) in $H_2O$ (35 ml). After 10 minutes, ethyl chloroformate (2.86 ml, 0.030 mol) was added and stirring was continued at RT for an additional 4 h. The intermediate carbamate was then extracted with $Et_2O$, dried over $Na_2SO_4$ and concentrated under vacuo to give viscous oil. The oil was taken up in THF (100 ml) and a solution of borane in THF (1M) was added (114.5 ml). The reaction mixture was then heated at 65° C. over night, cooled to RT and carefully quenched with conc. HCl (100 ml). The mixture was then heated at 80° C. for 2 h, cooled to RT, concentrated under vacuo, diluted with $Et_2O$ (100 ml) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 7.31 g (76%) of the title compound as a colorless oil. ES-MS m/e: 335.3 (M+H$^+$).

d) [(3RS,4SR)-1-Benzyl-4-(3,4-dichloro-phenyl)-pyrrolidin-3-yl]-(3-fluoro-4-trifluoromethyl-benzyl)-methyl-amine To a stirred solution of [3RS,4SR)-1-benzyl-4-(3,4-dichloro-phenyl)-pyrrolidin-3-yl]-methyl-amine (3.5 g, 0.010 mol) in MeOH (60 ml) was added 3-fluoro-4-trifluoromethyl-benzaldehyde (2.10 g, 0.0109 mol). Then a solution of $NaBH_3CN$ (0.79 g, 0.012 mol) in MeOH (15 ml) and AcOH (0.1 ml) were added. The reaction mixture was stirred overnight at RT, concentrated under vacuo, diluted with EtOAc, washed with $H_2O$. The organic phases were dried over $Na_2SO_4$ and the product purified by flash chromatography ($SiO_2$, EtOAc/Heptane 1:4) to afford 3.31 g (62%) of the title compound as a colorless oil.

e) [(3RS,4SR)-4-(3,4-Dichloro-phenyl)-pyrrolidin-3-yl]-(3-fluoro-4-trifluoromethyl-benzyl)-methyl-amine To a stirred solution of [(3RS,4SR)-1-benzyl-4-(3,4-dichloro-phenyl)-pyrrolidin-3-yl]-(3-fluoro-4trifluoromethyl-benzyl)-methyl-amine (3.30 g, 6.45 mmol) in $CH_3CN$ (45 ml) at RT, was added 2,2,2-trichloroethyl chloroformate (1.30 ml, 9.67 mmol). The reaction mixture was stirred at RT for 3 hours, concentrated under vacuo. The residue was dissolved in AcOH (10 ml) and zinc dust (1.0 g) was added portion wise over 3 hours. The solvent was evaporated, the residue diluted in EtOAc and the organic phase was washed with an aqueous solution of $NaHCO_3$. The organic phase was dried over $Na_2SO_4$, concentrated under vacuo to afford 1.43 g (53%) of the tile compound as a colorless oil. ES-MS m/e: 421.0 (M+H$^+$).

Pyrrolidine VIII-2

[(3RS,4SR)-4-(4-Chloro-3-fluoro-phenyl)-pyrrolidin-3-yl]-(3-fluoro-4-trifluoromethyl-benzyl)-methyl-amine

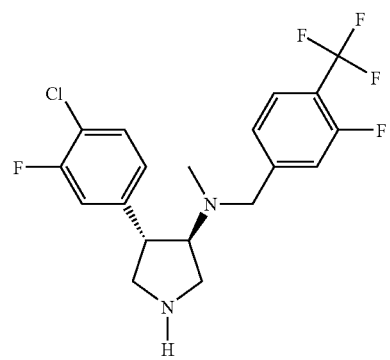

a) (3SR,4RS)-1-Benzyl-3-(4-chloro-3-fluoro-phenyl)-4-nitro-pyrrolidine

A solution of N-(methoxymethyl)-N-(phenylmethyl)-N-(trimethylsilyl)methylamine (1.00 g, 4.2 mmol) in $CH_2Cl_2$ (5 ml) was added drop wise, over a 30 minutes period, to a stirred solution of 1-chloro-2-fluoro-4-((E)-2-nitro-vinyl)-benzene (0.68 g, 3.37 mmol) and trifluoroacetic acid (30 ul) in $CH_2Cl_2$ (5 ml) at 0° C. The ice bath was removed, and the solution was stirred at 25° C. for an additional 48 h. It was then concentrated and purification by flash chromatography ($SiO_2$, EtOAc/H 1:4) afforded 0.78 g (55%) of the title compound as a colorless oil. ES-MS m/e: 335.2 (M+H$^+$).

b) (3RS,4SR)-1-Benzyl-4-(4-chloro-3-fluoro-phenyl)-pyrrolidin-3-ylamine

To a stirred solution of (3SR,4RS)-1-benzyl-3-(4-chloro-3-fluoro-phenyl)-4-nitro-pyrrolidine (0.78 g, 2.33 mmol) in EtOAc (15 ml) was added portion wise $SnCl_2.2H_2O$ (2.63 g, 11.6 mmol). The reaction mixture was then heated at reflux for 4 hours, cooled down to RT and a saturated aqueous solution of $NaHCO_3$ (500 ml) was added. The salts were filtered off and the product extracted with EtOAc. The organic phases were then dried over $Na_2SO_4$, and concentration under vacuum. A column chromatography ($CH_2Cl_2$/MeOH 95/5) gave 0.46 g (65%) of the title compound as a light brown oil. ES-MS m/e: 305.1 (M+H$^+$).

c) [(3RS,4SR)-1-Benzyl-4-(4-chloro-3-fluoro-phenyl)-pyrrolidin-3-yl]-methyl-amine To a solution of (3RS,4SR)-1-benzyl-4-(4-chloro-3-fluoro-phenyl)-pyrrolidin-3-ylamine (0.46 g, 1.51 mmol) in THF (5 ml) was added a solution of $K_2CO_3$ (0.419 g, 3.0 mmol) in $H_2O$ (2 ml). After 10 minutes, ethyl chloroformate (0.3 ml, 3.0 mmol) was added and stirring was continued at RT for an additional 4 h. The intermediate carbamate was then extracted with $Et_2O$, dried over $Na_2SO_4$ and concentrated under vacuo to give viscous oil. The oil was taken up in THF (10 ml) and a solution of borane in THF (1M) was added (6.0 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with $Et_2O$ (10 ml) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 0.34 g (70%) of the title compound as a colorless oil. ES-MS m/e: 319.1 (M+H$^+$).

d) [(3RS,4SR)-1-Benzyl-4-(4-chloro-3-fluoro-phenyl)-pyrrolidin-3-yl]-(3-fluoro-4-trifluoromethyl-benzyl)-methyl-amine To a stirred solution of [(3RS,4SR)-1-benzyl-4-(4-chloro-3-fluoro-phenyl)-pyrrolidin-3-yl]-methyl-amine (340 mg, 1.06 mmol) in MeOH (6 ml) was added 3-fluoro-4-trifluoromethyl-benzaldehyde (230 mg, 1.20 mmol). Then a solution of $NaBH_3CN$ (85 mg, 1.3 mol) in MeOH (1.5 ml) and AcOH (0.01 ml) were added. The reaction mixture was stirred overnight at RT, concentrated under vacuo, diluted with EtOAc, washed with $H_2O$. The organic phases were dried over $Na_2SO_4$ and the product purified by flash chromatography ($SiO_2$, EtOAc/Heptane 1:4) to afford 145 mg (28%) of the title compound as a colorless oil.

e) [(3RS,4SR)-4-(4-Chloro-3-fluoro-phenyl)-pyrrolidin-3-yl]-(3-fluoro-4-trifluoromethyl-benzyl)-methyl-amine To a stirred solution of [(3RS,4SR)-1-benzyl-4-(4-chloro-3-fluoro-phenyl)-pyrrolidin-3-yl]-(3-fluoro-4-trifluoromethyl-benzyl)-methyl-amine (145 mg, 0.29 mmol) in $CH_3CN$ (2 ml) at RT, was added 2,2,2-trichloroethyl chloroformate (0.06 ml, 0.44 mmol). The reaction mixture was stirred at RT for 3 hours, concentrated under vacuo. The residue was dissolved in AcOH (3 ml) and zinc dust (60 mg) was added portion wise over 3 hours. The solvent was evaporated, the residue diluted in EtOAc and the organic phase was washed with an aqueous solution of $NaHCO_3$. The organic phase was dried over $Na_2SO_4$, concentrated under vacuo to afford 80 mg (67%) of the tile compound as a colorless oil. ES-MS m/e: 405.3 (M+H$^+$).

Pyrrolidine VIII-3

[(3RS,4SR)-4-(3,4-Dichloro-phenyl)-pyrrolidin-3-yl]-methyl-(4-trifluoromethyl-benzyl)-amine

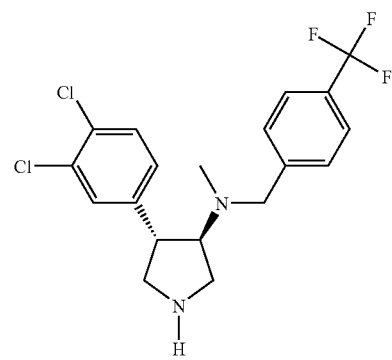

a) [(3RS,4SR)-1-Benzyl-4-(3,4-dichloro-phenyl)-pyrrolidin-3-yl]-methyl-(4-trifluoromethyl-benzyl)-amine To a stirred solution of [(3RS,4SR)-1-benzyl-4-(3,4-dichloro-phenyl)-pyrrolidin-3-yl]-methyl-amine (0.35 g, 1.04 mmol) in THF (6 ml) was added 1-bromomethyl-4-trifluoromethyl-benzene (0.27 g, 1.15 mmol) and $Et_3N$ (0.148 ml, 1.45 mmol). The reaction mixture was stirred overnight at RT and concentrated under vacuo. The product purified by flash chromatography ($SiO_2$, EtOAc/Heptane 1:4) to afford 130 mg (29%) of the title compound as a colorless oil. ES-MS m/e: 492.9 (M+H$^+$).

b) [(3RS,4SR)-4-(3,4-Dichloro-phenyl)pyrrolidin-3-yl]-methyl-(4-trifluoromethyl-benzyl)-amine To a stirred solution of [(3RS,4SR)-1-benzyl-4-(3,4-dichloro-phenyl)-pyrrolidin-3-yl]-methyl-(4-trifluoromethyl-benzyl)-amine (160 mg, 0.32 mmol) in $CH_3CN$ (5 ml) at RT, was added 2,2,2-trichloroethyl chloroformate (0.070 ml, 0.48 mmol). The reaction mixture was stirred at RT for 3 hours, concentrated under vacuo. The residue was dissolved in AcOH (3 ml) and zinc dust (80 mg) was added portion wise over 1 hours. The solvent was evaporated, the residue diluted in EtOAc and the organic phase was washed with an aqueous solution of $NaHCO_3$. The organic phase was dried over $Na_2SO_4$ and concentrated under vacuo. The product was purified by column chromatography (CH$_2$Cl$_2$/MeOH: 9/1) to afford 85 mg (65%) of the tile compound as a colorless oil. ES-MS m/e: 403.4 (M+H$^+$).

Pyrrolidine VIII-4

[(3RS,4SR)-4-(3-Chloro-phenyl)-pyrrolidin-3-yl]-(3-fluoro-4-trifluoromethyl-benzyl)-methyl-amine

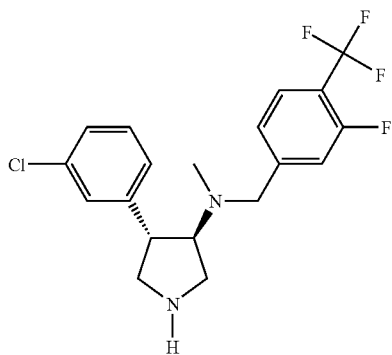

a) (3SR,4RS)-1-Benzyl-3-(3-chloro-phenyl)-4-nitro-pyrrolidine

A solution of N-(methoxymethyl)-N-(phenylmethyl)-N-(trimethylsilyl)methylamine (9.69 g, 41 mmol) in CH$_2$Cl$_2$ (40 ml) was added drop wise, over a 30 minutes period, to a stirred solution of 1-chloro-3-((E)-2-nitro-vinyl)-benzene (0.68 g, 3.37 mmol) and trifluoroacetic acid (0.21 ml) in CH$_2$Cl$_2$ (40 ml) at 0° C. The ice bath was removed, and the solution was stirred at 25° C. for an additional 48 h. It was then concentrated and purification by flash chromatography (SiO$_2$, EtOAc/H 1:4) afforded 6.30 g (73%) of the title compound as a colorless oil. ES-MS m/e: 317.1 (M+H$^+$).

b) (3RS,4SR)-1-Benzyl-4-(3-chloro-phenyl)-pyrrolidin-3-ylamine

To a stirred solution of (3SR,4RS)-1-benzyl-3-(3-chloro-phenyl)-4-nitro-pyrrolidine (6.30 g, 19.8 mmol) in EtOAc (150 ml) was added portion wise SnCl$_2$.2H$_2$O (22.43 g, 99 mmol). The reaction mixture was then heated at reflux for 4 hours, cooled down to RT and a saturated aqueous solution of NaHCO$_3$ (500 ml) was added. The salts were filtered off and the product extracted with EtOAc. The organic phases were then dried over Na$_2$SO$_4$, and concentration under vacuum. A column chromatography (CH$_2$Cl$_2$/MeOH 95/5) gave 4.47 g (78%) of the title compound as a light yellow oil. ES-MS m/e: 287.0 (M+H$^+$).

c) [(3RS,4SR)-1-Benzyl-4-(3-chloro-phenyl)-pyrrolidin-3-yl]-methyl-amine

To a solution of (3RS,4SR)-1-benzyl-4-(3-chloro-phenyl)-pyrrolidin-3-ylamine (4.47 g, 16.0 mmol) in THF (50 ml) was added a solution of K$_2$CO$_3$ (4.31 g, 31 mmol) in H$_2$O (35 ml). After 10 minutes, ethyl chloroformate (2.97 ml, 31 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (10 ml) and a solution of borane in THF (1M) was added (62 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et$_2$O (50 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 2.68 g (57%) of the title compound as a colorless oil. ES-MS m/e: 301.2 (M+H$^+$).

d) [(3RS,4SR)-1-Benzyl-4-(3-chloro-phenyl)-pyrrolidin-3-yl]-(3-fluoro-4-trifluoromethyl-benzyl)-methyl-amine To a stirred solution of [(3RS,4SR)-1-benzyl-4-(3-chloro-phenyl)-pyrrolidin-3-yl]-methyl-amine (2.20 g, 7.31 mmol) in THF (70 ml) was added 4-bromomethyl-2-fluoro-1-trifluoromethyl-benzene (2.25 g, 8.75 mmol) and Et$_3$N (1.21 ml, 8.75 mmol). The reaction mixture was stirred overnight at 40° C., concentrated under vacuo, diluted with EtOAc, washed with H$_2$O. The organic phase was dried over Na$_2$SO$_4$ and the product purified by flash chromatography (SiO$_2$, EtOAc/Heptane 1:3) to afford 2.0 g (57%) of the title compound as a colorless oil.

e) [(3RS,4SR)-4-(3-Chloro-phenyl)-pyrrolidin-3-yl]-(3-fluoro-4-trifluoromethyl-benzyl)-methyl-amine To a stirred solution of [(3RS,4SR)-1-benzyl-4-(3-chloro-phenyl)-pyrrolidin-3-yl]-(3-fluoro-4-trifluoromethyl-benzyl)-methyl-amine (2.0 g, 4.19 mmol) in CH$_3$CN (28 ml) at RT, was added 2,2,2-trichloroethyl chloroformate (0.85 ml, 6.3 mmol). The reaction mixture was stirred at RT for 3 hours, concentrated under vacuo. The residue was dissolved in AcOH (25 ml) and zinc dust (800 mg) was added portion wise over 3 hours. The solvent was evaporated, the residue diluted in EtOAc and the organic phase was washed with an aqueous solution of NaHCO$_3$. The organic phase was dried over Na$_2$SO$_4$, concentrated under vacuo to afford 0.90 g (44%) of the tile compound as a light brown oil. ES-MS m/e: 387.2 (M+H$^+$).

Pyrrolidine VIII-5

[(3RS,4SR)-4-(3-Chloro-phenyl)-pyrrolidin-3-yl]-methyl-(4-trifluoromethyl-benzyl)-amine

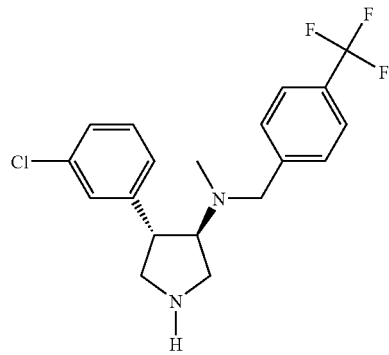

a) [(3RS,4SR)-1-Benzyl-4-(3-chloro-phenyl)-pyrrolidin-3-yl]-methyl-(4-trifluoromethyl-benzyl)-amine To a stirred solution of [(3RS,4SR)-1-benzyl-4-(3-chloro-phenyl)-pyrrolidin-3-yl]-methyl-amine (0.46 g, 1.59 mmol) in THF (15 ml) was added 1-bromomethyl-4-trifluoromethyl-benzene (0.44 g, 1.86 mmol) and Et₃N (0.155 ml, 1.59 mmol). The reaction mixture was stirred overnight at RT and concentrated under vacuo. The product purified by flash chromatography (SiO₂, EtOAc/Heptane 1:4) to afford 500 mg (71%) of the title compound as a colorless oil. ES-MS m/e: 459.3 (M+H⁺).

b) [(3RS,4SR)-4-(3-chloro-phenyl)-pyrrolidin-3-yl]-methyl-(4-trifluoromethyl-benzyl)-amine To a stirred solution of [(3RS,4SR)-1-benzyl-4-(3-chloro-phenyl)-pyrrolidin-3-yl]-methyl-(4-trifluoromethyl-benzyl)-amine (500 mg, 1.09 mmol) in CH₃CN (7 ml) at RT, was added 2,2,2-trichloroethyl chloroformate (0.22 ml, 1.63 mmol). The reaction mixture was stirred at RT for 3 hours, concentrated under vacuo. The residue was dissolved in AcOH (5 ml) and zinc dust (200 mg) was added portion wise over 1 hours. The solvent was evaporated, the residue diluted in EtOAc and the organic phase was washed with an aqueous solution of NaHCO₃. The organic phase was dried over Na₂SO₄ and concentrated under vacuo. The product was purified by column chromatography (CH₂Cl₂/MeOH: 9/1) to afford 305 mg (76%) of the tile compound as a colorless oil. ES-MS m/e: 369.2 (M+H⁺).

Process for Preparation of Pyrrolidine Intermediates of Formula XII

Pyrrolidine XII-1

(4-Methanesulfonyl-piperazin-1-yl)-((3RS,4SR)-3-methylamino-4-phenyl-pyrrolidin-1-yl)-methanone

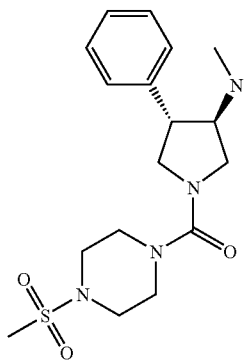

a) (3RS,4SR)-1-Benzyl-3-nitro-4-phenyl-pyrrolidine

A solution of N-(methoxymethyl)-N-(phenylmethyl)-N-(trimethylsilyl)methylamine (0.50 g, 2.02 mmol) in CH₂Cl₂ (15 ml) was added drop wise, over a 30 minutes period, to a stirred solution of ((E)-2-nitro-vinyl)-benzene (0.30 g, 2.02 mmol) and trifluoroacetic acid (0.17 ml, 0.2 mmol) in CH₂Cl₂ (10 ml) at 0° C. The ice bath was removed, and the solution was stirred at 25° C. for an additional 48 h. It was then concentrated and purification by flash chromatography (SiO₂, EtOAc/H 1:6) afforded 0.38 g (68%) of the title compound as a colorless oil. ES-MS m/e: 283 (M+H⁺).

b) (3RS,4SR)-1-Benzyl-4-phenyl-pyrrolidin-3-ylamine

To a stirred solution of (3RS,4SR)-1-benzyl-3-nitro-4-phenyl-pyrrolidine (1.0 g, 3.54 mmol) in EtOAc (50 ml) was added in one portion SnCl₂.2H₂O (3.99 g, 17.70 mmol). The reaction mixture was then heated at reflux for 2 hours, cooled down to RT and a saturated aqueous solution of NaHCO₃ (100 ml) was added. The salts were filtered off and the product extracted with EtOAc. The organic phases were then dried over Na₂SO₄, and concentration under vacuum gave 0.72 g (80%) of (3RS,4SR)-1-benzyl-4-phenyl-pyrrolidin-3-ylamine as a light yellow oil. The product was then used in the next step without further purification.

c) ((3RS,4SR)-1-Benzyl-4-phenyl-pyrrolidin-3-yl)-methyl-amine

To a solution of (3RS,4SR)-1-benzyl-4-phenyl-pyrrolidin-3-ylamine (0.25 g, 1.0 mmol) in THF (5 ml) was added a solution of K₂CO₃ (0.25 g, 1.8 mmol) in H₂O (2 ml). After 10 minutes, ethyl chloroformate (0.119 g, 1.1 mmol) was added and stirring was continued at RT for an additional 4 h. The intermediate carbamate was then extracted with Et₂O, dried over Na₂SO₄ and concentrated under vacuo to give viscous oil. The oil was taken up in THF (5 ml) and a solution of borane in THF (1M) was added (3.5 ml). The reaction mixture was then heated at 65° C. over night, cooled to RT and carefully quenched with conc. HCl (0.5 ml). The mixture was then heated at 80° C. for 2 h, cooled to RT, concentrated under vacuo, diluted with Et₂O (20 ml) and neutralized with an aqueous solution of NaHCO₃. The organic phases were dried over Na₂SO₄ and the product purified by flash chromatography (SiO₂, CH₂Cl₂/MeOH 9:1) to afford 0.21 g (82%) of rac-((3S,4R)-1-benzyl-4-phenyl-pyrrolidin-3-yl)-methyl-amine as a colorless oil.

d) ((3RS,4SR)-1-Benzyl-4-phenyl-pyrrolidin-3-yl)-methyl-carbamic acid tert-butyl ester To a stirred solution of [(3RS,4SR)-1-benzyl-4-phenyl)-pyrrolidin-3-yl]-methyl-amine (2.00 g, 7.55 mmol) in CH₂Cl₂ (20 ml) was added Et₃N (1.80 ml, 15.1 mmol), DMAP (81 mg, 0.66 mmol) and (Boc)₂O (1.75 g, 8.02 mmol). After one hour at RT, the organic phase was washed with H₂O, then dried over Na₂SO₄. Column chromatography (Heptane/EtOAc: 3/1) afforded 2.04 g (74%) of the title compound as a yellow oil.

e) Methyl-((3RS,4SR)-4-phenyl-pyrrolidin-3-yl)-carbamic acid tert-butyl ester To a stirred solution of ((3RS,4SR)-1-Benzyl-4-phenyl-pyrrolidin-3-yl)-methyl-carbamic acid tert-butyl ester (2.03 g, 5.56 mmol) in MeOH (20 ml) at RT, was added ammonium formate (1.60 g, 25.4 mmol) and palladium on charcoal (0.40 g, 10%) The reaction mixture was stirred for 2 hours, filtrate on celite and concentrated under vacuo. The residue was purified by column chromatography (CH₂Cl₂/MeOH, 9/1) to give 0.57 g (41%) of the title product as a waxy solid.

ES-MS m/e: 277.1 (M+H⁺).

e) [(3RS,4SR)-1-(4-Methanesulfonyl-piperazine-1-carbonyl)-4-phenyl-pyrrolidin-3-yl]-methyl-carbamic acid tert-butyl ester Using the general procedure II for the preparation of urea, 640 mg of the title compound was produce from methyl-((3RS,4SR)-4-phenyl-pyrrolidin-3-yl)-carbamic acid tert-butyl ester and 4-methanesulfonyl-piperazine-1-carbonyl chloride as a white solid. ES-MS m/e: 467.3 (M+H$^+$).

4-Methanesulfonyl-piperazine-1-carbonyl chloride

To a stirred solution of carbonic acid ditrichloromethyl ester (triphosgene) (1.81 g, 6.09 mmol) in CH$_2$Cl$_2$ (30 mL) at 0° C., was added a solution of 1-methanesulfonyl-piperazine (2.0 g, 12.2 mmol) and pyridine (1.08 mL, 13.4 mmol) in CH$_2$Cl$_2$ (5 mL) over 30 minutes. The temperature was raised to RT, and stirring was continued over night. The organic phase was washed with H$_2$O, dried over Na$_2$SO$_4$. Purification by flash chromatography (SiO$_2$, EtOAc) yielded 2.20 g (79%) of the title compound as white solid.

f) (4-Methanesulfonyl-piperazin-1-yl)-((3RS,4SR)-3-methylamino-4-phenyl-pyrrolidin-1-yl)-methanone To a stirred solution of [(3RS,4SR)-1-(4-Methanesulfonyl-piperazine-1-carbonyl)-4-phenyl-pyrrolidin-3-yl]-methyl-carbamic acid tert-butyl ester (640 mg, 1.37 mmol) in CH$_2$Cl$_2$ (10 ml) was added TFA (2 ml). The reaction mixture was stirred at RT for 2 hours, aqueous NaHCO$_3$ was added until pH=8 and the product was extracted with CH$_2$Cl$_2$. The combined organic phase were dried over Na$_2$SO$_4$. Concentration under vacuo gave 500 mg (99%) of the title product as a white solid. ES-MS m/e: 367.1 (M+H$^+$).

Pyrrolidine XII-2

[(3SR,4RS)-3-(4-Chloro-phenyl)-4-methylamino-pyrrolidin-1-yl]-(4-methanesulfonyl-piperazin-1-yl)-methanone

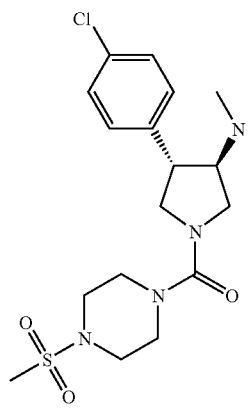

a) (3SR,4SR)-1-Benzyl-3-(4-chloro-phenyl)-4-nitro-pyrrolidine

A solution of N-(methoxymethyl)-N-(phenylmethyl)-N-(trimethylsilyl)methylamine (6.70 g, 28.2 mmol) in CH$_2$Cl$_2$ (100 ml) was added drop wise, over a 30 minutes period, to a stirred solution of 1-chloro-4-((E)-2-nitro-vinyl)-benzene (4.97 g, 27.1 mmol) and trifluoroacetic acid (0.31 g, 2.7 mmol) in CH$_2$Cl$_2$ (150 ml) at 0° C. The ice bath was removed, and the solution was stirred at 25° C. for an additional 48 h. It was then concentrated and purification by flash chromatography (SiO$_2$, EtOAc/H 1:4) afforded 6.75 g (79%) of the title compound as a colorless oil.

b) (3RS,4SR)-1-Benzyl-4-(4-chloro-phenyl)-pyrrolidin-3-ylamine

Titanium (IV) chloride (0.36 g, 1.89 mmol) was added drop wise to a suspension of zinc powder (0.25 g, 3.78 mmol) in THF (3 ml). This solution was heated at 68° C. for one hour, then cooled to RT before (3SR,4RS)-1-benzyl-3-(4-chloro-phenyl)-4-nitro-pyrrolidine (0.20 g, 0.63 mmol) in THF (2 ml) was added. The reaction mixture was then stirred at reflux over night. The reaction was cooled to RT, diluted with 300 ml of Et$_2$O, washed with an aqueous solution of NaHCO$_3$ and the organic phases were dried over Na$_2$SO$_4$. Flash chromatography (SiO$_2$, CH$_2$Cl$_2$/MeOH, 9:1) yielded 0.10 g (57%) of (3RS,4SR)-1-benzyl-4-(4-chloro-phenyl)-pyrrolidin-3-ylamine as a light yellow oil.

c) [(3RS,4SR)-1-Benzyl-4-(4-chloro-phenyl)-pyrrolidin-3-yl]-methyl-amine

To a solution of (3RS,4SR)-1-benzyl-4-(4-chloro-phenyl)-pyrrolidin-3-ylamine (1.86 g, 6.51 mmol) in THF (20 ml) was added a solution of K$_2$CO$_3$ (1.80 g, 13.02 mmol) in H$_2$O (15 ml). After 10 minutes, ethyl chloroformate (0.68 ml, 7.16 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (20 ml) and a solution of borane in THF (1M) was added (26 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et$_2$O (100 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 1.51 g (77%) of rac-[(3S,4R)-1-benzyl-4-(4-chloro-phenyl)-pyrrolidin-3-yl]-methyl-amine as a colorless oil.

d) [(3RS,4SR)-1-Benzyl-4-(4-chloro-phenyl)-pyrrolidin-3-yl]-methyl-carbamic acid tert-butyl ester To a stirred solution of [(3RS,4SR)-1-benzyl-4-(4-chloro-phenyl)-pyrrolidin-3-yl]-methyl-amine (2.75 g, 9.14 mmol) in CH$_2$Cl$_2$ (25 ml) was added Et$_3$N (2.50 ml, 18.2 mmol), DMAP (112 mg, 0.91 mmol) and (Boc)$_2$O (2.39 g, 10.95 mmol). After one hour at RT, the organic phase was washed with H$_2$O, then dried over Na$_2$SO$_4$. Column chromatography (Heptane/EtOAc: 3/1) afforded 2.60 g (71%) of the title compound as a yellow oil. ES-MS m/e: 401.3 (M+H$^+$).

e) [(3RS,4SR)-4-(4-Chloro-phenyl)-pyrrolidin-3-yl]-methyl-carbamic acid tert-butyl ester To a stirred solution of [(3RS,4SR)-1-benzyl-4-(4-chloro-phenyl)-pyrrolidin-3-yl]-methyl-carbamic acid tert-butyl ester (1.30 g, 3.20 mmol) in toluene (30 ml) at RT, was added 1-chloroethyl chloroformate (0.53 ml, 4.80 mmol). The reaction mixture was stirred at 90° C. overnight and concentrated under vacuo. The residue was dissolved in MeOH (30 ml) and the reaction mixture was heated at 80° C. for 2 hours. The solvent was evaporated and the crude product was directly used in the next step without further purification.

e) [(3RS,4SR)-4-(4-Chloro-phenyl)-1-(4-methanesulfonyl-piperazine-1-carbonyl)-pyrrolidin-3-yl]-methyl-carbamic acid tert-butyl ester Using the general procedure II for the preparation of urea, 871 mg of the title compound was produce from 765 mg of [(3RS,4SR)-4-(4-chloro-phenyl)-pyrrolidin-3-yl]-methyl-carbamic acid tert-butyl ester and 4-methanesulfonyl-piperazine-1-carbonyl chloride as a white solid. ES-MS m/e: 501.43 (M+H$^+$).

f) [(3SR,4RS)-3-(4-Chloro-phenyl)-4-methylamino-pyrrolidin-1-yl]-(4-methanesulfonyl-piperazin-1-yl)-methanone To a stirred solution of [(3RS,4SR)-4-(4-Chloro-phenyl)-1-(4-methanesulfonyl-piperazine-1-carbonyl)-pyrrolidin-3-yl]-methyl-carbamic acid tert-butyl ester (860 mg, 1.72 mmol) in CH$_2$Cl$_2$ (8 ml) was added TFA (2 ml). The reaction mixture was stirred at RT for 2 hours, aqueous NaHCO$_3$ was added until pH=8 and the product was extracted with CH$_2$Cl$_2$. The combined organic phase were dried over Na$_2$SO$_4$. Concentration under vacuo gave 680 mg (98%) of the title product as a white solid. ES-MS m/e: 401.3 (M+H$^+$).

Pyrrolidine XII-3

[(3SR,4RS)-3-(3,4-Dichloro-phenyl)-4-methylamino-pyrrolidin-1-yl]-(4-methanesulfonyl-piperazin-1-yl)-methanone

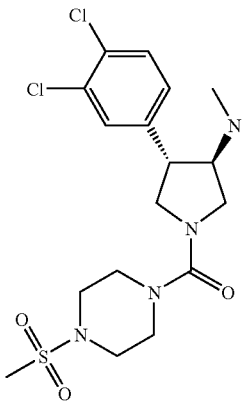

[(3RS,4SR)-1-Benzyl-4-(3,4-dichloro-phenyl)-pyrrolidin-3-yl]-methyl-carbamic acid tert-butyl ester To a stirred solution of [(3RS,4SR)-1-benzyl-4-(3,4-dichloro-phenyl)-pyrrolidin-3-yl]-methyl-amine (1.00 g, 2.98 mmol) in CH$_2$Cl$_2$ (10 ml) was added Et$_3$N (0.83 ml, 5.96 mmol), DMAP (73 mg, 0.59 mmol) and (Boc)$_2$O (1.43 g, 6.55 mmol). After one hour at RT, the organic phase was washed with H$_2$O, then dried over Na$_2$SO$_4$. Column chromatography (Heptane/EtOAc: 3/1) afforded 0.93 g (71%) of the title compound as a yellow oil. ES-MS m/e: 435.3 (M+H$^+$).

b) [(3RS,4SR)-4-(3,4-Dichloro-phenyl)-pyrrolidin-3-yl]-methyl-carbamic acid tert-butyl ester To a stirred solution of [(3RS,4SR)-1-benzyl-4-(3,4-dichloro-phenyl)-pyrrolidin-3-yl]-methyl-carbamic acid tert-butyl ester (928 mg, 2.13 mmol) in CH$_3$CN (10 ml) at RT, was added 2,2,2-trichloroethyl chloroformate (0.45 ml, 2.13 mmol). The reaction mixture was stirred at RT for 3 hours, concentrated under vacuo. The residue was dissolved in AcOH (5 ml) and zinc dust (400 mg) was added portion wise over 1 hours. The solvent was evaporated, the residue diluted in EtOAc and the organic phase was washed with an aqueous solution of NaHCO$_3$. The organic phase was dried over Na$_2$SO$_4$ and concentrated under vacuo to afford 415 mg (98%) of the tile compound as a light yellow oil. ES-MS m/e: 345.2 (m+H$^+$), c) [(3RS,4SR)-4-(3,4-Dichloro-phenyl)-1-(4-methanesulfonyl-piperazine-1-carbonyl)-pyrrolidin-3-yl]-methyl-carbamic acid tert-butyl ester Using the general procedure II for the preparation of urea, 133 mg of the title compound was produce from [(3RS,4SR)-4-(3,4-dichloro-phenyl)-pyrrolidin-3-yl]-methyl-carbamic acid tert-butyl ester and 4-methanesulfonyl-piperazine-1-carbonyl chloride as a white solid. ES-MS m/e: 535.1 (M+H$^+$).

d) [(3SR,4RS)-3-(3,4-Dichloro-phenyl)-4-methylamino-pyrrolidin-1-yl]-(4-methanesulfonyl-piperazin-1-yl)-methanone To a stirred solution of [(3RS,4SR)-4-(3,4-dichloro-phenyl)-1-(4-methanesulfonyl-piperazine-1-carbonyl)-pyrrolidin-3-yl]-methyl-carbamic acid tert-butyl ester (130 mg, 0.24 mmol) in CH$_2$Cl$_2$ (5 ml) was added TFA (1 ml). The reaction mixture was stirred at RT for 2 hours, aqueous NaHCO$_3$ was added until pH=8 and the product was extracted with CH$_2$Cl$_2$. The combined organic phase were dried over Na$_2$SO$_4$. Concentration under vacuo gave 100 mg (93%) of the title product as a light yellow oil. ES-MS m/e: 435.8 (M+H$^+$).

Pyrrolidine XII-4

[(3SR,4RS)-3-(3,4-Dichloro-phenyl)-4-methylamino-pyrrolidin-1-yl]-[1-(1-methyl-cyclopropanecarbonyl)-piperidin-4-yl]-methanone

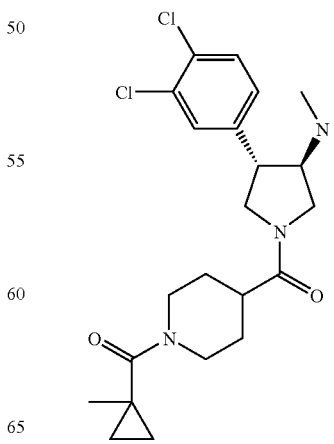

a) {(3RS,4SR)-4-(3,4-Dichloro-phenyl)-1-[1-(1-methyl-cyclopropanecarbonyl)-piperidine-4-carbonyl]-pyrrolidin-3-yl}-methyl-carbamic acid tert-butyl ester Using the general procedure I for the preparation of amide, 3.06 g of the title compound was produce from [(3RS,4SR)-4-(3,4-dichloro-phenyl)-pyrrolidin-3-yl]-methyl-carbamic acid tert-butyl ester and 1-(1-Methyl-cyclopropanecarbonyl)-piperidine-4-carboxylic acid as a light brown foam. ES-MS m/e: 538.3 (M+H$^+$).

1-(1-Methyl-cyclopropanecarbonyl)-piperidine-4-carboxylic acid

First step: Using the general procedure I for the preparation of amide, 2.60 g of 1-(1-methyl-cyclopropanecarbonyl)-piperidine-4-carboxylic acid ethyl ester was prepared from 1.89 g of piperidine-4-carboxylic acid ethyl ester and 1.40 g of 1-methyl-cyclopropanecarbonyl acid as a light yellow oil. ES-MS m/e: 240.3 (M+H$^+$). Second step: To a stirred solution of 1-(1-methyl-cyclopropanecarbonyl)-piperidine-4-carboxylic acid ethyl ester (2.60 g, 0.011 mmol) in THF, EtOH, H$_2$O (50 ml, 1/1/1) was added LiOH.H$_2$O (686 mg, 16.3 mmol). After two hours at RT, the reaction mixture was concentrated under vacuo. The crude residue was diluted in CH$_2$Cl$_2$ and aqueous HCl (1N) was added until pH=2. The organic phase was collected, dried over Na$_2$SO$_4$ and concentrated under vacuo to afforded 1.98 g (86%) of the title product as a white powder. ES-MS m/e: 212.1 (M+H$^+$).

b) [(3SR,4RS)-3-(3,4-Dichloro-phenyl)-4-methylamino-pyrrolidin-1-yl]-[1-(1-methyl-cyclopropanecarbonyl)-piperidin-4-yl]-methanone To a stirred solution of {(3RS,4SR)-4-(3,4-dichloro-phenyl)-1-[1-(1-methyl-cyclopropanecarbonyl)-piperidine-4-carbonyl]-pyrrolidin-3-yl}-methyl-carbamic acid tert-butyl ester (3.02 g, 5.61 mmol) in CH$_2$Cl$_2$ (30 ml) was added TFA (4.3 ml). The reaction mixture was stirred at RT for 20 hours, aqueous NaHCO$_3$ was added until pH=8 and the product was extracted with CH$_2$Cl$_2$. The combined organic phase were dried over Na$_2$SO$_4$. The product was purified by column chromatography (SiO2, H/EtOAc/MeOH, 50:50:0 to 0:90:10) to afford 1.79 g (73%) of the title product as a light brown oil. ES-MS m/e: 338.3 (M+H$^+$).

Process for Preparation of Pyrrolidine Intermediates of Formula XIII

Pyrrolidine XIII-1

(3SR,4RS)-3-(3,4-Dichloro-phenyl)-4-[(3-fluoro-4-trifluoromethyl-benzyl)-methyl-amino]-pyrrolidine-1-carbonyl chloride

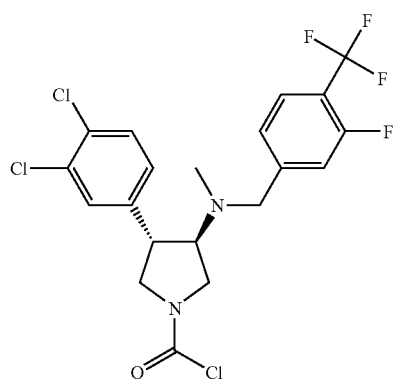

To a stirred solution of carbonic acid ditrichloromethyl ester (triphosgene) (37 mg, 0.125 mmol) in CH$_2$Cl$_2$ (10 ml) at −78° C., was added a solution of [(3RS,4SR)-4-(3,4-Dichloro-phenyl)-pyrrolidin-3-yl]-(3-fluoro-4-trifluoromethyl-benzyl)-methyl-amine (Intermediate VIII-1), (130 mg, 0.31 mmol) and pyridine (0.05 ml, 0.68 mmol) in CH$_2$Cl$_2$ (5 ml) over 30 minutes. The temperature was raised to RT, and stirring was continued for 2 hours. The organic phase was washed with H$_2$O, dried over Na$_2$SO$_4$. Purification by flash chromatography (SiO$_2$, EtOAc/Hx 1:2) yielded 83 mg (55%) of the title compound as a light yellow oil.

ES-MS m/e: 483.0 (M+H$^+$).

Process for Preparation of Pyrrolidine Intermediates of Formula XIV

Pyrrolidine XIV-1

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone

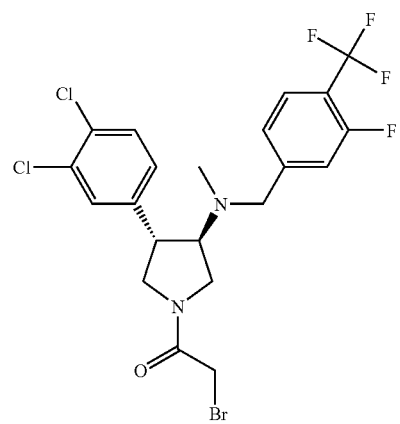

To a stirred solution of bromo-acetyl chloride (0.146 ml, 1.75 mmol) in THF (15 ml) at RT was added over 1 hour a solution of [(3RS,4SR)-4-(3,4-dichloro-phenyl)-pyrrolidin-3-yl]-(3-fluoro-4-trifluoromethyl-benzyl)-methyl-amine (Intermediate VIII-1, 0.70 g, 1.66 mmol) and triethyl amine (0.25 ml, 1.83 mmol) in THF (10 mL). The reaction was stirred over night, quenched by addition of an aqueous solution of NaHCO$_3$, and the product extracted with EtOAC. Purification by flash chromatography (SiO$_2$, EtOAc/Hx 1:1) yielded 0.63 g (70%) of the title compound as a white solid. ES-MS m/e: 542.6 (M+H$^+$).

Process for Preparation of Pyrrolidine Intermediates of Formula XV

Pyrrolidine XV-1

5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one

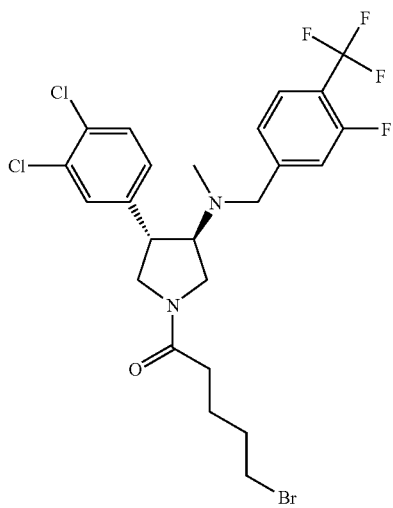

To a stirred solution of 5-bromo-pentanoyl chloride (0.167 ml, 1.25 mmol) in THF (10 ml) at RT was added over 1 hour a solution of [(3RS,4SR)-4-(3,4-dichloro-phenyl)-pyrrolidin-3-yl]-(3-fluoro-4-trifluoromethyl-benzyl)-methyl-amine (Intermediate VIII-1, 0.50 g, 1.19 mmol) and triethyl amine (0.18 ml, 1.30 mmol) in THF (5 mL). The reaction was stirred over night, quenched by addition of an aqueous solution of NaHCO$_3$, and the product extracted with EtOAC. Purification by flash chromatography (SiO$_2$, EtOAc/Hx 1:1) yielded 0.58 g (83%) of the title compound as a white solid. ES-MS m/e: 584.4 (M+H$^+$).

Process for Preparation of Pyrrolidine Intermediates of Formula XVI

Pyrrolidine XVI-1

(3SR,4RS)-3-(3,4-Dichloro-phenyl)-4-[(3-fluoro-4-trifluoromethyl-benzyl)-methyl-amino]-pyrrolidine-1-carboxylic acid 3-chloro-propyl ester

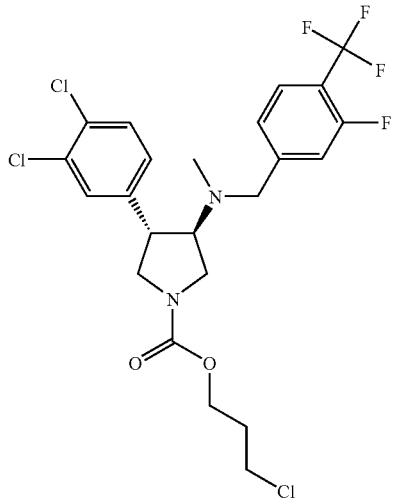

To a stirred solution of 3-chloropropyl chloroformate (0.058 ml, 0.47 mmol) in THF (5 ml) at RT was added over 1 hour a solution of [(3RS,4SR)-4-(3,4-Dichloro-phenyl)-pyrrolidin-3-yl]-(3-fluoro-4-trifluoromethyl-benzyl)-methyl-amine (Intermediate VIII-1, 0.187 g, 0.44 mmol) and triethyl amine (0.068 ml, 0.48 mmol) in THF (2 mL). The reaction was stirred over night, quenched by addition of an aqueous solution of NaHCO$_3$, and the product extracted with EtOAC. The organic phases were concentrated under vacuo to yielded 0.25 g (99%) of the title compound as a light yellow oil. The product was used in the next steps without further purification. ES-MS m/e: 542.7 (M+H$^+$).

Example 1

{(3RS,4SR)-3-[(3,5-Bis-trifluoromethyl-benzyl)-methyl-amino]-4-phenyl-pyrrolidin-1-yl}-(4-methanesulfonyl-piperazin-1-yl)-methanone

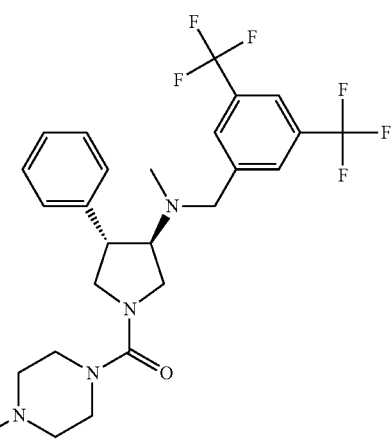

Alkylation according to general procedure IV:

Pyrrolidine intermediate: (4-Methanesulfonyl-piperazin-1-yl)-((3RS,4SR)-3-methylamino-4-phenyl-pyrrolidin-1-yl)-methanone (XII-1), Electrophile: 1-Bromomethyl-3,5-bis-trifluoromethyl-benzene (commercially available), ES-MS m/e: 593.4 (M+H$^+$).

Example 2

{(3RS,4SR)-3-[(3-Chloro-benzyl)-methyl-amino]-4-phenyl-pyrrolidin-1-yl}-(4-methanesulfonyl-piperazin-1-yl)-methanone

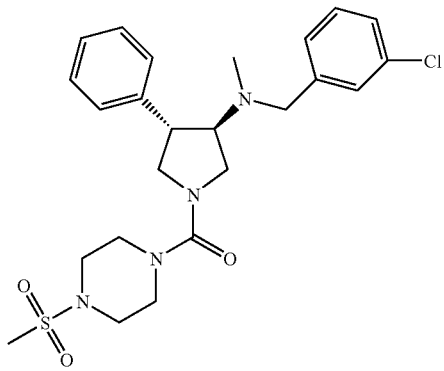

Alkylation according to general procedure IV:

Pyrrolidine intermediate: (4-Methanesulfonyl-piperazin-1-yl)-((3RS,4SR)-3-methylamino-4-phenyl-pyrrolidin-1-yl)-methanone (XII-1), Electrophile: 1-Bromomethyl-3-chloro-benzene (commercially available), ES-MS m/e: 491.3 (M+H$^+$).

Example 3

{(3RS,4SR)-3-[(3,5-Dimethyl-benzyl)-methyl-amino]-4-phenyl-pyrrolidin-1-yl}-(4-methanesulfonyl-piperazin-1-yl)-methanone

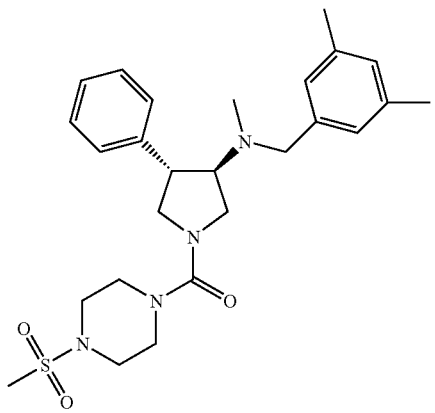

Alkylation according to general procedure IV:

Pyrrolidine intermediate: (4-Methanesulfonyl-piperazin-1-yl)-((3RS,4SR)-3-methylamino-4-phenyl-pyrrolidin-1-yl)-methanone (XII-1), Electrophile: 1-Bromomethyl-3,5-dimethyl-benzene (commercially available), ES-MS m/e: 485.4 (M+H$^+$).

Example 4

{(3RS,4SR)-3-[(3,5-Difluoro-benzyl)-methyl-amino]-4-phenyl-pyrrolidin-1-yl}-(4-methanesulfonyl-piperazin-1-yl)-methanone

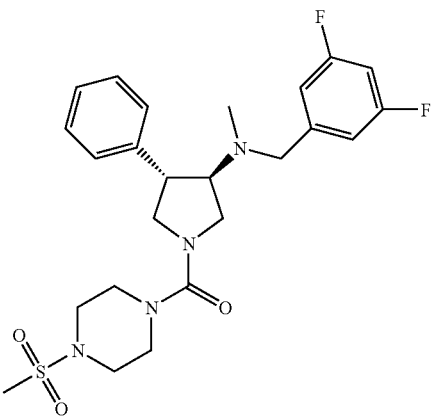

Alkylation according to general procedure IV:

Pyrrolidine intermediate: (4-Methanesulfonyl-piperazin-1-yl)-((3RS,4SR)-3-methylamino-4-phenyl-pyrrolidin-1-yl)-methanone (XII-1), Electrophile: 1-Bromomethyl-3,5-difluoro-benzene (commercially available), ES-MS m/e: 493.3 (M+H$^+$).

Example 5

{(3RS,4SR)-3-[(2-Fluoro-5-trifluoromethyl-benzyl)-methyl-amino]-4-phenyl-pyrrolidin-1-yl}-(4-methanesulfonyl-piperazin-1-yl)-methanone

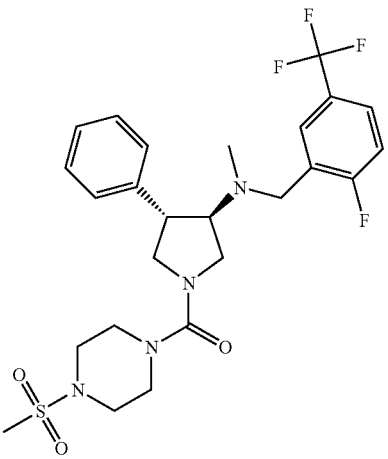

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 2-Fluoro-5-trifluoromethyl-benzaldehyde (commercially available), ES-MS m/e: 543.4 (M+H$^+$).

Example 6

{(3RS,4SR)-3-[(3,4-Dichloro-benzyl)-methyl-amino]-4-phenyl-pyrrolidin-1-yl}-(4-methanesulfonyl-piperazin-1-yl)-methanone

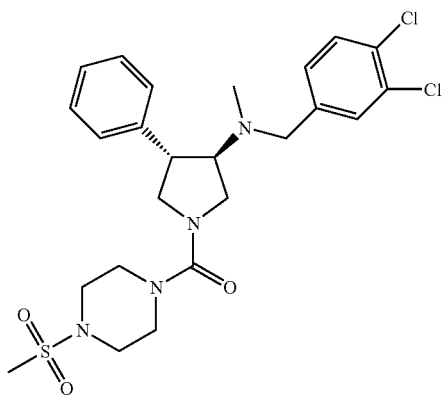

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 3,4-Dichloro-benzaldehyde (commercially available), ES-MS m/e: 525.3 (M+H$^+$).

Example 7

{(3RS,4SR)-3-[(4-Chloro-3-trifluoromethyl-benzyl)-methyl-amino]-4-phenyl-pyrrolidin-1-yl}-(4-methanesulfonyl-piperazin-1-yl)-methanone

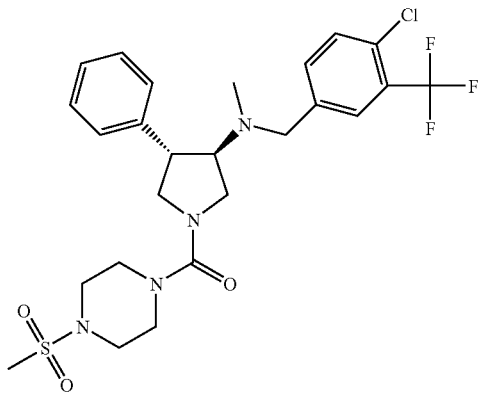

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 4-Chloro-3-trifluoromethyl-benzaldehyde (commercially available), ES-MS m/e: 593.4 (M+H$^+$).

Example 8

{(3RS,4SR)-3-[(5-Chloro-2-fluoro-benzyl)-methyl-amino]-4-phenyl-pyrrolidin-1-yl}-(4-methanesulfonyl-piperazin-1-yl)-methanone

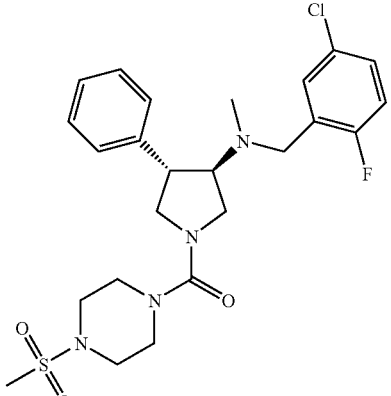

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 5-Chloro-2-fluoro-benzaldehyde (commercially available), ES-MS m/e: 543.3 (M+H$^+$).

Example 9

(4-Methanesulfonyl-piperazin-1-yl)-{(3RS,4SR)-3-[(2-methoxy-5-trifluoromethoxy-benzyl)-methyl-amino]-4-phenyl-pyrrolidin-1-yl}-methanone

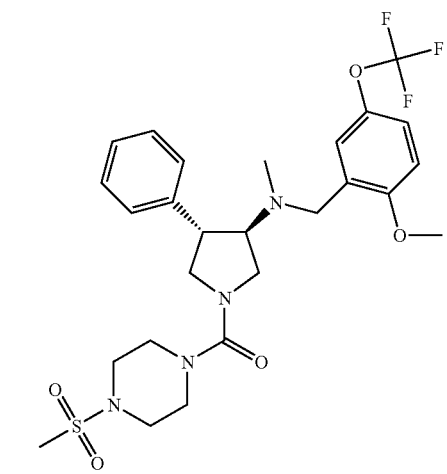

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 2-Methoxy-5-trifluoromethoxy-benzaldehyde (commercially available), ES-MS m/e: 571.3 (M+H$^+$).

Example 10

{(3RS,4SR)-3-[(4-Fluoro-3-trifluoromethyl-benzyl)-methyl-amino]-4-phenyl-pyrrolidin-1-yl}-(4-methanesulfonyl-piperazin-1-yl)-methanone

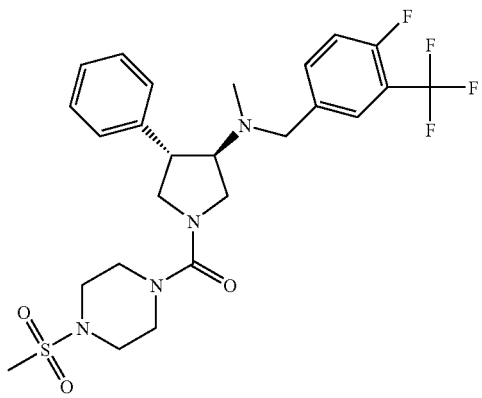

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 4-Fluoro-3-trifluoromethyl-benzaldehyde (commercially available), ES-MS m/e: 543.3 (M+H$^+$).

Example 11

{(3RS,4SR)-3-[(2-Chloro-5-trifluoromethyl-benzyl)-methyl-amino]-4-phenyl-pyrrolidin-1-yl}-(4-methanesulfonyl-piperazin-1-yl)-methanone

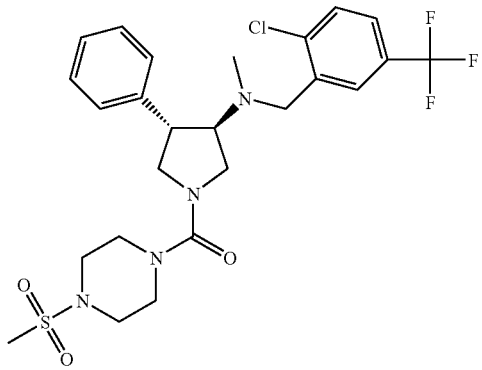

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 2-Chloro-5-trifluoromethyl-benzaldehyde (commercially available), ES-MS m/e: 559.3 (M+H$^+$).

Example 12

{(3RS,4SR)-3-[(4-Fluoro-3-methoxy-benzyl)-methyl-amino]-4-phenyl-pyrrolidin-1-yl}-(4-methanesulfonyl-piperazin-1-yl)-methanone

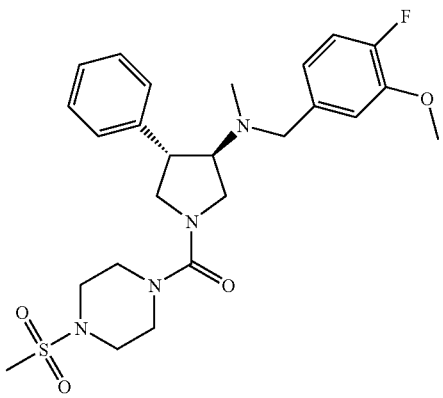

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 4-Fluoro-3-methoxy-benzaldehyde (commercially available), ES-MS m/e: 505.3 (M+H$^+$).

Example 13

(4-Methanesulfonyl-piperazin-1-yl)-{(3RS,4SR)-3-[methyl-(3-trifluoromethoxy-benzyl)-amino]-4-phenyl-pyrrolidin-1-yl}-methanone

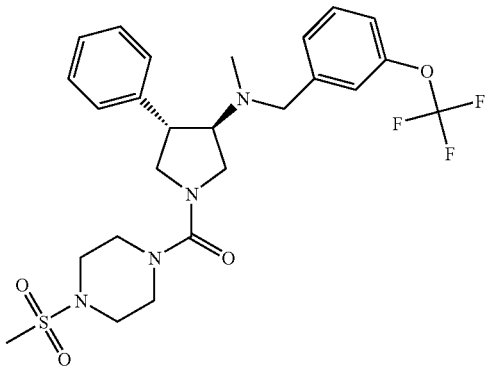

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: 3-Trifluoromethoxy-Benzaldehyde (Commercially Available), ES-MS m/e: 541.4 (M+H$^+$).

Example 14

(4-Methanesulfonyl-piperazin-1-yl)-{(3RS,4SR)-3-[methyl-(4-thiophen-2-yl-benzyl)-amino]-4-phenyl-pyrrolidin-1-yl}-methanone

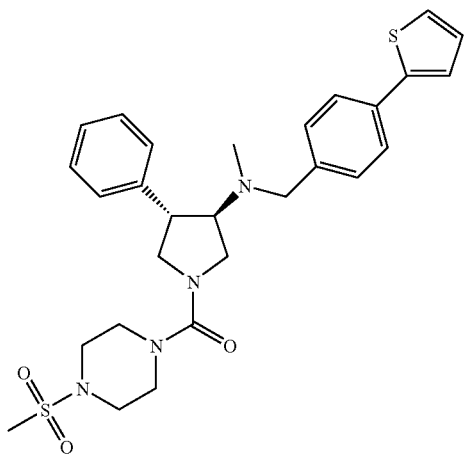

Reductive amination according to general procedure III:
Pyrrolidine intermediate: (4-Methanesulfonyl-piperazin-1-yl)-((3RS,4SR)-3-methylamino-4-phenyl-pyrrolidin-1-yl)-methanone (XII-1),
Aldehyde: 4-Thiophen-2-yl-benzaldehyde (commercially available),
ES-MS m/e: 539.4 (M+H⁺).

Example 15

{(3RS,4SR)-3-[(4-Imidazol-1-yl-benzyl)-methyl-amino]-4-phenyl-pyrrolidin-1-yl}-(4-methanesulfonyl-piperazin-1-yl)-methanone

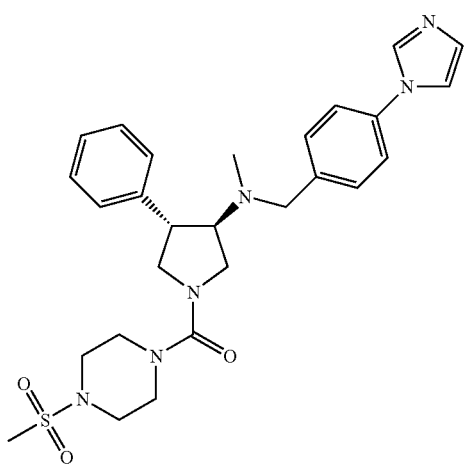

Reductive amination according to general procedure III:
Pyrrolidine intermediate: (4-Methanesulfonyl-piperazin-1-yl)-((3RS,4SR)-3-methylamino-4-phenyl-pyrrolidin-1-yl)-methanone (XII-1),
Aldehyde: 4-Imidazol-1-yl-benzaldehyde (commercially available),
ES-MS m/e: 523.5 (M+H⁺).

Example 16

{(3RS,4SR)-3-[(2-Fluoro-4-trifluoromethyl-benzyl)-methyl-amino]-4-phenyl-pyrrolidin-1-yl}-(4-methanesulfonyl-piperazin-1-yl)-methanone

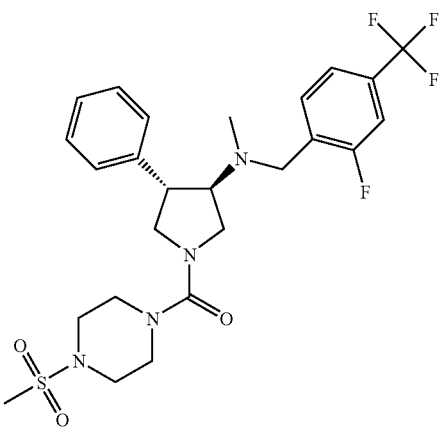

Reductive amination according to general procedure III:
Pyrrolidine intermediate: (4-Methanesulfonyl-piperazin-1-yl)-((3RS,4SR)-3-methylamino-4-phenyl-pyrrolidin-1-yl)-methanone (XII-1),
Aldehyde: 2-Fluoro-4-trifluoromethyl-benzaldehyde (commercially available),
ES-MS m/e: 543.3 (M+H⁺).

Example 17

{(3RS,4SR)-3-[(3-Fluoro-4-trifluoromethyl-benzyl)-methyl-amino]-4-phenyl-pyrrolidin-1-yl}-(4-methanesulfonyl-piperazin-1-yl)-methanone

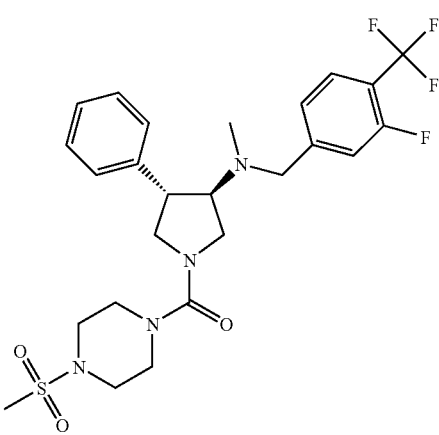

Reductive amination according to general procedure III:
Pyrrolidine intermediate: (4-Methanesulfonyl-piperazin-1-yl)-((3RS,4SR)-3-methylamino-4-phenyl-pyrrolidin-1-yl)-methanone (XII-1),
Aldehyde: 3-Fluoro-4-trifluoromethyl-benzaldehyde (commercially available),
ES-MS m/e: 543.5 (M+H⁺).

Example 18

[(3RS,4SR)-3-(Benzyl-methyl-amino)-4-phenyl-pyrrolidin-1-yl]-(4-methanesulfonyl-piperazin-1-yl)-methanone

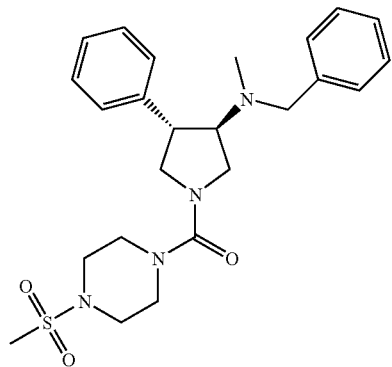

Reductive amination according to general procedure III:

Pyrrolidine intermediate: (4-Methanesulfonyl-piperazin-1-yl)-((3RS,4SR)-3-methylamino-4-phenyl-pyrrolidin-1-yl)-methanone (XII-1), Aldehyde: benzaldehyde (commercially available), ES-MS m/e: 457.5 (M+H$^+$).

Example 19

{(3SR,4RS)-3-(4-Chloro-phenyl)-4-[(3,4-dichloro-benzyl)-methyl-amino]-pyrrolidin-1-yl}-(4-methane-sulfonyl-piperazin-1-yl)-methanone

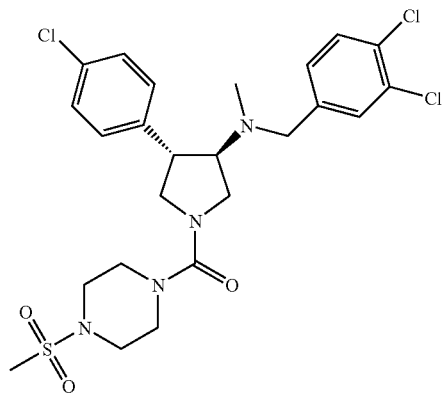

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 3,4-Dichloro-benzaldehyde (commercially available), ES-MS m/e: 561.1 (M+H$^+$).

Example 20

{(3SR,4RS)-3-(4-Chloro-phenyl)-4-[(4-chloro-3-trifluoromethyl-benzyl)-methyl-amino]-pyrrolidin-1-yl}-(4-methanesulfonyl-piperazin-1-yl)-methanone

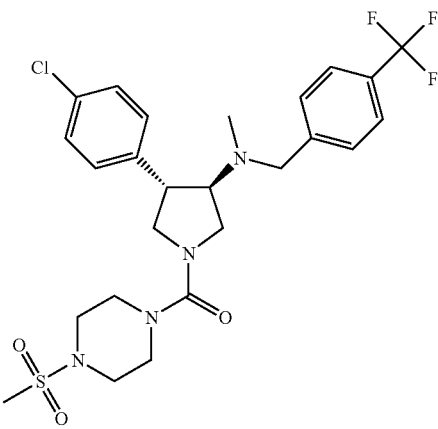

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 4-Chloro-3-trifluoromethyl-benzaldehyde (commercially available), ES-MS m/e: 593.81 (M+H$^+$).

Example 21

{(3SR,4RS)-3-(4-Chloro-phenyl)-4-[methyl-(4-trifluoromethyl-benzyl)-amino]-pyrrolidin-1-yl}-(4-methanesulfonyl-piperazin-1-yl)-methanone

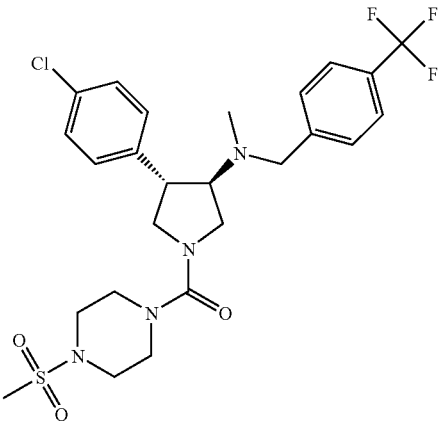

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 4-Trifluoromethyl-benzaldehyde (commercially available), ES-MS m/e: 559.3 (M+H$^+$).

Example 22

{(3SR,4RS)-3-(4-Chloro-phenyl)-4-[(4-fluoro-benzyl)-methyl-amino]-pyrrolidin-1-yl}-(4-methanesulfonyl-piperazin-1-yl)-methanone

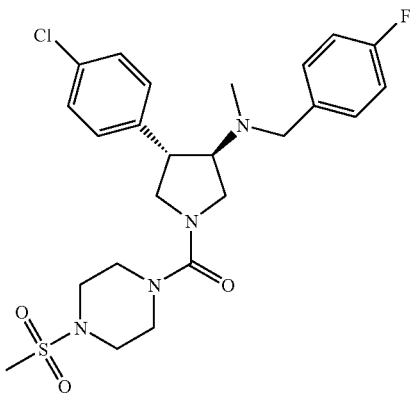

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 4-Fluoro-benzaldehyde (commercially available), ES-MS m/e: 509.2 (M+H$^+$).

Example 23

[(3RS,4SR)-3-[(4-Chloro-benzyl)-methyl-amino]-4-(4-chloro-phenyl)-pyrrolidin-1-yl]-(4-methanesulfonyl-piperazin-1-yl)-methanone

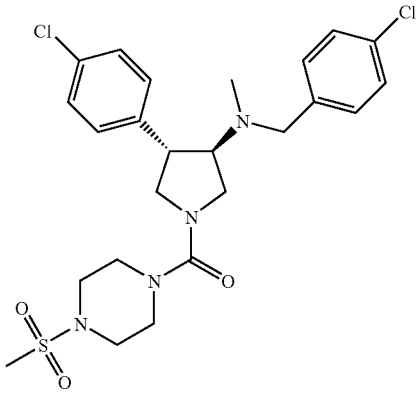

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 4-chloro-benzaldehyde (commercially available), ES-MS m/e: 525.3 (M+H$^+$).

Example 24

{(3SR,4RS)-3-(4-Chloro-phenyl)-4-[methyl-(4-trifluoromethoxy-benzyl)-amino]-pyrrolidin-1-yl}-(4-methanesulfonyl-piperazin-1-yl)-methanone

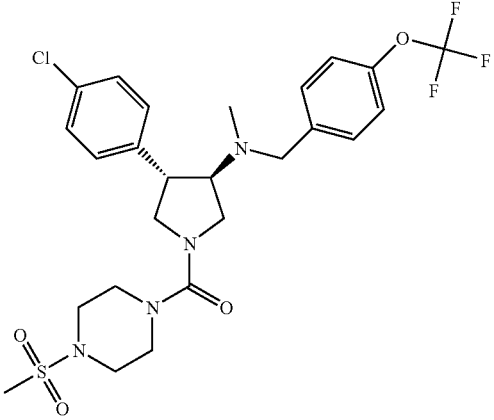

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 4-Trifluoromethoxy-benzaldehyde (commercially available), ES-MS m/e: 575.3 (M+H$^+$).

Example 25

{(3SR,4RS)-3-(4-Chloro-phenyl)-4-[(4-difluoromethoxy-benzyl)-methyl-amino]-pyrrolidin-1-yl}-(4-methanesulfonyl-piperazin-1-yl)-methanone

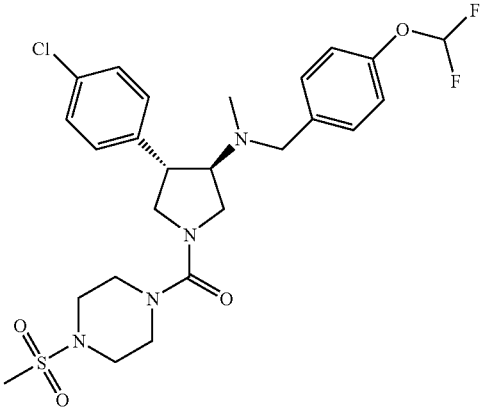

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 4-Difluoromethoxy-benzaldehyde (commercially available), ES-MS m/e: 557.1 (M+H$^+$).

Example 26

4-({[(3RS,4SR)-4-(4-Chloro-phenyl)-1-(4-methane-sulfonyl-piperazine-1-carbonyl)-pyrrolidin-3-yl]-methyl-amino}-methyl)-benzonitrile

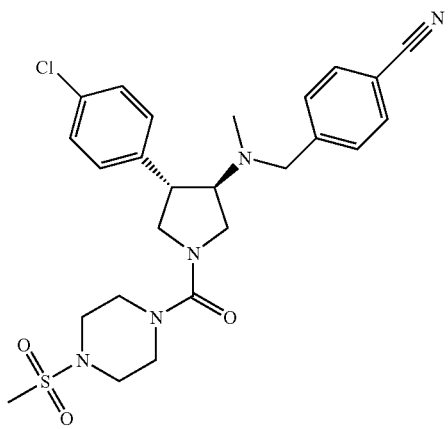

Reductive amination according to general procedure III:
Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2),
Aldehyde: 4-Formyl-benzonitrile (commercially available),
ES-MS m/e: 516.3 (M+H$^+$).

Example 27

[(3RS,4SR)-3-(Biphenyl-4-ylmethyl-methyl-amino)-4-(4-chloro-phenyl)-pyrrolidin-1-yl]-(4-methane-sulfonyl-piperazin-1-yl)-methanone

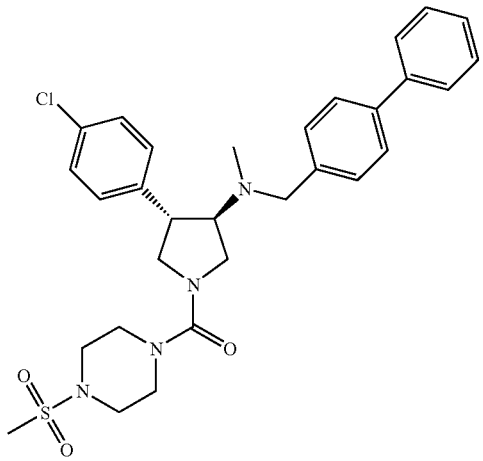

Reductive amination according to general procedure III:
Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2),
Aldehyde: Biphenyl-4-carbaldehyde (commercially available),
ES-MS m/e: 567.4 (M+H$^+$).

Example 28

((3SR,4RS)-3-(4-Chloro-phenyl)-4-{methyl-[4-(1,1,2,2-tetrafluoro-ethoxy)-benzyl]-amino}-pyrrolidin-1-yl)-(4-methanesulfonyl-piperazin-1-yl)-methanone

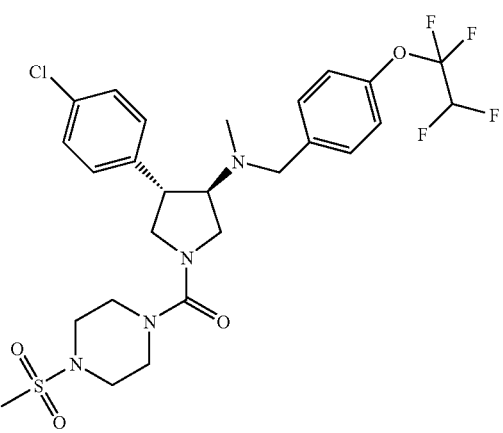

Reductive amination according to general procedure III:
Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2),
Aldehyde: 4-(1,1,2,2-Tetrafluoro-ethoxy)-benzaldehyde (commercially available),
ES-MS m/e: 607.3 (M+H$^+$).

Example 29

[(3RS,4SR)-3-[(4-Chloro-3-fluoro-benzyl)-methyl-amino]-4-(4-chloro-phenyl)-pyrrolidin-1-yl]-(4-methanesulfonyl-piperazin-1-yl)-methanone

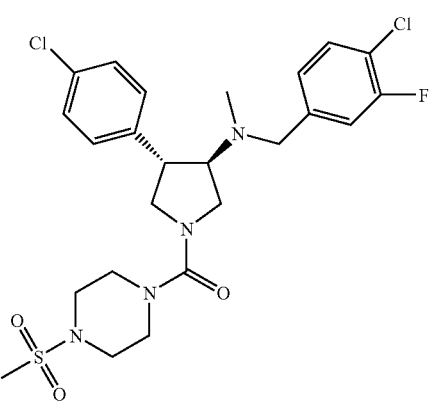

Reductive amination according to general procedure III:
Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2),
Aldehyde: 4-Chloro-3-fluoro-benzaldehyde (commercially available),
ES-MS m/e: 543.2 (M+H$^+$).

Example 30

{(3SR,4RS)-3-(4-Chloro-phenyl)-4-[(3-fluoro-4-trifluoromethyl-benzyl)-methyl-amino]-pyrrolidin-1-yl}-(4-methanesulfonyl-piperazin-1-yl)-methanone

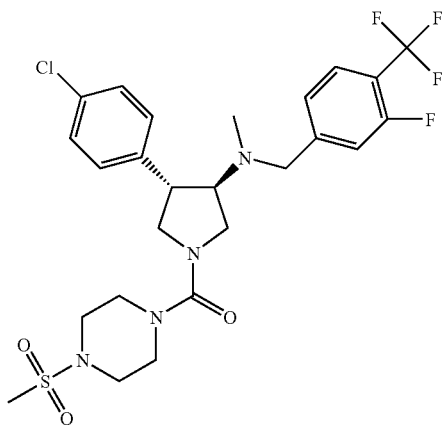

Reductive amination according to general procedure III:

Pyrrolidine intermediate: [(3SR,4RS)-3-(4-Chloro-phenyl)-4-methylamino-pyrrolidin-1-yl]-(4-methanesulfonyl-piperazin-1-yl)-methanone (XII-2), Aldehyde: 3-Fluoro-4-trifluoromethyl-benzaldehyde (commercially available), ES-MS m/e: 577.3 (M+H$^+$).

Example 31

{(3SR,4RS)-3-(3,4-Dichloro-phenyl)-4-[(3-fluoro-4-trifluoromethyl-benzyl)-methyl-amino]-pyrrolidin-1-yl}-(4-methanesulfonyl-piperazin-1-yl)-methanone

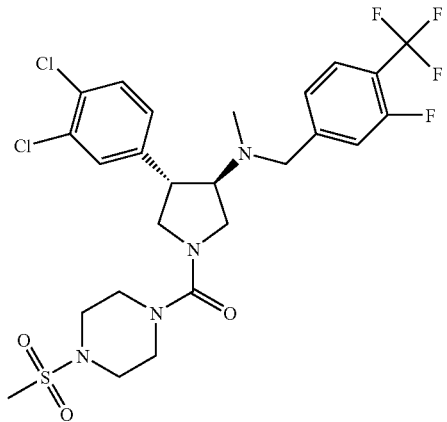

Reductive amination according to general procedure III:

Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3), Aldehyde: 3-Fluoro-4-trifluoromethyl-benzaldehyde (commercially available), ES-MS m/e: 611.2 (M+H$^+$).

Example 32

[(3RS,4SR)-3-[(3,4-Dichloro-benzyl)-methyl-amino]-4-(3,4-dichloro-phenyl)-pyrrolidin-1-yl]-4-methanesulfonyl-piperazin-1-yl)-methanone

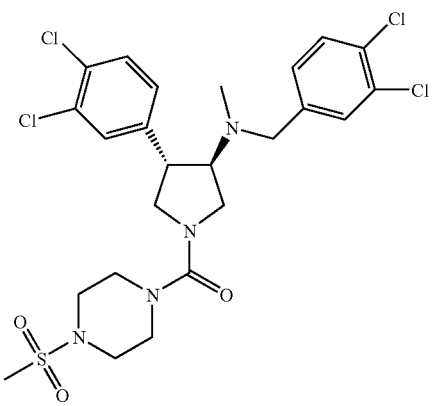

Reductive amination according to general procedure III:

Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3), Aldehyde: 3,4-Dichloro-benzaldehyde (commercially available), ES-MS m/e: 595.2 (M+H$^+$).

Example 33

[(3RS,4SR)-3-[(4-Chloro-benzyl)-methyl-amino]-4-(3,4-dichloro-phenyl)-pyrrolidin-1-yl]-(4-methanesulfonyl-piperazin-1-yl)-methanone

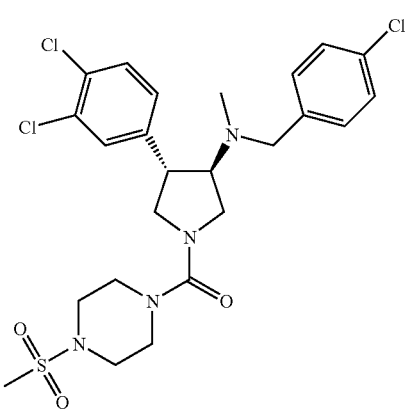

Reductive amination according to general procedure III:

Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3), Aldehyde: 4-Chloro-benzaldehyde (commercially available), ES-MS m/e: 561.1 (M+H$^+$).

Example 34

4-({[(3RS,4SR)-4-(3,4-Dichloro-phenyl)-1-(4-methanesulfonyl-piperazine-1-carbonyl)-pyrrolidin-3-yl]-methyl-amino}-methyl)-benzonitrile

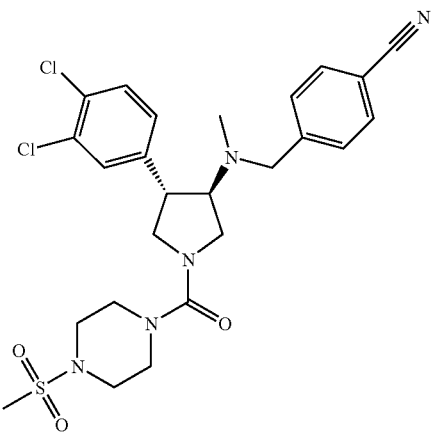

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Formyl-benzonitrile (commercially available),
ES-MS m/e: 550.3 (M+H$^+$).

Example 35

1-[4-({[(3RS,4SR)-4-(3,4-Dichloro-phenyl)-1-(4-methanesulfonyl-piperazine-1-carbonyl)-pyrrolidin-3-yl]-methyl-amino}-methyl)-phenyl]-ethanone

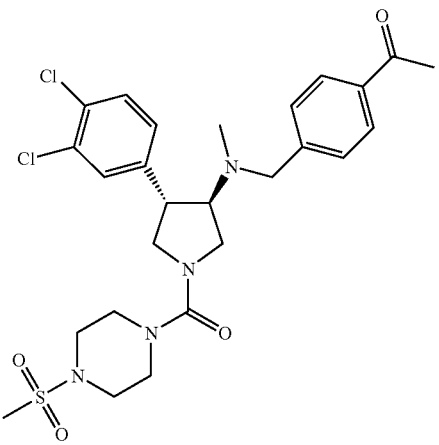

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Acetyl-benzaldehyde (commercially available),
ES-MS m/e: 567.3 (M+H$^+$).

Example 36

{(3SR,4RS)-3-(3,4-Dichloro-phenyl)-4-[(3,4-difluoro-benzyl)-methyl-amino]-pyrrolidin-1-yl}-(4-methanesulfonyl-piperazin-1-yl)-methanone

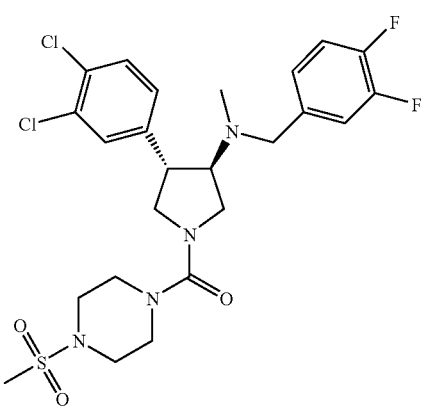

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 3,4-Difluoro-benzaldehyde (commercially available),
ES-MS m/e: 561.3 (M+H$^+$).

Example 37

{(3SR,4RS)-3-(3,4-Dichloro-phenyl)-4-[(2,3-dihydro-benzofuran-6-ylmethyl)-methyl-amino]-pyrrolidin-1-yl}-(4-methanesulfonyl-piperazin-1-yl)-methanone

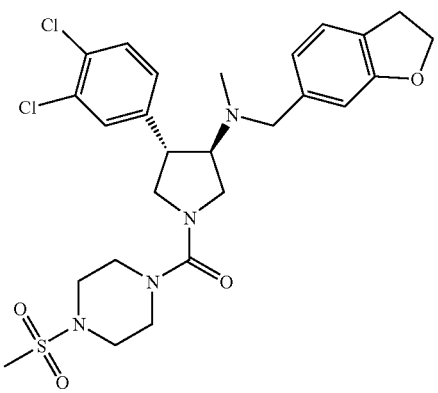

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 2,3-Dihydro-benzofuran-6-carbaldehyde (commercially available),
ES-MS m/e: 567.3 (M+H$^+$).

Example 38

{(3SR,4RS)-3-(3,4-Dichloro-phenyl)-4-[(3-fluoro-5-trifluoromethyl-benzyl)-methyl-amino]-pyrrolidin-1-yl}-(4-methanesulfonyl-piperazin-1-yl)-methanone

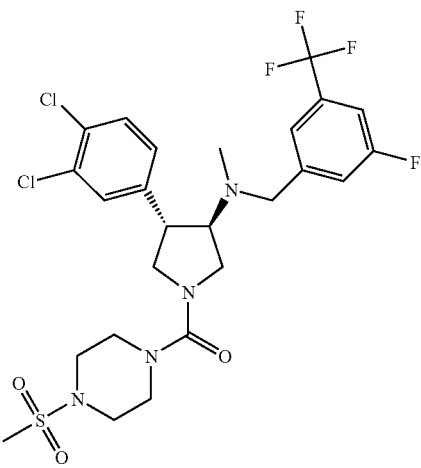

Reductive amination according to general procedure 111:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 3-Fluoro-5-trifluoromethyl-benzaldehyde (commercially available),
ES-MS m/e: 611.2 (M+H$^+$).

Example 39

{(3SR,4RS)-3-(3,4-Dichloro-phenyl)-4-[(3,5-difluoro-benzyl)-methyl-amino]-pyrrolidin-1-yl}-(4-methanesulfonyl-piperazin-1-yl)-methanone

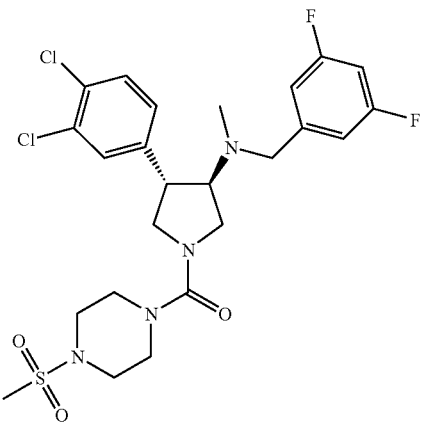

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 3,5-Difluoro-benzaldehyde (commercially available),
ES-MS m/e: 561.2 (M+H$^+$).

Example 40

{(3SR,4RS)-3-(3,4-Dichloro-phenyl)-4-[(4-ethyl-benzyl)-methyl-amino]-pyrrolidin-1-yl}-(4-methanesulfonyl-piperazin-1-yl)-methanone

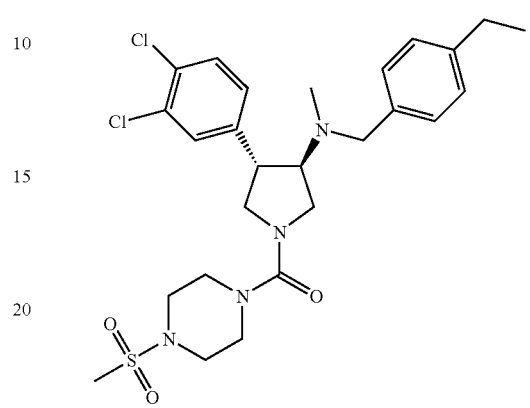

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Ethyl-benzaldehyde (commercially available),
ES-MS m/e: 553.2 (M+H$^+$).

Example 41

{(3SR,4RS)-3-(3,4-Dichloro-phenyl)-4-[(3,4-dimethyl-benzyl)-methyl-amino]-pyrrolidin-1-yl}-(4-methanesulfonyl-piperazin-1-yl)-methanone

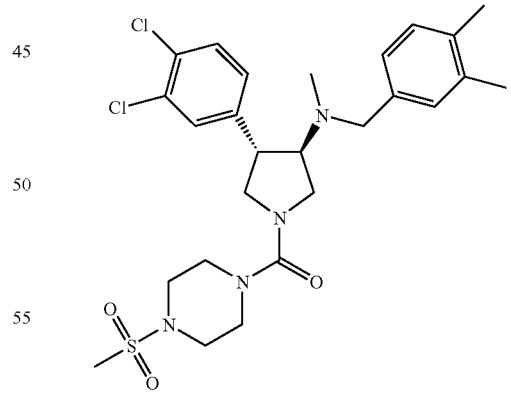

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 3,4-Dimethyl-benzaldehyde (commercially available),
ES-MS m/e: 553.2 (M+H$^+$).

Example 42

{(3SR,4RS)-3-(3,4-Dichloro-phenyl)-4-[(4-isopropyl-benzyl)-methyl-amino]-pyrrolidin-1-yl}-(4-methanesulfonyl-piperazin-1-yl)-methanone

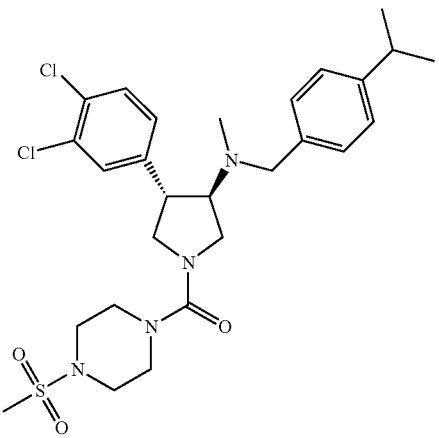

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Isopropyl-benzaldehyde (commercially available),
ES-MS m/e: 567.3 (M+H$^+$).

Example 43

{(3SR,4RS)-3-(3,4-Dichloro-phenyl)-4-[(4-fluoro-3-methyl-benzyl)-methyl-amino]-pyrrolidin-1-yl}-(4-methanesulfonyl-piperazin-1-yl)-methanone

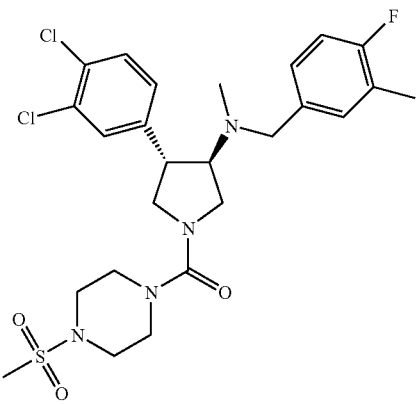

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Fluoro-3-methyl-benzaldehyde (commercially available),
ES-MS m/e: 557.2 (M+H$^+$).

Example 44

{(3SR,4RS)-3-(3,4-Dichloro-phenyl)-4-[(4-ethoxy-benzyl)-methyl-amino]-pyrrolidin-1-yl}-(4-methanesulfonyl-piperazin-1-yl)-methanone

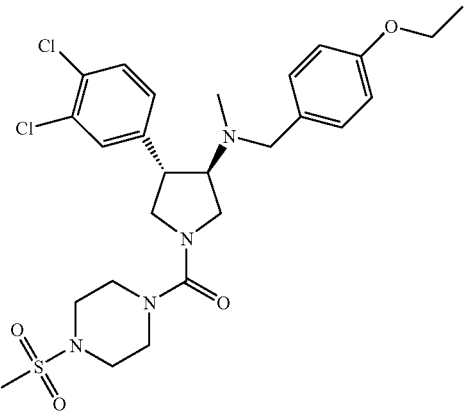

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Ethoxy-benzaldehyde (commercially available),
ES-MS m/e: 559.2 (M+H$^+$).

Example 45

{(3SR,4RS)-3-(3,4-Dichloro-phenyl)-4-[(4-dimethylamino-benzyl)-methyl-amino]-pyrrolidin-1-yl}-(4-methanesulfonyl-piperazin-1-yl)-methanone

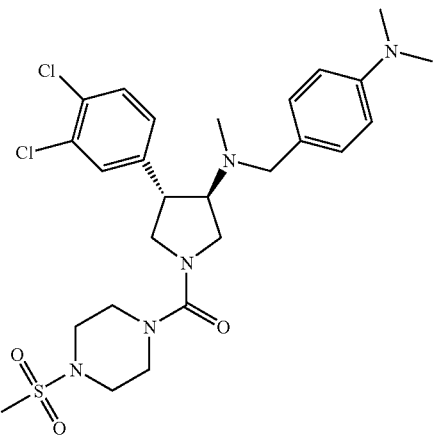

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Dimethylamino-benzaldehyde (commercially available),
ES-MS m/e: 568.2 (M+H$^+$).

Example 46

{(3SR,4RS)-3-(3,4-Dichloro-phenyl)-4-[(1H-indol-5-ylmethyl)-methyl-amino]-pyrrolidin-1-yl}-(4-methanesulfonyl-piperazin-1-yl)-methanone

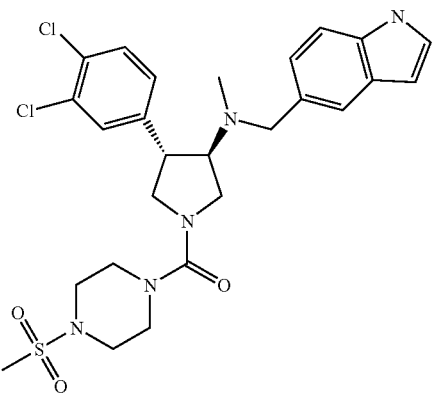

Reductive amination according to general procedure III:

Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3), Aldehyde: 1H-Indole-5-carbaldehyde (commercially available), ES-MS m/e: 564.4 (M+H$^+$).

Example 47

{(3SR,4RS)-3-(3,4-Dichloro-phenyl)-4-[(1H-indol-6-ylmethyl)-methyl-amino]-pyrrolidin-1-yl}-(4-methanesulfonyl-piperazin-1-yl)-methanone

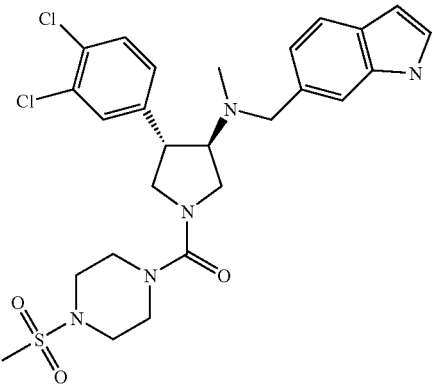

Reductive amination according to general procedure III:

Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3), Aldehyde: 1H-Indole-6-carbaldehyde (commercially available), ES-MS m/e: 564.4 (M+H$^+$).

Example 48

(3SR,4RS)-3-(3,4-Dichloro-phenyl)-4-[(3-fluoro-4-trifluoromethyl-benzyl)-methyl-amino]-pyrrolidine-1-carboxylic acid (2-hydroxy-ethyl)-amide

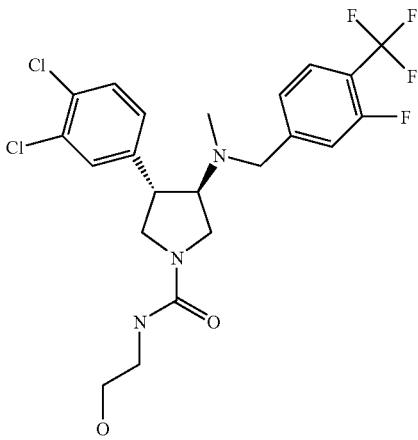

Coupling reaction according to general procedure V:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1), Amine: 2-Amino-ethanol (commercially available), ES-MS m/e: 508.2 (M+H$^+$).

Example 49

(3SR,4RS)-3-(3,4-Dichloro-phenyl)-4-[(3-fluoro-4-trifluoromethyl-benzyl)-methyl-amino]-pyrrolidine-1-carboxylic acid (3-hydroxy-propyl)-amide

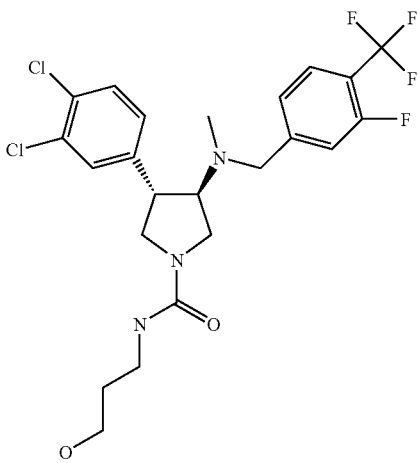

Coupling reaction according to general procedure V:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1), Amine: 3-Amino-propan-1-ol (commercially available), ES-MS m/e: 522.3 (M+H$^+$).

Example 50

(3SR,4RS)-3-(3,4-Dichloro-phenyl)-4-[(3-fluoro-4-trifluoromethyl-benzyl)-methyl-amino]-pyrrolidine-1-carboxylic acid (2-hydroxy-ethyl)-methyl-amide

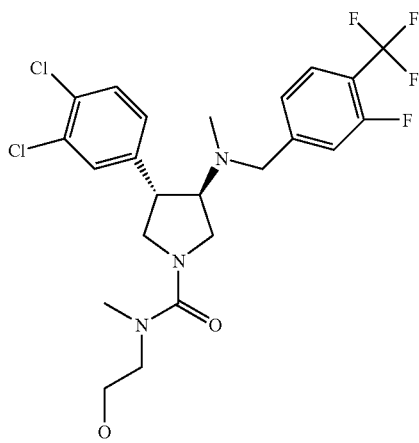

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 2-Methylamino-ethanol (commercially available),
ES-MS m/e: 522.3 (M+H$^+$).

Example 51

1-(4-{(3SR,4RS)-3-(3,4-Dichloro-phenyl)-4-[(3-fluoro-4-trifluoromethyl-benzyl)-methyl-amino]-pyrrolidine-1-carbonyl}-piperazin-1-yl)-ethanone

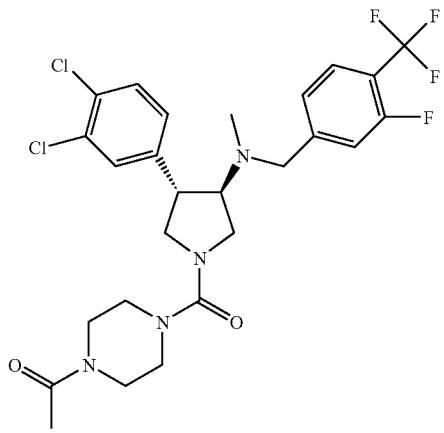

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 1-piperazin-1-yl-ethanone (commercially available),
ES-MS m/e: 575.3 (M+H$^+$).

Example 52

{(3SR,4RS)-3-(3,4-Dichloro-phenyl)-4-[(3-fluoro-4-trifluoromethyl-benzyl)-methyl-amino]-pyrrolidin-1-yl}-morpholin-4-yl-methanone

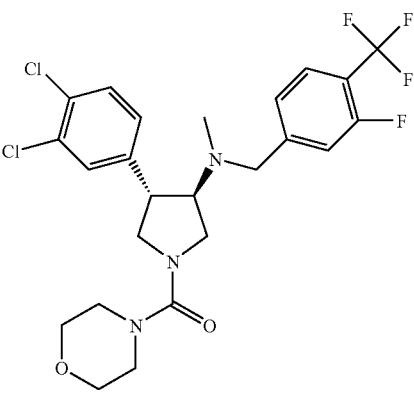

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: Morpholine (commercially available),
ES-MS m/e: 534.2 (M+H$^+$).

Example 53

(3SR,4RS)-3-(3,4-Dichloro-phenyl)-4-[(3-fluoro-4-trifluoromethyl-benzyl)-methyl-amino]-pyrrolidine-1-carboxylic acid dimethylamide

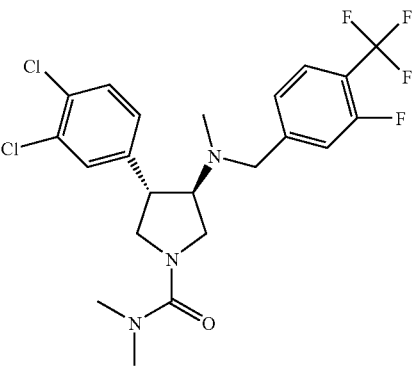

Coupling reaction according to general procedure II:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carbamoyl chloride: N,N-dimethyl carbamoyl chloride (commercially available),
ES-MS m/e: 492.3 (M+H$^+$).

Example 54

1-{(3SR,4RS)-3-(3,4-Dichloro-phenyl)-4-[(3-fluoro-4-trifluoromethyl-benzyl)-methyl-amino]-pyrrolidin-1-yl}-ethanone

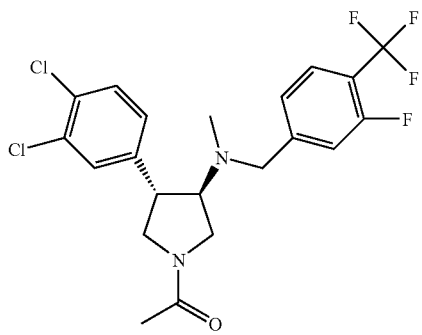

Coupling reaction according to general procedure II:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Acid chloride: acetyl chloride (commercially available), ES-MS m/e: 463.2 (M+H$^+$).

Example 55

(3SR,4RS)-3-(3,4-Dichloro-phenyl)-4-[(3-fluoro-4-trifluoromethyl-benzyl)-methyl-amino]-pyrrolidine-1-carboxylic acid ethyl ester

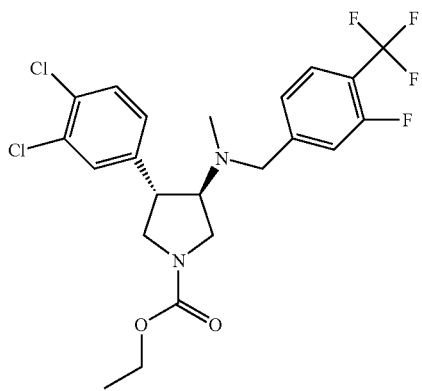

Coupling reaction according to general procedure II:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), chloroformate: ethyl chloroformate (commercially available), ES-MS m/e: 493.2 (M+H$^+$).

Example 56

4-({[(3RS,4SR)-4-(3,4-Dichloro-phenyl)-1-(4-methanesulfonyl-piperazine-1-carbonyl)-pyrrolidin-3-yl]-methyl-amino}-methyl)-2-fluoro-benzonitrile

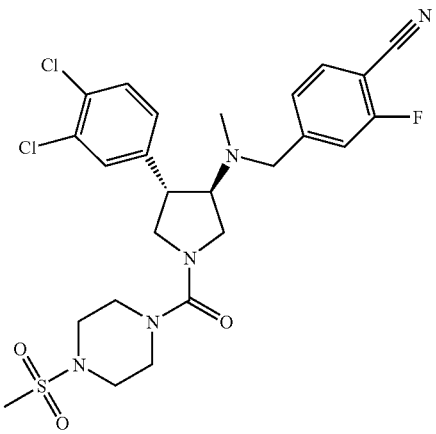

Reductive amination according to general procedure III:

Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3), Aldehyde: 2-Fluoro-4-formyl-benzonitrile (commercially available), ES-MS m/e: 568.2 (M+H$^+$).

Example 57

{(3SR,4RS)-3-(3,4-Dichloro-phenyl)-4-[(3-fluoro-4-trifluoromethyl-benzyl)-methyl-amino]-pyrrolidin-1-yl}-((R)-3-dimethylamino-pyrrolidin-1-yl)-methanone

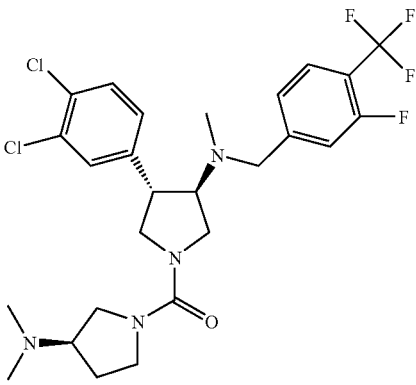

Coupling reaction according to general procedure V:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1), Amine: Dimethyl-(R)-pyrrolidin-3-yl-amine (commercially available), ES-MS m/e: 561.1 (M+H$^+$).

Example 58

{(3SR,4RS)-3-(3,4-Dichloro-phenyl)-4-[(3-fluoro-4-trifluoromethyl-benzyl)-methyl-amino]-pyrrolidin-1-yl}-((S)-3-dimethylamino-pyrrolidin-1-yl)-methanone

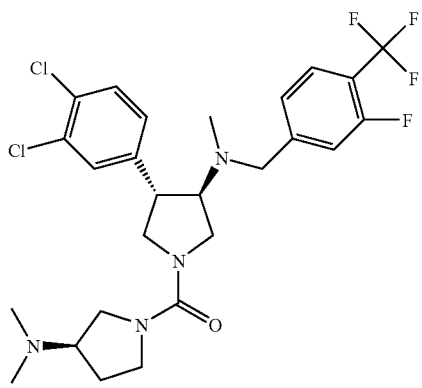

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: Dimethyl-(S)-pyrrolidin-3-yl-amine (commercially available),
ES-MS m/e: 561.2 (M+H$^+$).

Example 59

{(3SR,4RS)-3-(3,4-Dichloro-phenyl)-4-[(3-fluoro-4-trifluoromethyl-benzyl)-methyl-amino]-pyrrolidin-1-yl}-((S)-4-methanesulfonyl-3-methyl-piperazin-1-yl)-methanone

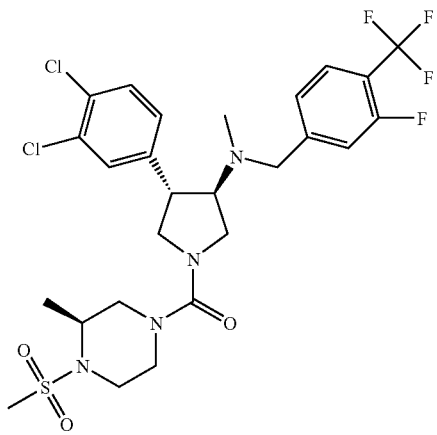

Coupling reaction according to general procedure II:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
carbamoyl chloride: (S)-4-Methanesulfonyl-3-methyl-piperazine-1-carbonyl chloride,
ES-MS m/e: 625.2 (M+H$^+$).

(S)-4-Methanesulfonyl-3-methyl-piperazine-1-carbonyl chloride

First step: To a stirred solution of commercially available (S)-3-methyl-piperazine-1-carboxylic acid tert-butyl ester (2.38 g, 12 mmol) in CH$_2$Cl$_2$ (25 mL) at 0° C. were added pyridine (1.91 mL, 24 mmol) and methanesulfonyl chloride (0.92 mL, 12 mmol). Stirring was continued at RT overnight, the reaction was poured onto water and extracted with CH$_2$Cl$_2$. The combined organic phases were dried on Na$_2$SO$_4$ and concentrated under vacuo. The crude product was dissolved in CH$_2$Cl$_2$ (20 mL) and TFA (4 mL) was added. After 2 hours at RT, the volatiles were removed under vacuo, the crude was dissolved in CH$_2$Cl$_2$ and washed with aq. NaHCO$_3$ (until pH=8). The organic phase was dried on Na$_2$SO$_4$ and concentrated under vacuo to yield 0.83 g (39%) of (s)-1-methanesulfonyl-2-methyl-piperazine as a light yellow oil.

Second step: To a stirred solution of carbonic acid ditrichloromethyl ester (triphosgene) (560 mg, 1.88 mmol) in CH$_2$Cl$_2$ (10 mL) at −78° C., was added a solution of (S)-1-methanesulfonyl-2-methyl-piperazine (838 mg, 4.70 mmol) and pyridine (0.74 mL, 9.4 mmol) in CH$_2$Cl$_2$ (10 mL) over 1 hour. The temperature was raised to RT, and stirring was continued over night. The organic phase was washed with H$_2$O, dried over Na$_2$SO$_4$. Concentration under vacuo and flash chromatography (SiO$_2$, EtOAc/H, 1:1) yielded 0.70 g (62%) of (S)-4-methanesulfonyl-3-methyl-piperazine-1-carbonyl chloride as a light yellow solid.

Example 60

{(3SR,4RS)-3-(3,4-Dichloro-phenyl)-4-[(3-fluoro-4-trifluoromethyl-benzyl)-methyl-amino]-pyrrolidin-1-yl}-((R)-4-methanesulfonyl-3-methyl-piperazin-1-yl)-methanone

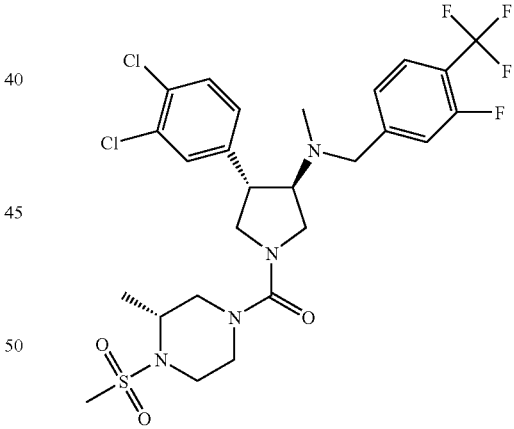

Coupling reaction according to general procedure II:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
carbamoyl chloride: (R)-4-Methanesulfonyl-3-methyl-piperazine-1-carbonyl chloride,
ES-MS m/e: 625.2 (M+H$^+$).

(R)-4-Methanesulfonyl-3-methyl-piperazine-1-carbonyl chloride

First step: To a stirred solution of commercially available (R)-3-methyl-piperazine-1-carboxylic acid tert-butyl ester (8.78 g, 44 mmol) in CH$_2$Cl$_2$ (80 mL) at 0° C. were added Et$_3$N (12.15 mL, 88 mmol) and methanesulfonyl chloride (5.09 mL, 66 mmol). Stirring was continued at RT overnight, the reaction was poured onto water and extracted with CH$_2$Cl$_2$. The combined organic phases were dried on Na$_2$SO$_4$ and concentrated under vacuo. The crude product was dissolved in CH$_2$Cl$_2$ (50 mL) and TFA (15 mL) was added. After 2 hours at RT, the volatiles were removed under vacuo, the crude was dissolved in CH$_2$Cl$_2$ and washed with aq. NaHCO$_3$ (until pH=8). The organic phase was dried on Na$_2$SO$_4$ and concentrated under vacuo to yield 2.63 g (34%) of (R)-1-methanesulfonyl-2-methyl-piperazine as a light yellow oil.

Second step: To a stirred solution of carbonic acid ditrichloromethyl ester (triphosgene) (1.17 g, 3.95 mmol) in CH$_2$Cl$_2$ (20 mL) at −78° C., was added a solution of (R)-1-methanesulfonyl-2-methyl-piperazine (1.76 g, 9.9 mmol) and pyridine (1.60 mL, 20 mmol) in CH$_2$Cl$_2$ (20 mL) over 1 hour. The temperature was raised to RT, and stirring was continued over night. The organic phase was washed with H$_2$O, dried over Na$_2$SO$_4$. Concentration under vacuo and flash chromatography (SiO$_2$, EtOAc/H, 1:1) yielded 1.70 g (71%) of (R)-4-methanesulfonyl-3-methyl-piperazine-1-carbonyl chloride as a light yellow solid.

Example 61

2-(4-tert-Butyl-phenoxy)-1-{(3SR,4RS)-3-(3,4-dichloro-phenyl)-4-[(3-fluoro-4-trifluoromethyl-benzyl)-methyl-amino]-pyrrolidin-1-yl}-ethanone

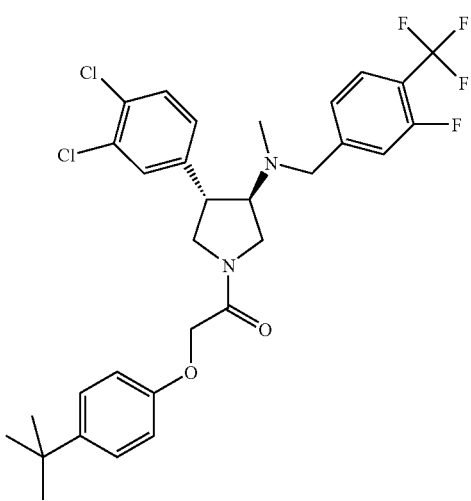

Coupling reaction according to general procedure 1:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: (4-tert-Butyl-phenoxy)-acetic acid (commercially available),
ES-MS m/e: 611.2 (M+H$^+$).

Example 62

1-{(3SR,4RS)-3-(3,4-Dichloro-phenyl)-4-[(3-fluoro-4-trifluoromethyl-benzyl)-methyl-amino]-pyrrolidin-1-yl}-5-morpholin-4-yl-pentan-1-one

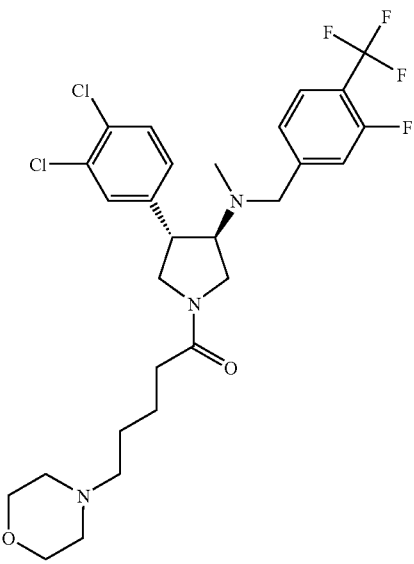

Coupling reaction according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 5-Morpholin-4-yl-pentanoic acid (described in J. Molecular Structure 2001, 560, p. 261), ES-MS m/e: 590.5 (M+H$^+$).

Example 63

{(3SR,4RS)-3-(3,4-Dichloro-phenyl)-4-[(3-fluoro-4-trifluoromethyl-benzyl)-methyl-amino]-pyrrolidin-1-yl}-(4-pyrimidin-2-yl-piperazin-1-yl)-methanone

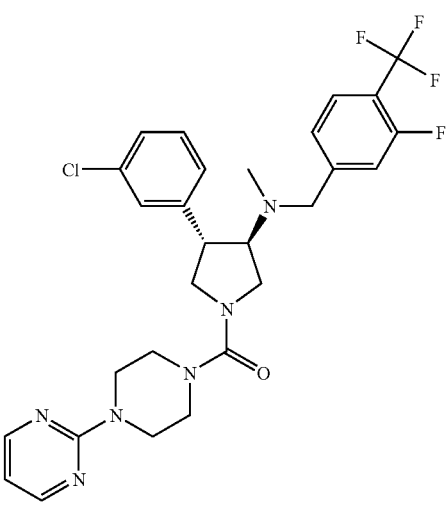

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 2-piperazin-1-yl-pyrimidine (commercially available),
ES-MS m/e: 611.5 (M+H⁺).

Example 64

{(3SR,4RS)-3-(3,4-Dichloro-phenyl)-4-[(3-fluoro-4-trifluoromethyl-benzyl)-methyl-amino]-pyrrolidin-1-yl}-[4-(4-methoxy-phenyl)-piperazin-1-yl]-methanone

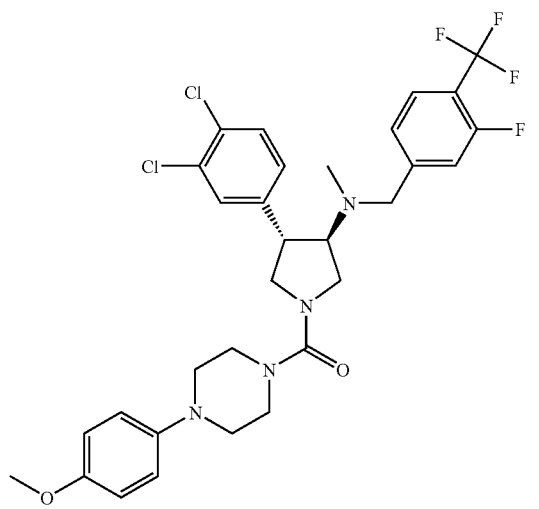

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 1-(4-Methoxy-phenyl)-piperazine (commercially available),
ES-MS m/e: 639.5 (M+H⁺).

Example 65

{(3SR,4RS)-3-(3,4-Dichloro-phenyl)-4-[(3-fluoro-4-trifluoromethyl-benzyl)-methyl-amino]-pyrrolidin-1-yl}-(4-pyridin-2-yl-piperazin-1-yl)-methanone

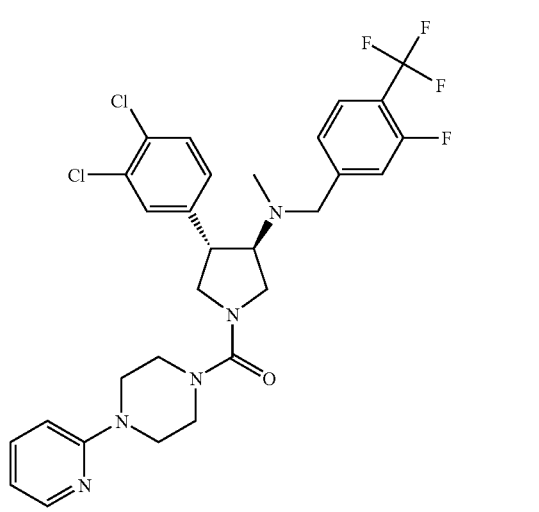

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 1-Pyridin-2-yl-piperazine (commercially available),
ES-MS m/e: 610.5 (M+H⁺).

Example 66

{(3SR,4RS)-3-(3,4-Dichloro-phenyl)-4-[(3-fluoro-4-trifluoromethyl-benzyl)-methyl-amino]-pyrrolidin-1-yl}-[4-(3-hydroxy-propyl)-piperazin-1-yl]-methanone

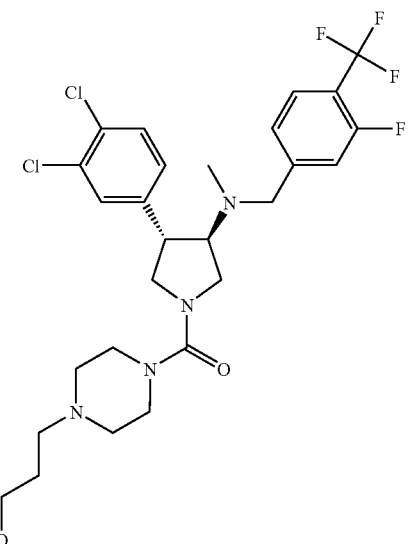

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 3-piperazin-1-yl-propan-1-ol (commercially available),
ES-MS m/e: 591.5 (M+H⁺).

Example 67

{(3SR,4RS)-3-(3,4-Dichloro-phenyl)-4-[(3-fluoro-4-trifluoromethyl-benzyl)-methyl-amino]-pyrrolidin-1-yl}-[4-(2-hydroxy-ethyl)-piperazin-1-yl]-methanone

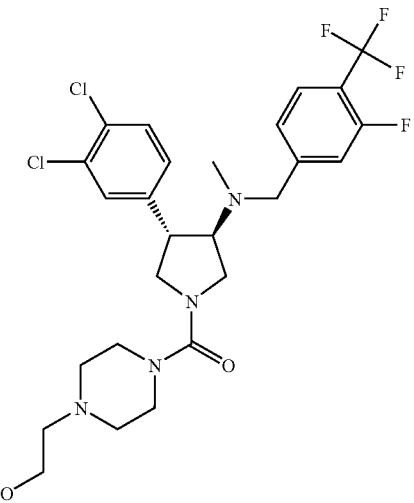

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 3-piperazin-1-yl-ethan-1-ol (commercially available),
ES-MS m/e: 577.4 (M+H$^+$).

Example 68

{(3SR,4RS)-3-(3,4-Dichloro-phenyl)-4-[(3-fluoro-4-trifluoromethyl-benzyl)-methyl-amino]-pyrrolidin-1-yl}-(4-pyridin-4-yl-piperazin-1-yl)-methanone

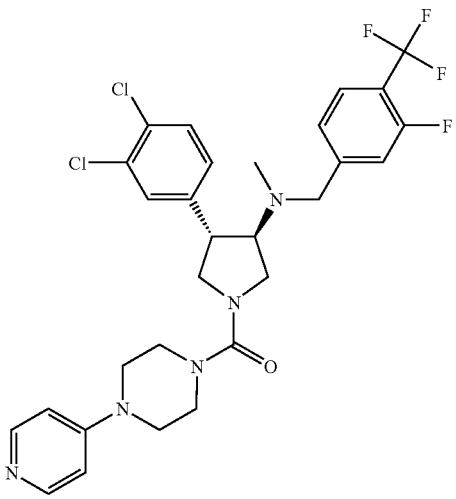

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 1-Pyridin-4-yl-piperazine (commercially available),
ES-MS m/e: 610.5 (M+H$^+$).

Example 69

{(3SR,4RS)-3-(3,4-Dichloro-phenyl)-4-[(3-fluoro-4-trifluoromethyl-benzyl)-methyl-amino]-pyrrolidin-1-yl}-(2,3,5,6-tetrahydro-[1,2']bipyrazinyl-4-yl)-methanone

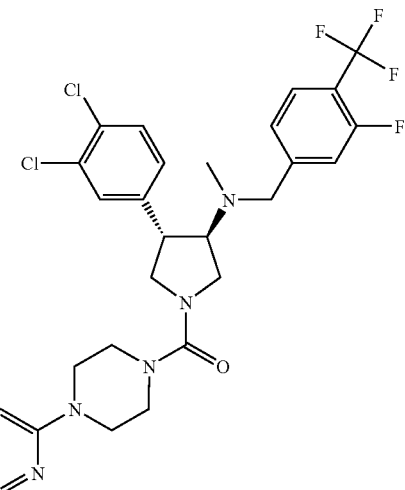

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 3,4,5,6-Tetrahydro-2H-[1,2']bipyrazinyl (commercially available),
ES-MS m/e: 611.2 (M+H$^+$).

Example 70

2-(4-{(3SR,4RS)-3-(3,4-Dichloro-phenyl)-4-[(3-fluoro-4-trifluoromethyl-benzyl)-methyl-amino]-pyrrolidine-1-carbonyl}-piperazin-1-yl)-benzonitrile

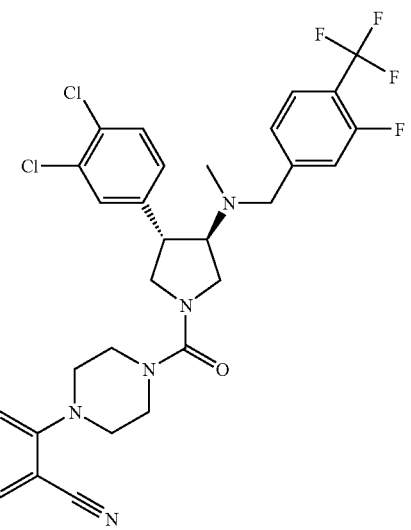

Coupling reaction according to general procedure V:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1), Amine: 2-piperazin-1-yl-benzonitrile (commercially available), ES-MS m/e: 634.2 (M+H$^+$).

Example 71

2-(4-{(3S,4R)-3-(3,4-Dichloro-phenyl)-4-[(3-fluoro-4-trifluoromethyl-benzyl)-methyl-amino]-pyrrolidine-1-carbonyl}-piperazin-1-yl)-nicotinonitrile

Example 72

4-(4-{(3SR,4RS)-3-(3,4-Dichloro-phenyl)-4-[(3-fluoro-4-trifluoromethyl-benzyl)-methyl-amino]-pyrrolidine-1-carbonyl}-piperazin-1-yl)-benzonitrile

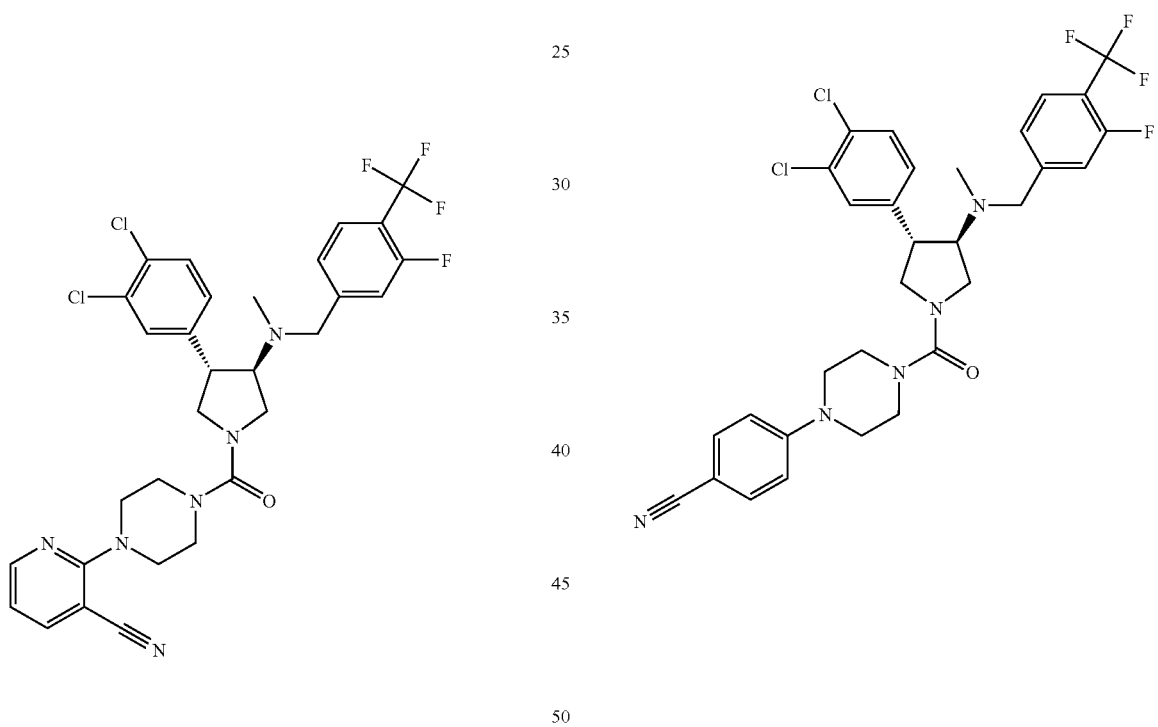

Coupling reaction according to general procedure V:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1), Amine: 2-piperazin-1-yl-nicotinonitrile (commercially available), ES-MS m/e: 635.2 (M+H$^+$).

Coupling reaction according to general procedure V:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1), Amine: 4-piperazin-1-yl-benzonitrile (commercially available), ES-MS m/e: 634.2 (M+H$^+$).

Example 73

6-(4-{(3SR,4RS)-3-(3,4-Dichloro-phenyl)-4-[(3-fluoro-4-trifluoromethyl-benzyl)-methyl-amino]-pyrrolidine-1-carbonyl}-piperazin-1-yl)-nicotinonitrile

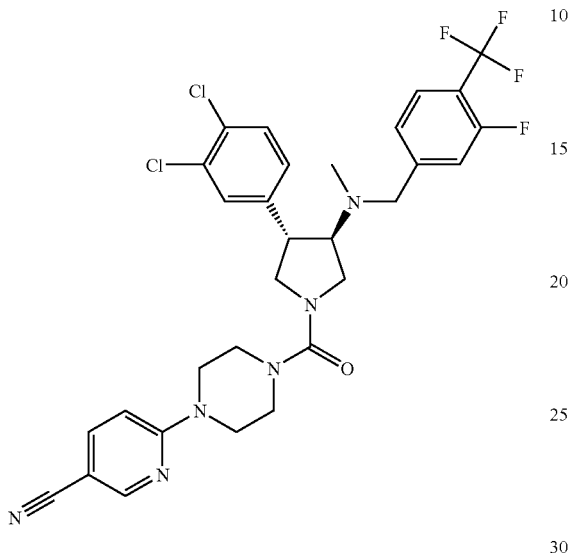

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 6-piperazin-1-yl-nicotinonitrile (commercially available),
ES-MS m/e: 635.2 (M+H$^+$).

Example 74

{(3SR,4RS)-3-(3,4-Dichloro-phenyl)-4-[(3-fluoro-4-trifluoromethyl-benzyl)-methyl-amino]-pyrrolidin-1-yl}-[4-(3-dimethylamino-propyl)-piperazin-1-yl]-methanone

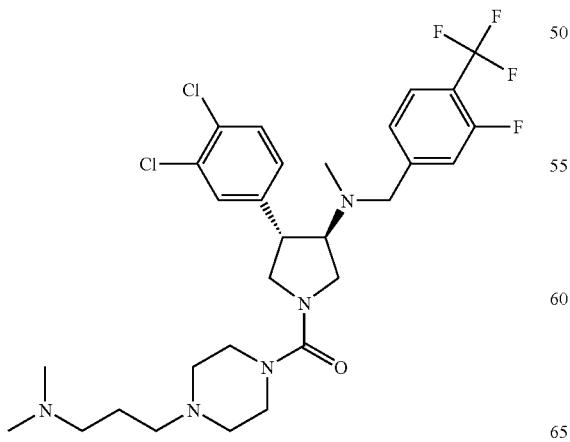

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: Dimethyl-(3-piperazin-1-yl-propyl)-amine (commercially available),
ES-MS m/e: 618.2 (M+H$^+$).

Example 75

{(3SR,4RS)-3-(3,4-Dichloro-phenyl)-4-[(3-fluoro-4-trifluoromethyl-benzyl)-methyl-amino]-pyrrolidin-1-yl}-[4-(2-dimethylamino-ethyl)-piperazin-1-yl]-methanone

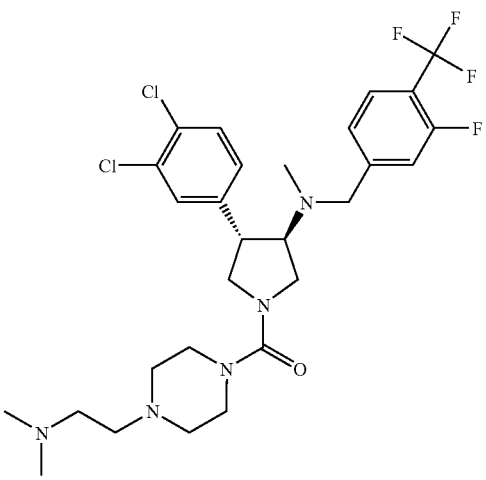

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: Dimethyl-(2-piperazin-1-yl-ethyl)-amine (commercially available),
ES-MS m/e: 604.2 (M+H$^+$).

Example 76

4-{(3SR,4RS)-3-(3,4-Dichloro-phenyl)-4-[(3-fluoro-4-trifluoromethyl-benzyl)-methyl-amino]-pyrrolidine-1-carbonyl}-piperazine-1-sulfonic acid dimethylamide

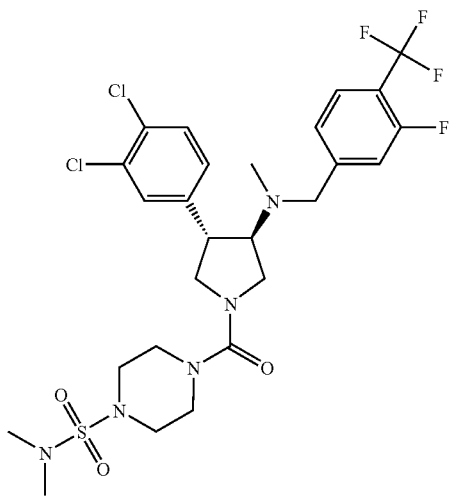

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: piperazine-1-sulfonic acid dimethylamide (commercially available),
ES-MS m/e: 642.2 (M+H$^+$).

Example 77

{(3SR,4RS)-3-(3,4-Dichloro-phenyl)-4-[(3-fluoro-4-trifluoromethyl-benzyl)-methyl-amino]-pyrrolidin-1-yl}-[4-(6-methoxy-pyridin-2-yl)-piperazin-1-yl]-methanone

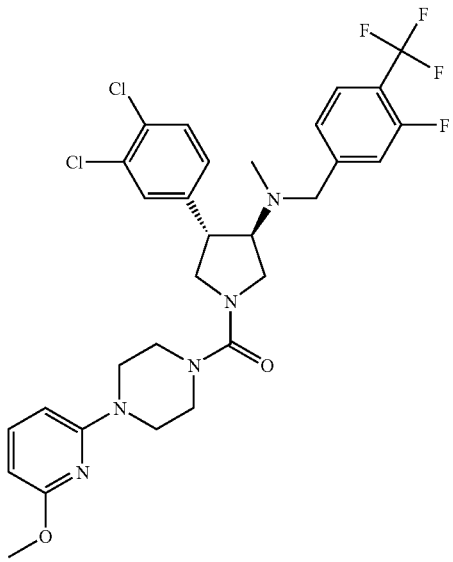

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 1-(6-Methoxy-pyridin-2-yl)-piperazine (commercially available),
ES-MS m/e: 640.2 (M+H$^+$).

Example 78

4-{(3SR,4RS)-3-(3,4-Dichloro-phenyl)-4-[(3-fluoro-4-trifluoromethyl-benzyl)-methyl-amino]-pyrrolidine-1-carbonyl}-piperazine-1-carboxylic acid diethylamide

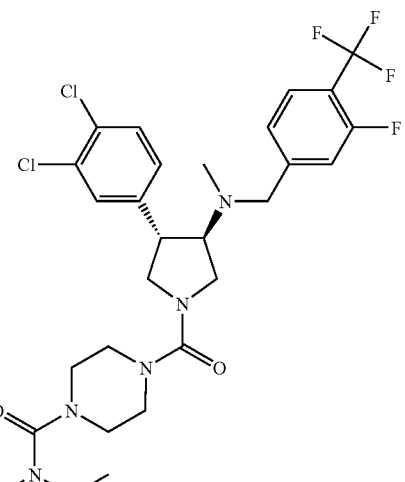

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: piperazine-1-carboxylic acid diethylamide (commercially available),
ES-MS m/e: 632.2 (M+H$^+$).

Example 79

3-(4-{(3SR,4RS)-3-(3,4-Dichloro-phenyl)-4-[(3-fluoro-4-trifluoromethyl-benzyl)-methyl-amino]-pyrrolidine-1-carbonyl}-piperazin-1-yl)-propionitrile

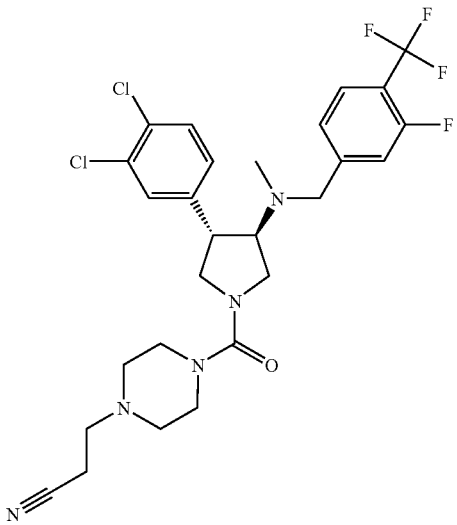

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 3-piperazin-1-yl-propionitrile (commercially available),
ES-MS m/e: 580.3 (M+H$^+$).

Example 80

{(3SR,4RS)-3-(3,4-Dichloro-phenyl)-4-[(3-fluoro-4-trifluoromethyl-benzyl)-methyl-amino]-pyrrolidin-1-yl}-(4-hydroxy-3,4,5,6-tetrahydro-2H-[4,4']bipyridinyl-1-yl)-methanone

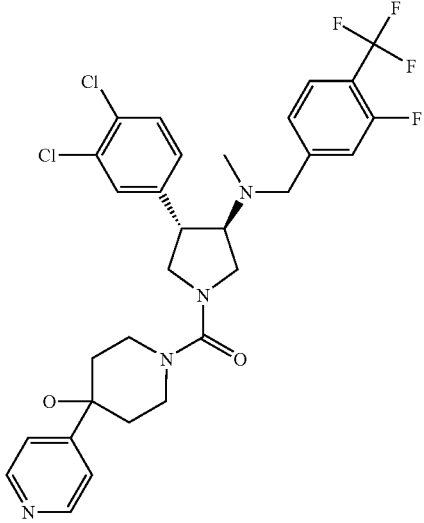

Coupling reaction according to general procedure V:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carbonyl chloride (XIII-1),
Amine: 2,3,5,6-Tetrahydro-1H-[4,4']bipyridinyl-4-ol (commercially available),
ES-MS m/e: 625.2 (M+H$^+$).

Example 81

{(3SR,4RS)-3-(4-Chloro-3-fluoro-phenyl)-4-[(3-fluoro-4-trifluoromethyl-benzyl)-methyl-amino]-pyrrolidin-1-yl}-(4-methanesulfonyl-piperazin-1-yl)-methanone

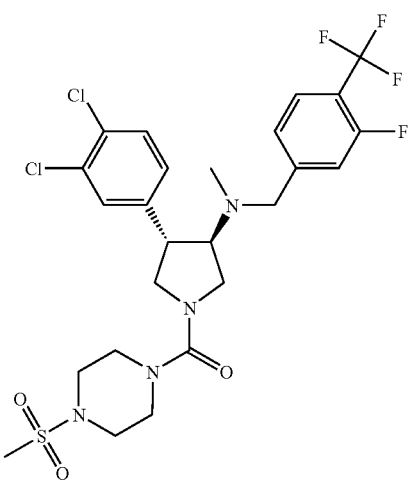

Coupling reaction according to general procedure II:
Pyrrolidine intermediate: [(3RS,4SR)-4-(4-Chloro-3-fluoro-phenyl)-pyrrolidin-3-yl]-(3-fluoro-4-trifluoromethyl-benzyl)-methyl-amine (VIII-2),
carbamoyl chloride: 4-methanesulfonyl-piperazine-1-carbonyl chloride (described herein above in the intermediate part),
ES-MS m/e: 594.7 (M+H$^+$).

Example 82

{(3SR,4RS)-3-(4-Chloro-3-fluoro-phenyl)-4-[(3-fluoro-4-trifluoromethyl-benzyl)-methyl-amino]-pyrrolidin-1-yl}-(4-methanesulfonyl-[1,4]diazepan-1-yl)-methanone

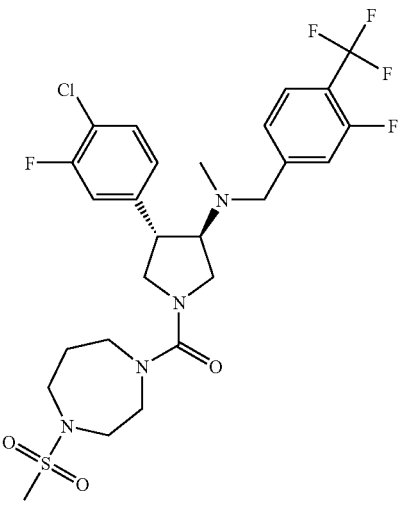

Coupling reaction according to general procedure II:
Pyrrolidine intermediate: [(3RS,4SR)-4-(4-Chloro-3-fluoro-phenyl)-pyrrolidin-3-yl]-(3-fluoro-4-trifluoromethyl-benzyl)-methyl-amine (VIII-2),
carbamoyl chloride: 4-Methanesulfonyl-[1,4]diazepane-1-carbonyl chloride (this compound was prepared from 1-Methanesulfonyl-[1,4]diazepane using the same procedure as for the preparation of 4-methanesulfonyl-piperazine-1-carbonyl chloride),
ES-MS m/e: 625.2 (M+H$^+$).

Example 83

{(3SR,4RS)-3-(3,4-Dichloro-phenyl)-4-[methyl-(4-trifluoromethyl-benzyl)-amino]-pyrrolidin-1-yl}-(4-methanesulfonyl-piperazin-1-yl)-methanone

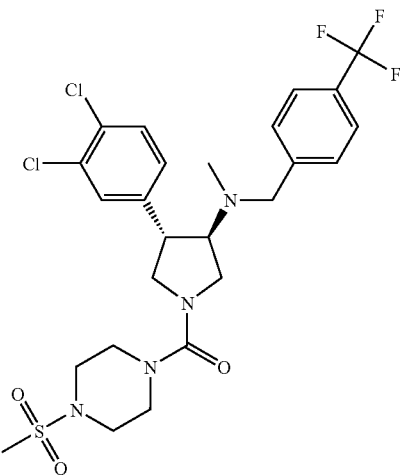

Reductive amination according to general procedure III:
Pyrrolidine intermediate: [(3SR,4RS)-3-(3,4-Dichloro-phenyl)-4-methylamino-pyrrolidin-1-yl]-(4-methanesulfonyl-piperazin-1-yl)-methanone (XII-3),
Aldehyde: 4-Trifluoromethyl-benzaldehyde (commercially available),
ES-MS m/e: 592.8 (M+H$^+$).

Example 84

1-{(3SR,4RS)-3-(3,4-Dichloro-phenyl)-4-[methyl-(4-trifluoromethyl-benzyl)-amino]-pyrrolidin-1-yl}-5-morpholin-4-yl-pentan-1-one

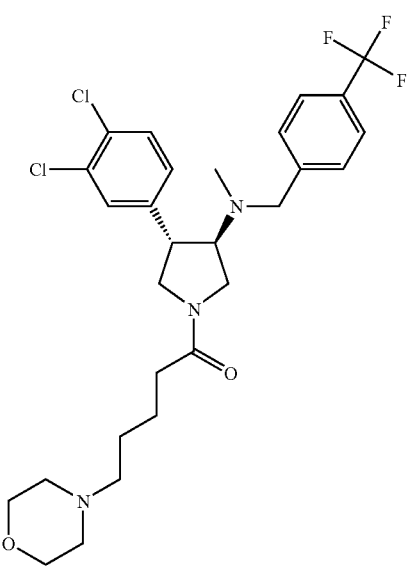

Coupling reaction according to general procedure I:
Pyrrolidine intermediate: [(3RS,4SR)-4-(3,4-Dichloro-phenyl)-pyrrolidin-3-yl]-methyl-(4-trifluoromethyl-benzyl)-amine (VIII-3),
Carboxylic acid: 5-Morpholin-4-yl-pentanoic acid (described in J. Molecular Structure 2001, 560, p. 261),
ES-MS m/e: 573.7 (M+H$^+$).

Example 85

5-Amino-1-{(3SR,4RS)-3-(3,4-dichloro-phenyl)-4-[(3-fluoro-4-trifluoromethyl-benzyl)-methyl-amino]-pyrrolidin-1-yl}-pentan-1-one

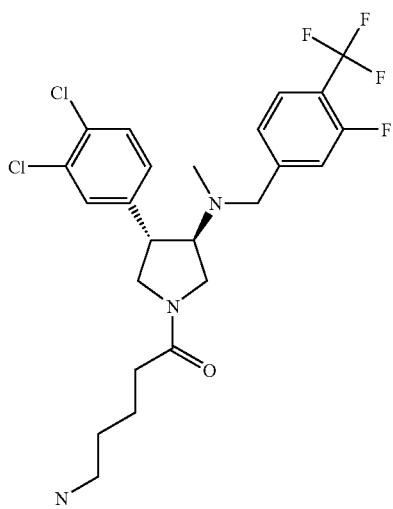

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1),
Amine: aqueous ammonia (commercially available),
ES-MS m/e: 519.9 (M+H$^+$).

Example 86

1-{(3SR,4RS)-3-(3,4-Dichloro-phenyl)-4-[(3-fluoro-4-trifluoromethyl-benz yl)-methyl-amino]pyrrolidin-1-yl}-5-methylamino-pentan-1-one

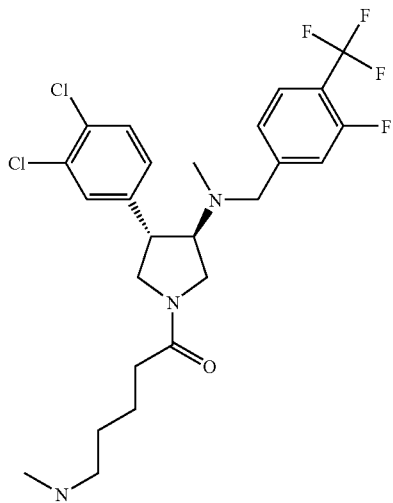

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1),
Amine: methyl amine (THF solution) (commercially available),
ES-MS m/e: 533.8 (M+H$^+$).

Example 87

1-{(3SR,4RS)-3-(3,4-Dichloro-phenyl)-4-[(3-fluoro-4-trifluoromethyl-benzyl)-methyl-amino]-pyrrolidin-1-yl}-5-dimethylamino-pentan-1-one

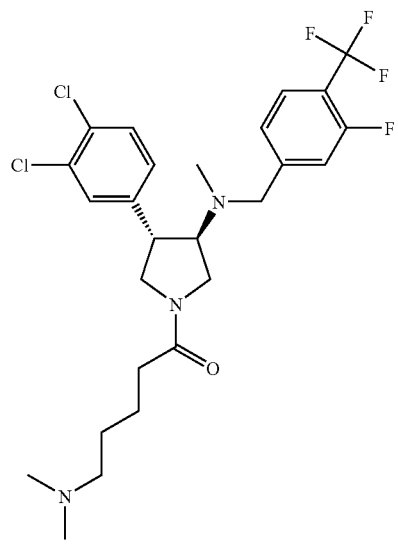

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1),
Amine: dimethyl-amine (commercially available),
ES-MS m/e: 547.9 (M+H$^+$).

Example 88

1-{(3SR,4RS)-3-(3,4-Dichloro-phenyl)-4-[(3-fluoro-4-trifluoromethyl-benzyl)-methyl-amino]-pyrrolidin-1-yl}-5-piperazin-1-yl-pentan-1-one

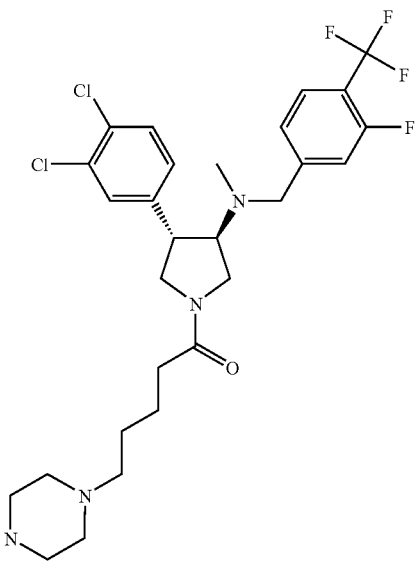

Nucleophilic substitution reaction according to general procedure VII:
Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1),
Amine: piperazine (commercially available),
ES-MS m/e: 588.8 (M+H$^+$).

Example 89

1-{(3SR,4RS)-3-(3,4-Dichloro-phenyl)-4-[(3-fluoro-4-trifluoromethyl-benzyl)-methyl-amino]-pyrrolidin-1-yl}-5-(4-methyl-piperazin-1-yl)-pentan-1-one

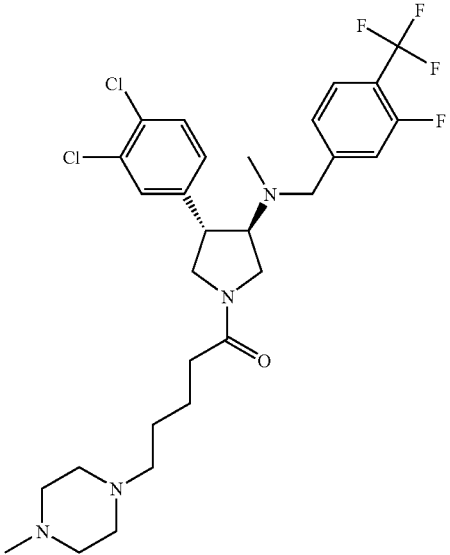

Nucleophilic substitution reaction according to general procedure VII:
Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1),
Amine: 1-Methyl-piperazine (commercially available),
ES-MS m/e: 602.8 (M+H$^+$).

Example 90

4-(5-{(3SR,4RS)-3-(3,4-Dichloro-phenyl)-4-[(3-fluoro-4-trifluoromethyl-benzyl)-methyl-amino]-pyrrolidin-1-yl}-5-oxo-pentyl)-piperazine-1-sulfonic acid dimethylamide

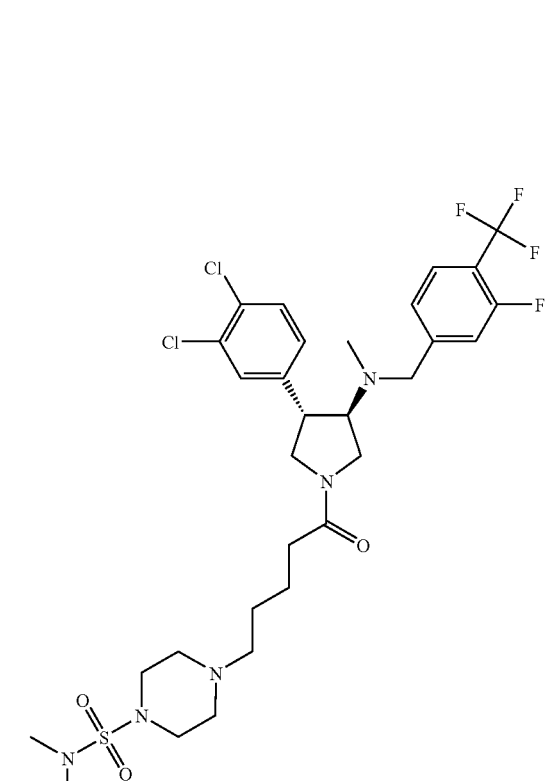

Nucleophilic substitution reaction according to general procedure VII:
Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1),
Amine: piperazine-1-sulfonic acid dimethylamide (commercially available),
ES-MS m/e: 695.8 (M+H$^+$).

Example 91

1-{(3SR,4RS)-3-(3,4-Dichloro-phenyl)-4-[(3-fluoro-4-trifluoromethyl-benzyl)-methyl-amino]-pyrrolidin-1-yl}-5-imidazol-1-yl-pentan-1-one

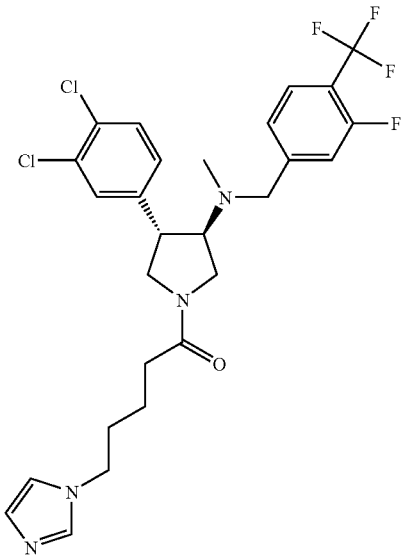

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1), Amine: 1H-Imidazole (commercially available), ES-MS m/e: 570.6 (M+H$^+$).

Example 92

1-{(3SR,4RS)-3-(3,4-Dichloro-phenyl)-4-[(3-fluoro-4-trifluoromethyl-benz yl)-methyl-amino]-pyrrolidin-1-yl}-5-pyrrolidin-1-yl-pentan-1-one

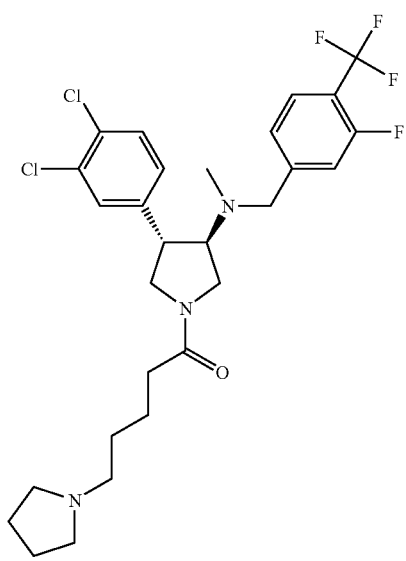

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1), Amine: pyrrolidine (commercially available), ES-MS m/e: 573.7 (M+H$^+$).

Example 93

(3SR,4RS)-3-(3,4-Dichloro-phenyl)-4-[(3-fluoro-4-trifluoromethyl-benzyl)-methyl-amino]-pyrrolidine-1-carboxylic acid 3-dimethylamino-propyl ester

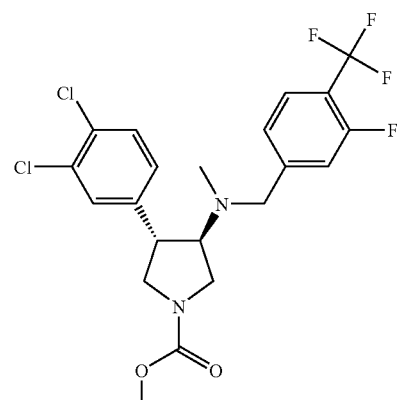

Nucleophilic substitution reaction according to general procedure VIII:

Pyrrolidine intermediate: (3SR,4RS)-3-(3,4-Dichloro-phenyl)-4-[(3-fluoro-4-trifluoromethyl-benzyl)-methyl-amino]-pyrrolidine-1-carboxylic acid 3-chloro-propyl ester (XVI-1), Amine: dimethyl-amine (commercially available), ES-MS m/e: 550.3 (M+H$^+$).

Example 94

(3SR,4RS)-3-(3,4-Dichloro-phenyl)-4-[(3-fluoro-4-trifluoromethyl-benzyl)-methyl-amino]-pyrrolidine-1-carboxylic acid 3-morpholin-4-yl-propyl ester

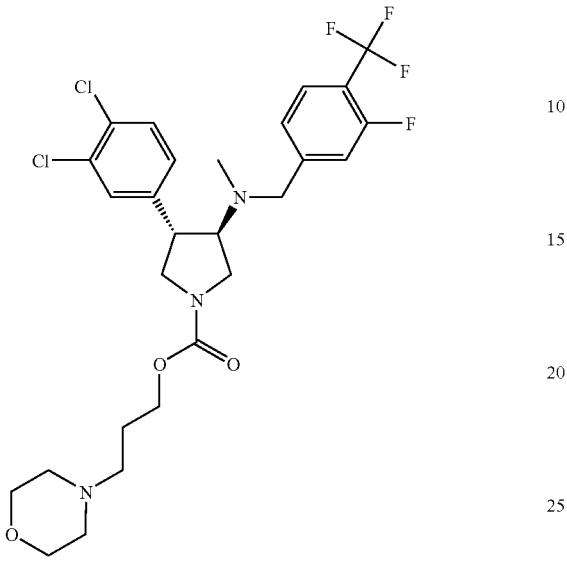

Nucleophilic substitution reaction according to general procedure VIII:
Pyrrolidine intermediate: (3SR,4RS)-3-(3,4-Dichloro-phenyl)-4-[(3-fluoro-4-trifluoromethyl-benzyl)-methyl-amino]-pyrrolidine-1-carboxylic acid 3-chloro-propyl ester (XVI-1),
Amine: morpholine (commercially available),
ES-MS m/e: 591.8 (M+H$^+$).

Example 95

1-{(3SR,4RS)-3-(3,4-Dichloro-phenyl)-4-[(3-fluoro-4-trifluoromethyl-benzyl)-methyl-amino]-pyrrolidin-1-yl}-6-pyridin-2-yl-hexane-1,6-dione

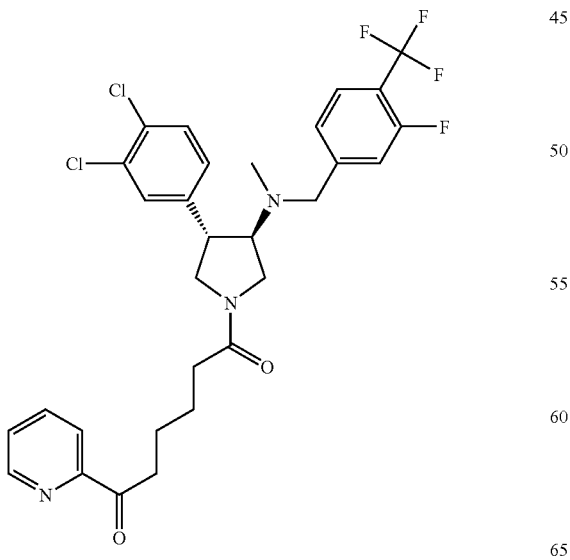

Coupling reaction according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-Oxo-6-pyridin-2-yl-hexanoic acid (Journal fuer Praktisher Chemie, 1966, 34, 272),
ES-MS m/e: 610.1 (M+H$^+$).

Example 96

1-{(3SR,4RS)-3-(3,4-Dichloro-phenyl)-4-[(3-fluoro-4-trifluoromethyl-benzyl)-methyl-amino]-pyrrolidin-1-yl}-6-(4-methoxy-phenyl)-hexane-1,6-dione

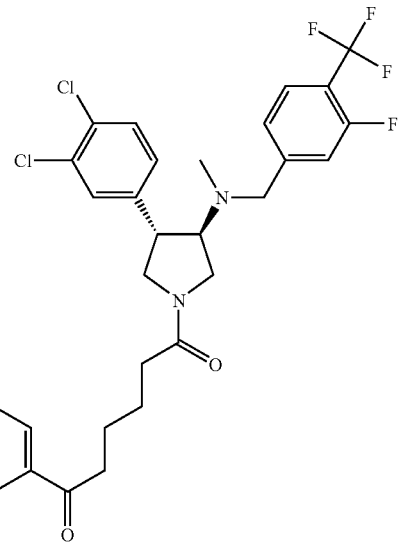

Coupling reaction according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-(4-Methoxy-phenyl)-6-oxo-hexanoic acid (commercially available),
ES-MS m/e: 611.2 (M+H$^+$).

Example 97

1-{(3SR,4RS)-3-(3,4-Dichloro-phenyl)-4-[(3-fluoro-4-trifluoromethyl-benzyl)-methyl-amino]-pyrrolidin-1-yl}-6-thiophen-2-yl-hexane-1,6-dione

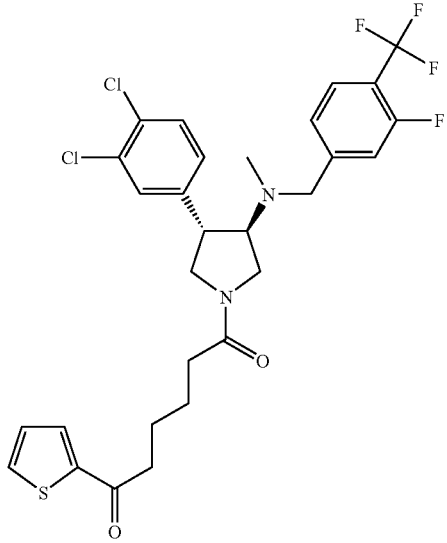

Coupling reaction according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 6-Oxo-6-thiophen-2-yl-hexanoic acid (commercially available), ES-MS m/e: 587.1 (M+H$^+$).

Example 98

6-{(3SR,4RS)-3-(3,4-Dichloro-phenyl)-4-[(3-fluoro-4-trifluoromethyl-benz yl)-methyl-amino]-pyrrolidin-1-yl}-6-oxo-hexanoic acid amide

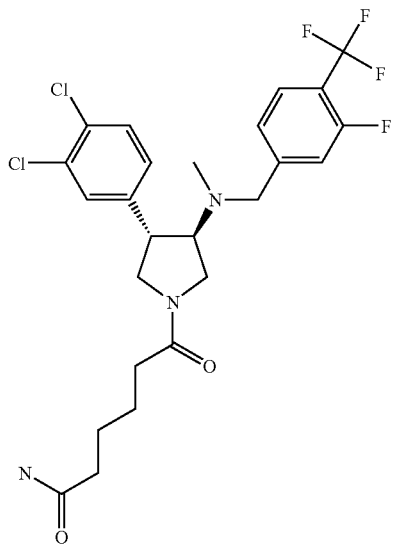

Coupling reaction according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 5-Carbamoyl-pentanoic acid (commercially available), ES-MS m/e: 548.2 (M+H$^+$).

Example 99

1-{(3S,4R)-3-(3,4-Dichloro-phenyl)-4-[(3-fluoro-4-trifluoromethyl-benzyl)-methyl-amino]-pyrrolidin-1-yl}-5-methoxy-pentan-1-one

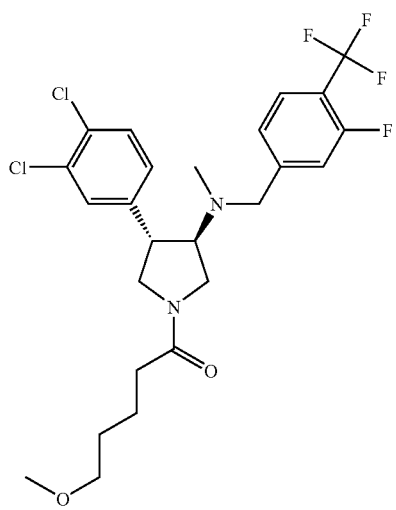

Coupling reaction according to general procedure 1:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 5-Methoxy-pentanoic acid (commercially available), ES-MS m/e: 535.1 (M+H$^+$).

Example 100

5-(4-Chloro-phenyl)-1-{(3SR,4RS)-3-(3,4-dichloro-phenyl)-4-[(3-fluoro-4-trifluoromethyl-benzyl)-methyl-amino]-pyrrolidin-1-yl}-pentan-1-one

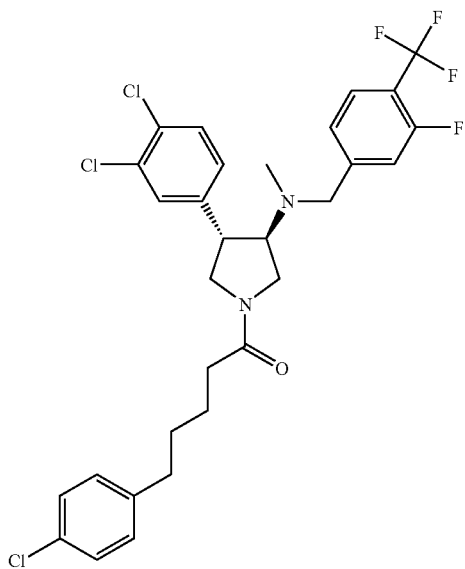

Coupling reaction according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 5-(4-Chloro-phenyl)-pentanoic acid (commercially available),
ES-MS m/e: 615.1 (M+H$^+$).

Example 101

4-{(3SR,4RS)-3-(3,4-Dichloro-phenyl)-4-[(3-fluoro-4-trifluoromethyl-benzyl)-methyl-amino]-pyrrolidin-1-yl}-N,N-dimethyl-4-oxo-butyramide

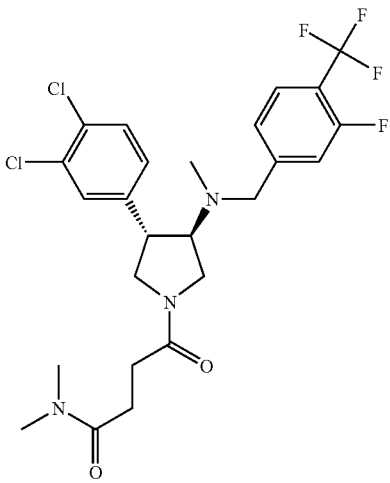

Coupling reaction according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: N,N-Dimethyl-succinamic acid (commercially available),
ES-MS m/e: 548.2 (M+H$^+$).

Example 102

6-{(3SR,4RS)-3-(3,4-Dichloro-phenyl)-4-[(3-fluoro-4-trifluoromethyl-benzyl)-methyl-amino]-pyrrolidin-1-yl}-6-oxo-hexanenitrile

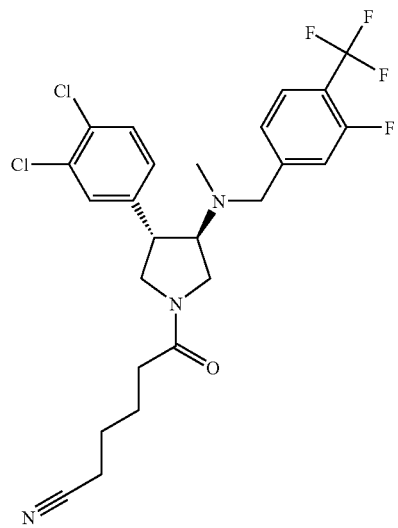

To a stirred solution of 5-bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1) (40 mg, 0.068 mmol) in DMF (2 ml) was added potassium cyanide (5.0 mg, 0.077 mmol) and 18 crown 6-ether (18 mg, 0.068 mmol). The reaction mixture was stirred at 40° C. overnight, concentrated under vacuo. The product was purified by preparation HPLC to yield 3.2 mg (9%) of the title product as a colorless oil. ES-MS m/e: 530.1 (M+H$^+$).

Example 103

(3SR,4RS)-3-(3,4-Dichloro-phenyl)-4-[(3-fluoro-4-trifluoromethyl-benzyl)-methyl-amino]-pyrrolidine-1-carboxylic acid 3-cyano-propyl ester

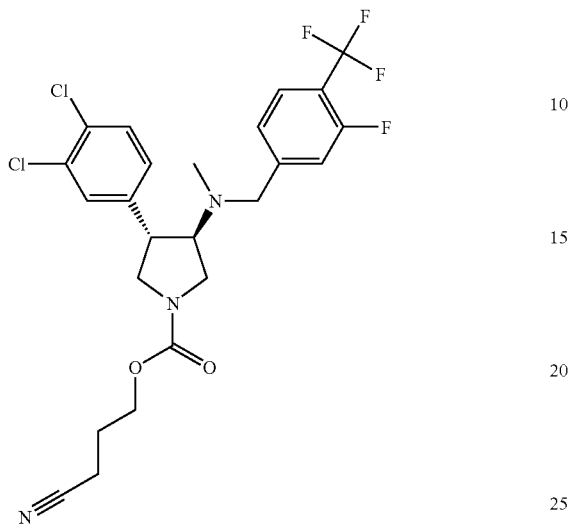

To a stirred solution of (3SR,4RS)-3-(3,4-dichloro-phenyl)-4-[(3-fluoro-4-trifluoromethyl-benzyl)-methyl-amino]-pyrrolidine-1-carboxylic acid 3-chloro-propyl ester (XVI-1) (40 mg, 0.068 mmol) in DMF (2 ml) was added potassium cyanide (5.0 mg, 0.077 mmol) and 18 crown 6-ether (18 mg, 0.068 mmol). The reaction mixture was stirred at 40° C. overnight, concentrated under vacuo. The product was purified by preparation HPLC to yield 18 mg (45%) of the title product as a colorless oil. ES-MS m/e: 532.1 (M+H$^+$).

Example 104

1-{(3SR,4RS)-3-(3,4-Dichloro-phenyl)-4-[(3-fluoro-4-trifluoromethyl-benzyl)-methyl-amino]-pyrrolidin-1-yl}-5-(1-methyl-piperidin-4-ylamino)-pentan-1-one

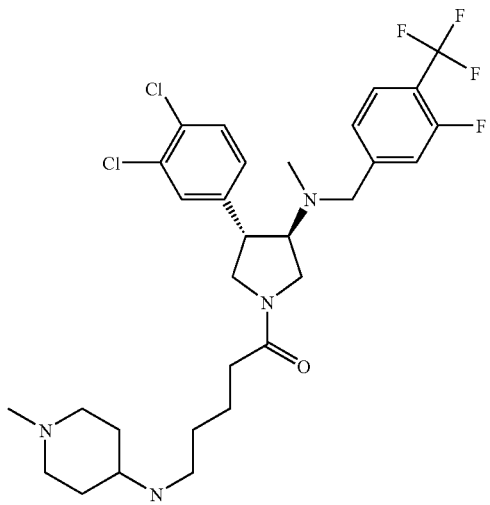

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1), Amine: 1-Methyl-piperidin-4-ylamine (commercially available), ES-MS m/e: 617.3 (M+H$^+$).

Example 105

N-[1-(5-{(3SR,4RS)-3-(3,4-Dichloro-phenyl)-4-[(3-fluoro-4-trifluoromethyl-benzyl)-methyl-amino]-pyrrolidin-1-yl}-5-oxo-pentyl)-piperidin-4-yl]-acetamide

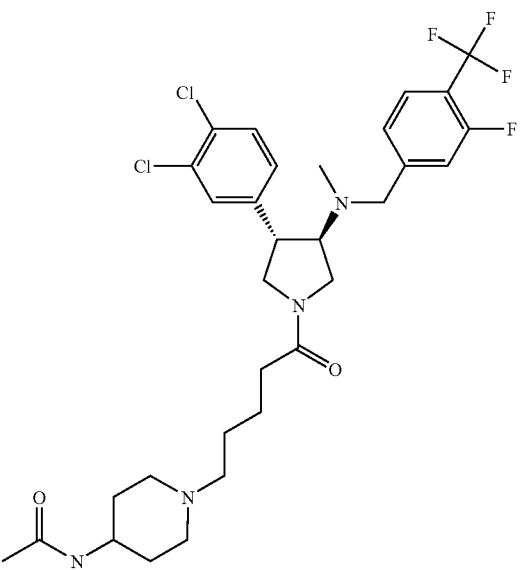

Nucleophilic substitution reaction according to general procedure VII:

Pyrrolidine intermediate: 5-Bromo-1-{(3SR,4RS)-3-(3,4-dichloro-phenyl)-4-[(3-fluoro-4-trifluoromethyl-benzyl)-methyl-amino]-pyrrolidin-1-yl}-pentan-1-one (XV-1), Amine: N-Piperidin-4-yl-acetamide (commercially available), ES-MS m/e: 645.4 (M+H$^+$).

Example 106

{(3SR,4RS)-3-(3-Chloro-phenyl)-4-[(3-fluoro-4-trifluoromethyl-benzyl)-methyl-amino]-pyrrolidin-1-yl}-(4-methanesulfonyl-piperazin-1-yl)-methanone

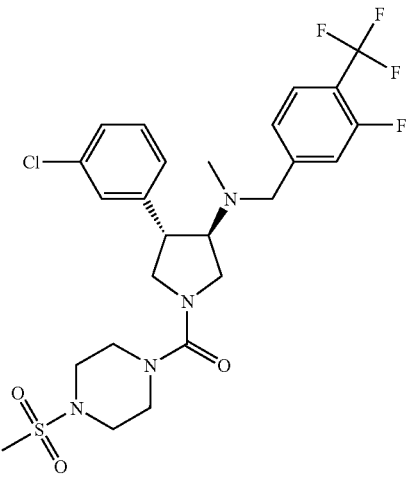

Coupling reaction according to general procedure II:
Pyrrolidine intermediate: [(3RS,4SR)-4-(3-Chloro-phenyl)-pyrrolidin-3-yl]-(3-fluoro-4-trifluoromethyl-benzyl)-methyl-amine (VIII-4),
Carbamoyl chloride: 4-Methanesulfonyl-piperazine-1-carbonyl chloride (described herein above),
ES-MS m/e: 576.8 (M+H$^+$).

Example 107

1-{(3SR,4RS)-3-(3-Chloro-phenyl)-4-[(3-fluoro-4-trifluoromethyl-benzyl)-methyl-amino]-pyrrolidin-1-yl}-5-morpholin-4-yl-pentan-1-one

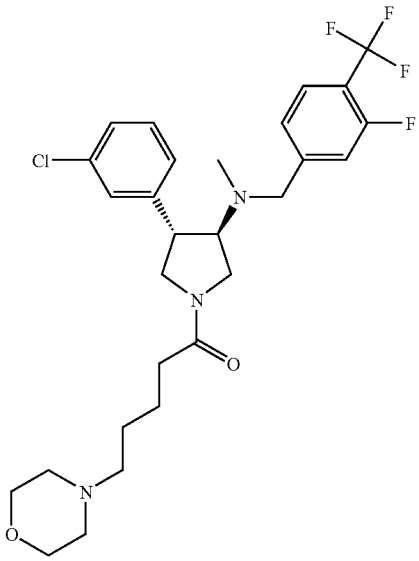

Coupling reaction according to general procedure II:
Pyrrolidine intermediate: [(3RS,4SR)-4-(3-Chloro-phenyl)-pyrrolidin-3-yl]-(3-fluoro-4-trifluoromethyl-benzyl)-methyl-amine (VIII-4),
Carboxylic acid: 5-Morpholin-4-yl-pentanoic acid (described in J. Molecular Structure 2001, 560, p. 261),
ES-MS m/e: 555.8 (M+H$^+$).

Example 108

{(3SR,4RS)-3-(3-Chloro-phenyl)-4-[methyl-(4-trifluoromethyl-benzyl)-amino]-pyrrolidin-1-yl}-(4-methanesulfonyl-piperazin-1-yl)-methanone

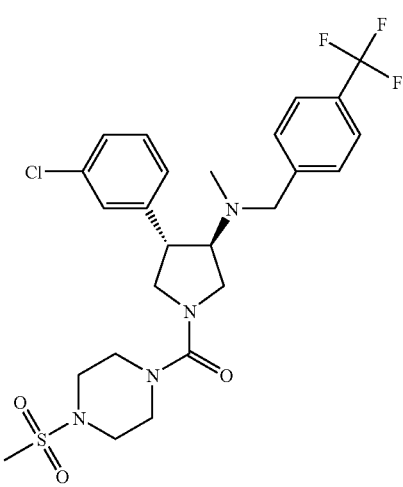

Coupling reaction according to general procedure II:
Pyrrolidine intermediate: [(3RS,4SR)-4-(3-Chloro-phenyl)-pyrrolidin-3-yl]-methyl-(4-trifluoromethyl-benzyl)-amine (VIII-5),
Carbamoyl chloride: 4-Methanesulfonyl-piperazine-1-carbonyl chloride (described herein above),
ES-MS m/e: 558.6 (M+H$^+$).

Example 109

1-{(3SR,4RS)-3-(3-Chloro-phenyl)-4-[methyl-(4-trifluoromethyl-benzyl)-amino]-pyrrolidin-1-yl}-5-morpholin-4-yl-pentan-1-one

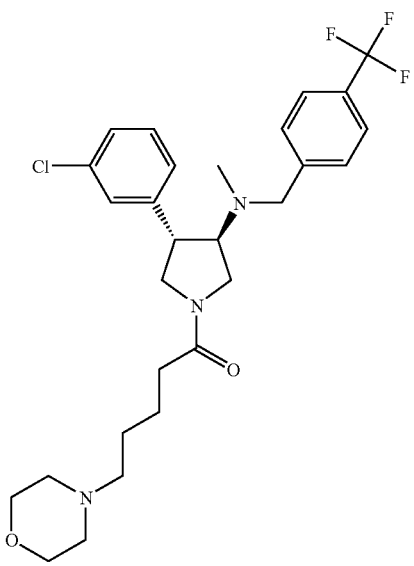

Coupling reaction according to general procedure II:
Pyrrolidine intermediate: [(3RS,4SR)-4-(3-Chloro-phenyl)-pyrrolidin-3-yl]-methyl-(4-trifluoromethyl-benzyl)-amine (VIII-5),
Carboxylic acid: 5-Morpholin-4-yl-pentanoic acid (described in J. Molecular Structure 2001, 560, p. 261),
ES-MS m/e: 537.9 (M+H⁺).

Example 110

1-{(3S,4R)-3-(3,4-Dichloro-phenyl)-4-[(3-fluoro-4-trifluoromethyl-benzyl)-methyl-amino]-pyrrolidin-1-yl}-3-morpholin-4-yl-propan-1-one

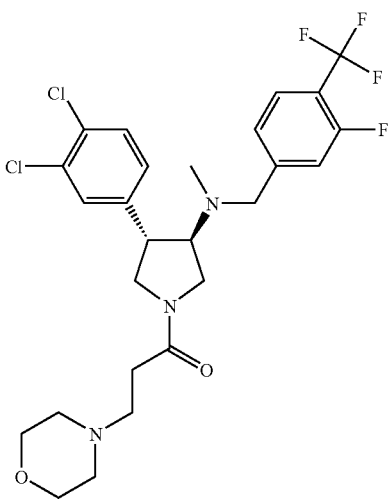

Coupling reaction according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 3-Morpholin-4-yl-propionic acid (commercially available),
ES-MS m/e: 561.8 (M+H⁺).

Example 111

1-{(3SR,4RS)-3-(3-Chloro-phenyl)-4-[methyl-(4-trifluoromethyl-benzyl)-amino]-pyrrolidin-1-yl}-3-morpholin-4-yl-propan-1-one

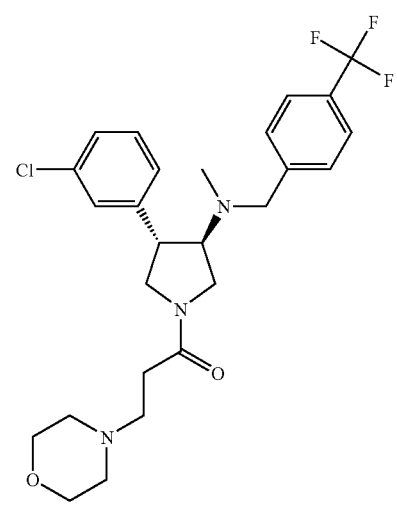

Coupling reaction according to general procedure I:
Pyrrolidine intermediate: [(3RS,4SR)-4-(3-Chloro-phenyl)-pyrrolidin-3-yl]-methyl-(4-trifluoromethyl-benzyl)-amine (VIII-5),
Carboxylic acid: 3-Morpholin-4-yl-propionic acid (commercially available),
ES-MS m/e: 510.1 (M+H⁺).

Example 112

1-{(3SR,4RS)-3-(3-Chloro-phenyl)-4-[(3-fluoro-4-trifluoromethyl-benzyl)-methyl-amino]-pyrrolidin-1-yl}-3-morpholin-4-yl-propan-1-one

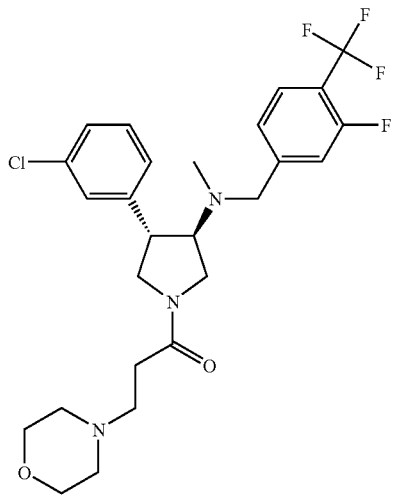

Coupling reaction according to general procedure I:
Pyrrolidine intermediate: [(3RS,4SR)-4-(3-Chloro-phenyl)-pyrrolidin-3-yl]-(3-fluoro-4-trifluoromethyl-benzyl)-methyl-amine (VIII-4),
Carboxylic acid: 3-Morpholin-4-yl-propionic acid (commercially available),
ES-MS m/e: 527.7 (M+H$^+$).

Example 113

1-{(3SR,4RS)-3-(3,4-Dichloro-phenyl)-4-[(3-fluoro-4-trifluoromethyl-benzyl)-methyl-amino]-pyrrolidin-1-yl}-2-morpholin-4-yl-ethanone

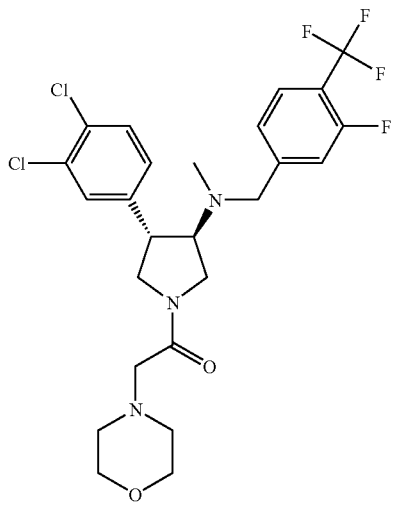

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: Morpholine (commercially available),
ES-MS m/e: 547.8 (M+H$^+$).

Example 114

1-{(3SR,4RS)-3-(3,4-Dichloro-phenyl)-4-[(3-fluoro-4-trifluoromethyl-benzyl)-methyl-amino]-pyrrolidin-1-yl}-2-(4-methyl-piperazin-1-yl)-ethanone

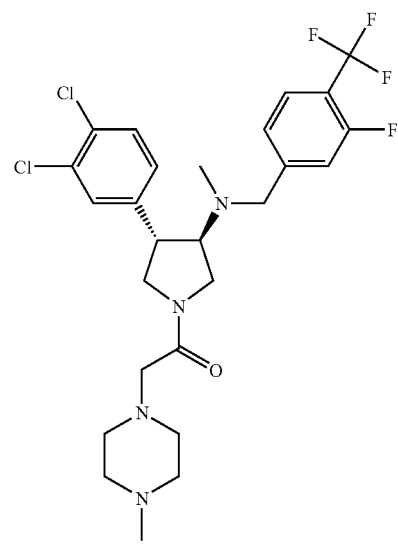

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 1-Methyl-piperazine (commercially available),
ES-MS m/e: 560.7 (M+H$^+$).

Example 115

1-{(3SR,4RS)-3-(3,4-Dichloro-phenyl)-4-[(3-fluoro-4-trifluoromethyl-benzyl)-methyl-amino]-pyrrolidin-1-yl}-2-(4-methanesulfonyl-piperazin-1-yl)-ethanone

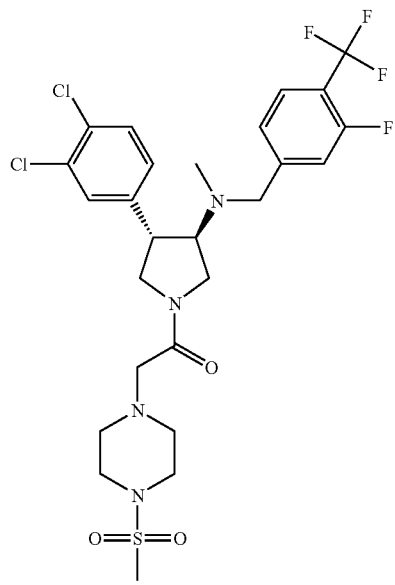

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 1-Methanesulfonyl-piperazine (commercially available),
ES-MS m/e: 624.5 (M+H$^+$).

Example 116

4-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperazine-1-sulfonic acid dimethylamide

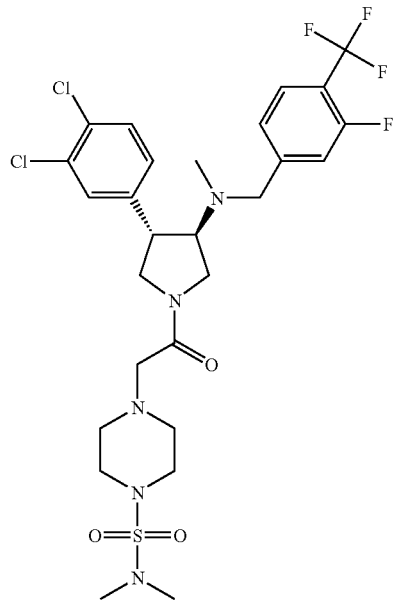

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: piperazine-1-sulfonic acid dimethylamide (commercially available),
ES-MS m/e: 653.7 (M–H$^+$).

Example 117

1-{(3SR,4RS)-3-(3,4-Dichloro-phenyl)-4-[(3-fluoro-4-trifluoromethyl-benzyl)-methyl-amino]-pyrrolidin-1-yl}-2-[4-(2-dimethylamino-ethyl)-piperazin-1-yl]-ethanone

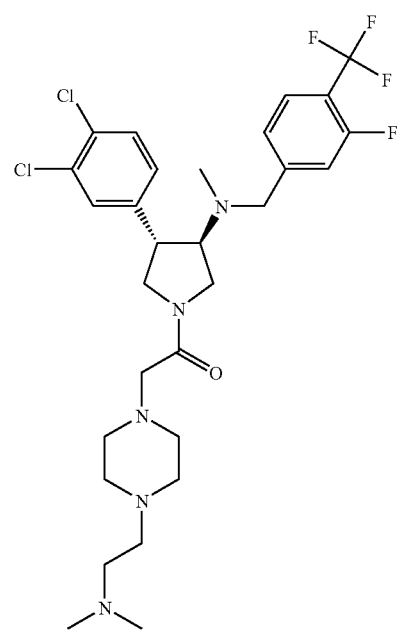

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: Dimethyl-(2-piperazin-1-yl-ethyl)-amine (commercially available),
ES-MS m/e: 617.8 (M+H$^+$).

Example 118

3-[4-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperazin-1-yl]-propionitrile

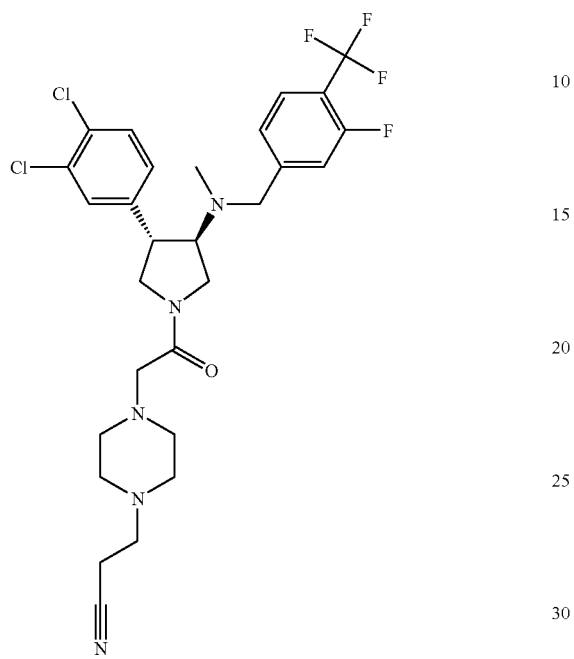

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 3-piperazin-1-yl-propionitrile (commercially available),
ES-MS m/e: 599.7 (M+H$^+$).

Example 119

1-{(3SR,4RS)-3-(3,4-Dichloro-phenyl)-4-[(3-fluoro-4-trifluoromethyl-benzyl)-methyl-amino]-pyrrolidin-1-yl}-2-(2-hydroxy-ethylamino)-ethanone

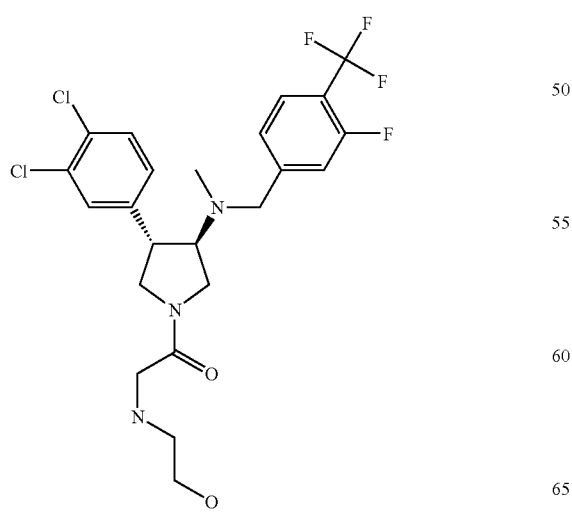

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 2-Amino-ethanol (commercially available),
ES-MS m/e: 521.9 (M+H$^+$).

Example 120

1-{(3SR,4RS)-3-(3,4-Dichloro-phenyl)-4-[(3-fluoro-4-trifluoromethyl-benzyl)-methyl-amino]-pyrrolidin-1-yl}-2-(3-hydroxy-propylamino)-ethanone

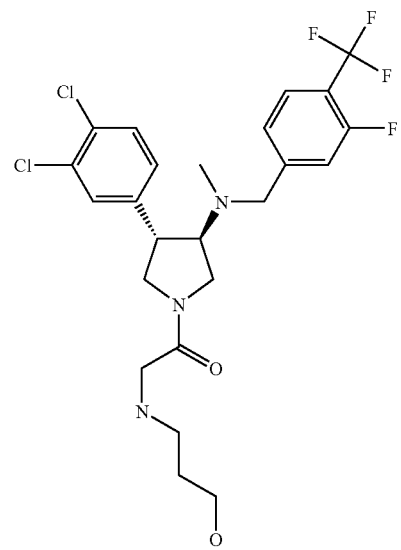

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 3-Amino-propan-1-ol (commercially available),
ES-MS m/e: 535.8 (M+H$^+$).

Example 121

1-{(3SR,4RS)-3-(3,4-Dichloro-phenyl)-4-[(3-fluoro-4-trifluoromethyl-benzyl)-methyl-amino]-pyrrolidin-1-yl}-2-[(2-hydroxy-ethyl)-methyl-amino]-ethanone

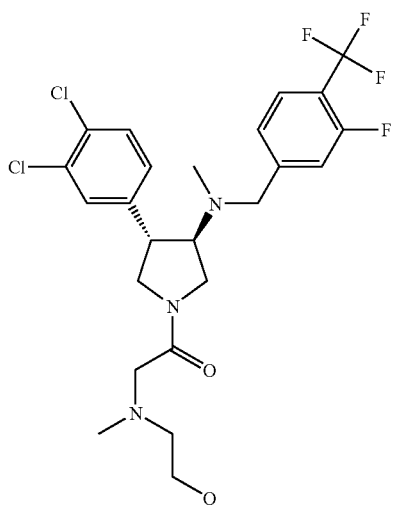

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 2-Methylamino-ethanol (commercially available),
ES-MS m/e: 535.8 (M+H$^+$).

Example 122

1-{(3SR,4RS)-3-(3,4-Dichloro-phenyl)-4-[(3-fluoro-4-trifluoromethyl-benzyl)-methyl-amino]-pyrrolidin-1-yl}-2-dimethylamino-ethanone

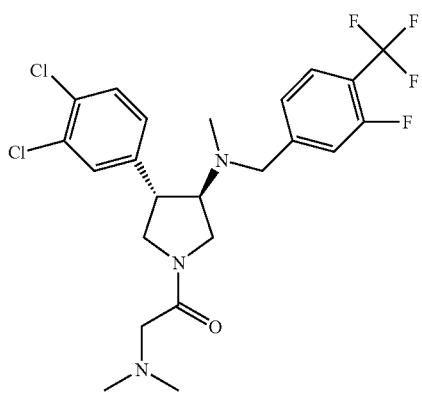

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: Dimethyl-amine (commercially available),
ES-MS m/e: 505.9 (M+H$^+$).

Example 123

1-{(3SR,4RS)-3-(3,4-Dichloro-phenyl)-4-[(3-fluoro-4-trifluoromethyl-benzyl)-methyl-amino]-pyrrolidin-1-yl}-2-[(2-dimethylamino-ethyl)-methyl-amino]-ethanone

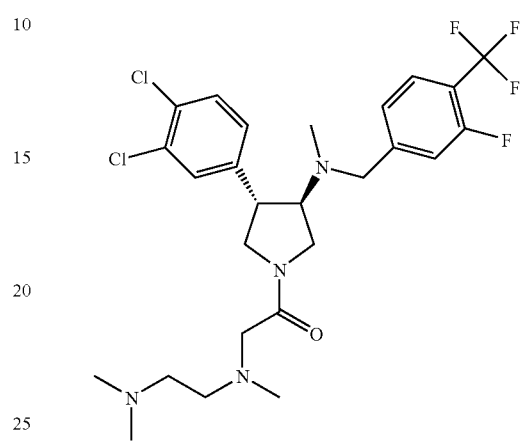

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N,N,N'-Trimethyl-ethane-1,2-diamine (commercially available),
ES-MS m/e: 562.9 (M+H$^+$).

Example 124

1-{(3SR,4RS)-3-(3,4-Dichloro-phenyl)-4-[(3-fluoro-4-trifluoromethyl-benzyl)-methyl-amino]-pyrrolidin-1-yl}-2-(2-dimethylamino-ethylamino)-ethanone

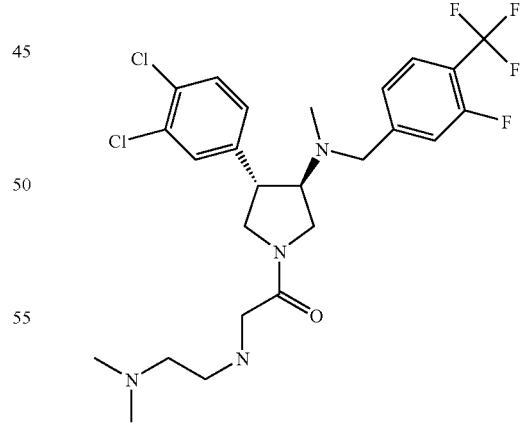

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N,N-Dimethyl-ethane-1,2-diamine (commercially available),
ES-MS m/e: 549.7 (M+H$^+$).

Example 125

1-{(3SR,4RS)-3-(3,4-Dichloro-phenyl)-4-[(3-fluoro-4-trifluoromethyl-benzyl)-methyl-amino]-pyrrolidin-1-yl}-2-(3-dimethylamino-propylamino)-ethanone

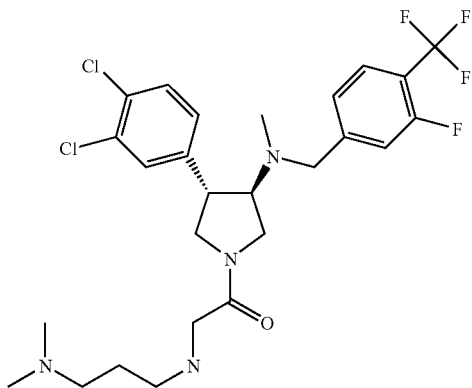

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N,N-Dimethyl-propane-1,3-diamine (commercially available),
ES-MS m/e: 563.2 (M+H$^+$).

Example 126

1-{(3SR,4RS)-3-(3,4-Dichloro-phenyl)-4-[(3-fluoro-4-trifluoromethyl-benzyl)-methyl-amino]-pyrrolidin-1-yl}-2-[(3-dimethylamino-propyl)-methyl-amino]-ethanone

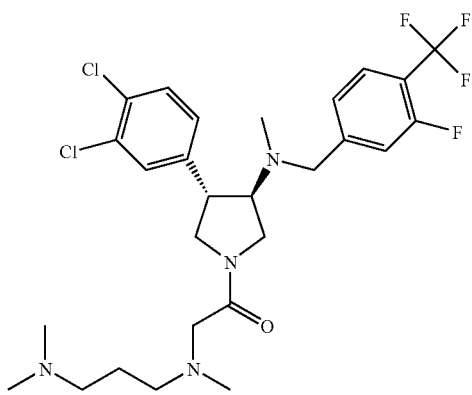

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N,N,N'-Trimethyl-propane-1,3-diamine (commercially available),
ES-MS m/e: 576.8 (M+H$^+$).

Example 127

3-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethylamino)-propionitrile

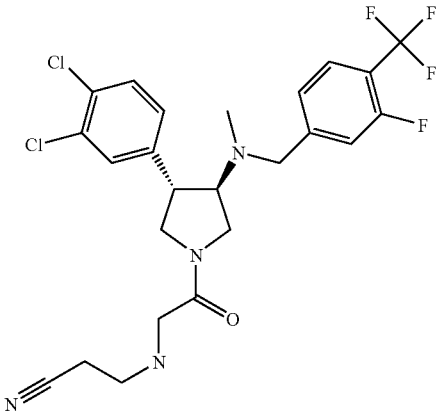

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 3-Amino-propionitrile (commercially available),
ES-MS m/e: 530.8 (M+H$^+$).

Example 128

3-[(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-methyl-amino]-propionitrile

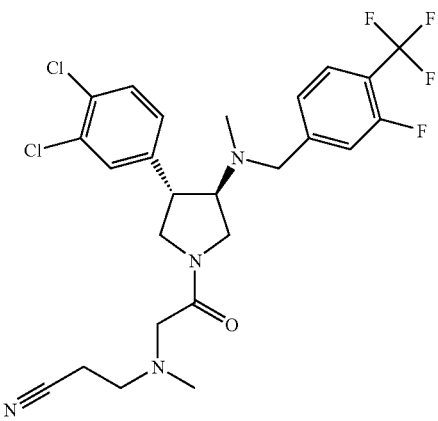

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 3-Methylamino-propionitrile (commercially available),
ES-MS m/e: 544.9 (M+H$^+$).

Example 129

1-{(3SR,4RS)-3-(3,4-Dichloro-phenyl)-4-[(3-fluoro-4-trifluoromethyl-benzyl)-methyl-amino]-pyrrolidin-1-yl}-2-[4-(3-hydroxy-propyl)-piperazin-1-yl]-ethanone

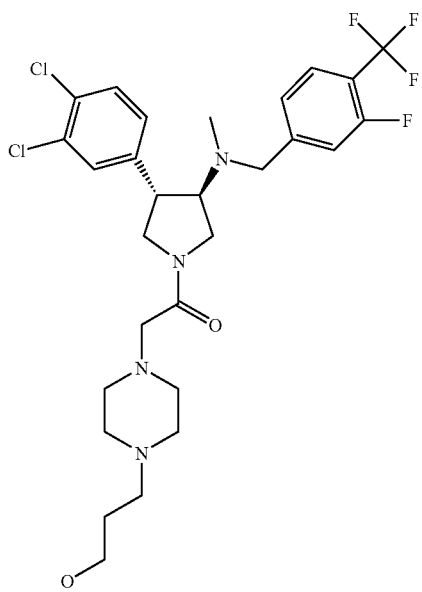

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 3-piperazin-1-yl-propan-1-ol (commercially available),
ES-MS m/e: 605.3 (M+H$^+$).

Example 130

1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperidine-4-carbonitrile

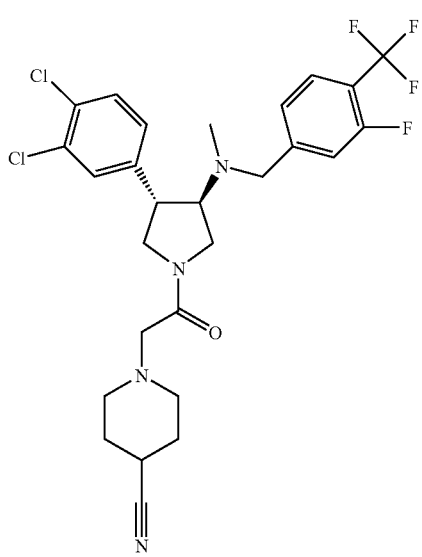

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: Piperidine-4-carbonitrile (commercially available),
ES-MS m/e: 570.7 (M+H$^+$).

Example 131

1-{(3SR,4RS)-3-(3,4-Dichloro-phenyl)-4-[(3-fluoro-4-trifluoromethyl-benzyl)-methyl-amino]-pyrrolidin-1-yl}-2-piperazin-1-yl-ethanone

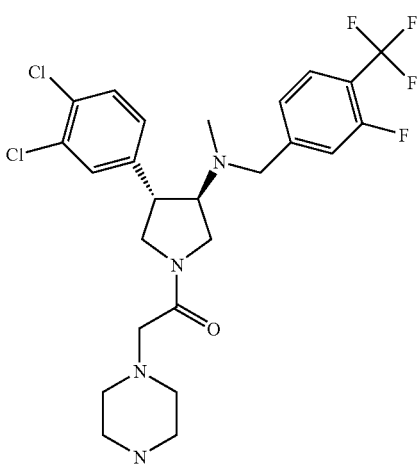

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: piperazine (commercially available),
ES-MS m/e: 546.7 (M+H$^+$).

Example 132

1-{(3SR,4RS)-3-(3,4-Dichloro-phenyl)-4-[(3-fluoro-4-trifluoromethyl-benzyl)-methyl-amino]-pyrrolidin-1-yl}-2-(4-hydroxy-piperidin-1-yl)-ethanone

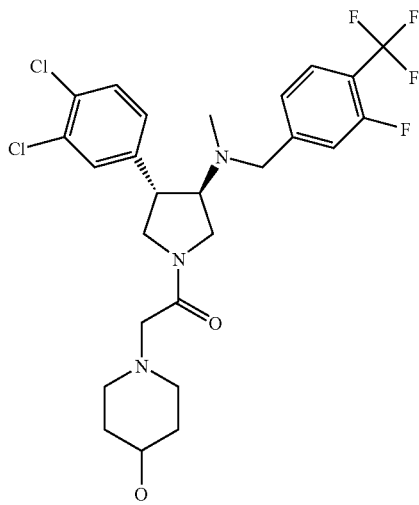

Coupling reaction according to general procedure VI:

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)

Amine: Piperidin-4-ol (commercially available),

ES-MS m/e: 561.8 (M+H$^+$).

Example 133

N-[(S)-1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-pyrrolidin-3-yl]-acetamide

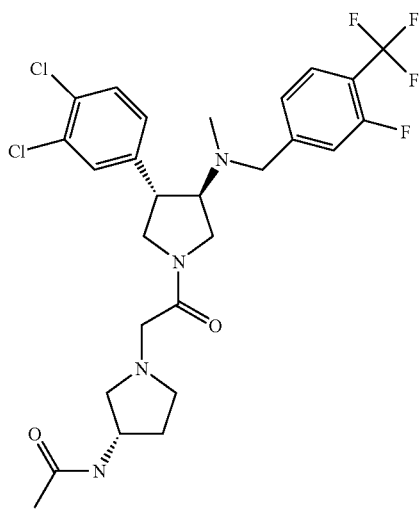

Coupling reaction according to general procedure VI:

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)

Amine: (S)-N-Pyrrolidin-3-yl-acetamide (commercially available),

ES-MS m/e: 588.8 (M+H$^+$).

Example 134

N-[(R)-1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-pyrrolidin-3-yl]-acetamide

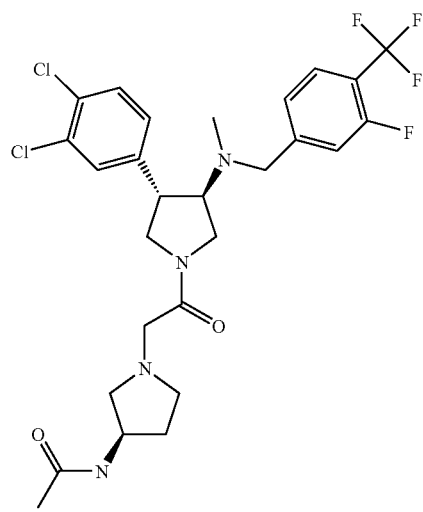

Coupling reaction according to general procedure VI:

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)

Amine: (R)-N-Pyrrolidin-3-yl-acetamide (commercially available),

ES-MS m/e: 588.8 (M+H$^+$).

Example 135

1-{(3S,4R)-3-(3,4-Dichloro-phenyl)-4-[(3-fluoro-4-trifluoromethyl-benzyl)-methyl-amino]-pyrrolidin-1-yl}-2-(1,1-dioxo-$\lambda^6$-thiomorpholin-4-yl)-ethanone

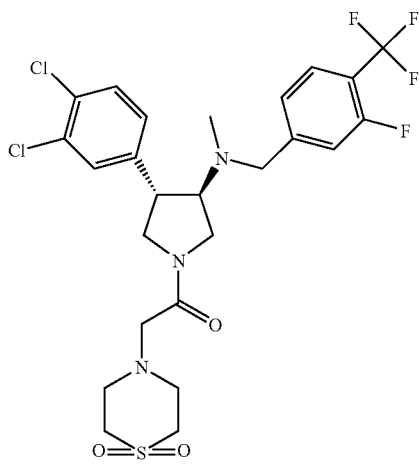

Coupling reaction according to general procedure VI:

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)

Amine: Thiomorpholine 1,1-dioxide (commercially available),

ES-MS m/e: 595.6 (M+H$^+$).

Example 136

1-{(3SR,4RS)-3-(3,4-Dichloro-phenyl)-4-[(3-fluoro-4-trifluoromethyl-benzyl)-methyl-amino]-pyrrolidin-1-yl}-2-(4-dimethylamino-piperidin-1-yl)-ethanone

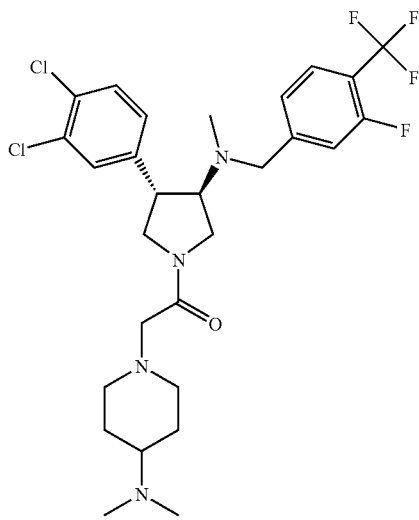

Coupling reaction according to general procedure VI:

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)

Amine: Dimethyl-piperidin-4-yl-amine (commercially available),

ES-MS m/e: 588.8 (M+H$^+$).

Example 137

N-[1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperidin-4-yl]-acetamide

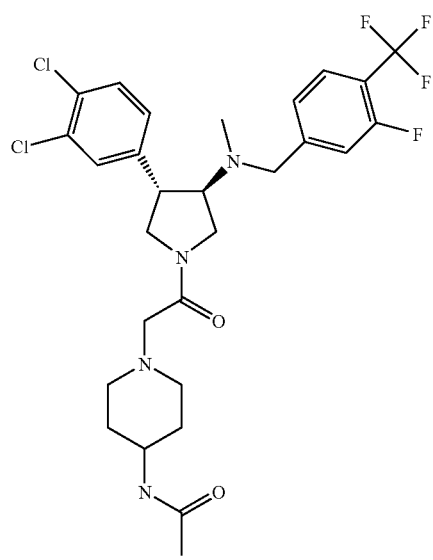

Coupling reaction according to general procedure VI:

2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)

Amine: N-Piperidin-4-yl-acetamide (commercially available),

ES-MS m/e: 602.8 (M+H$^+$).

Example 138

2-(4-Acetyl-piperazin-1-yl)-1-{(3SR,4RS)-3-(3,4-dichloro-phenyl)-4-[(3-fluoro-4-trifluoromethyl-benzyl)-methyl-amino]-pyrrolidin-1-yl}-ethanone

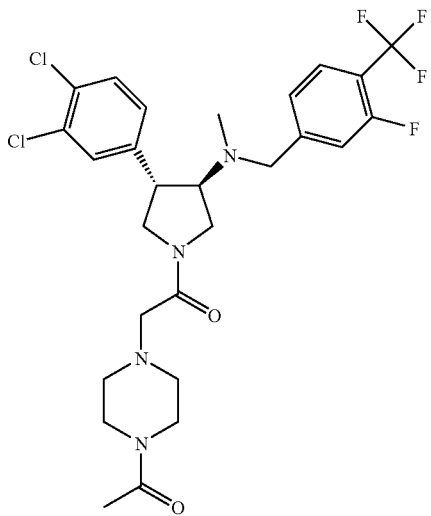

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 1-piperazin-1-yl-ethanone (commercially available),
ES-MS m/e: 588.8 (M+H$^+$).

Example 139

1-{(3SR,4RS)-3-(3,4-Dichloro-phenyl)-4-[(3-fluoro-4-trifluoromethyl-benzyl)-methyl-amino]-pyrrolidin-1-yl}-2-(3,5-dimethyl-piperazin-1-yl)-ethanone

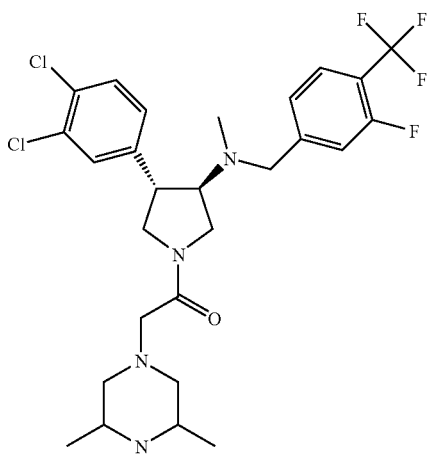

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 2,6-Dimethyl-piperazine (commercially available),
ES-MS m/e: 574.9 (M+H$^+$).

Example 140

1-{(3SR,4RS)-3-(3,4-Dichloro-phenyl)-4-[(3-fluoro-4-trifluoromethyl-benzyl)-methyl-amino]-pyrrolidin-1-yl}-2-((S)-3-methyl-piperazin-1-yl)-ethanone

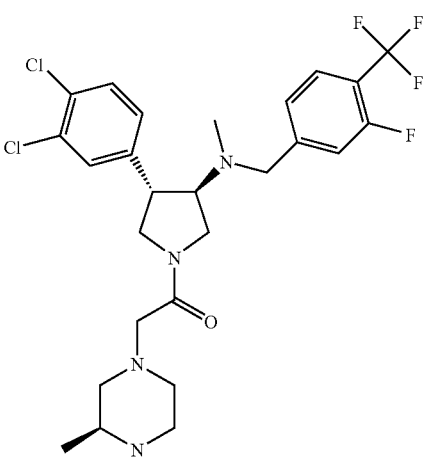

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: (S)-2-Methyl-piperazine (commercially available),
ES-MS m/e: 560.8 (M+H$^+$).

Example 141

1-{(3SR,4RS)-3-(3,4-Dichloro-phenyl)-4-[(3-fluoro-4-trifluoromethyl-benzyl)-methyl-amino]-pyrrolidin-1-yl}-2-((R)-3-methyl-piperazin-1-yl)-ethanone

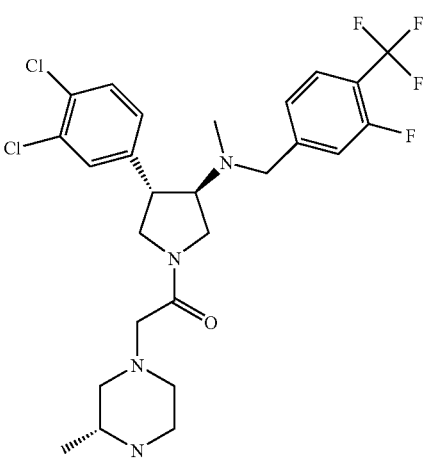

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: (R)-2-Methyl-piperazine (commercially available),
ES-MS m/e: 560.8 (M+H$^+$).

Example 142

1-{(3SR,4RS)-3-(3,4-Dichloro-phenyl)-4-[(3-fluoro-4-trifluoromethyl-benzyl)-methyl-amino]-pyrrolidin-1-yl}-2-(2,6-dimethyl-morpholin-4-yl)-ethanone

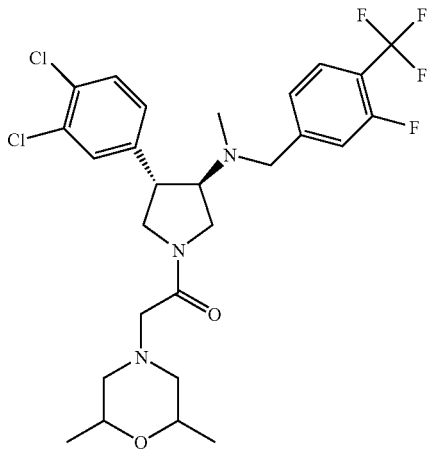

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 2,6-Dimethyl-morpholine (commercially available),
ES-MS m/e: 575.8 (M+H$^+$).

Example 143

N-[1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperidin-4-yl]-methanesulfonamide

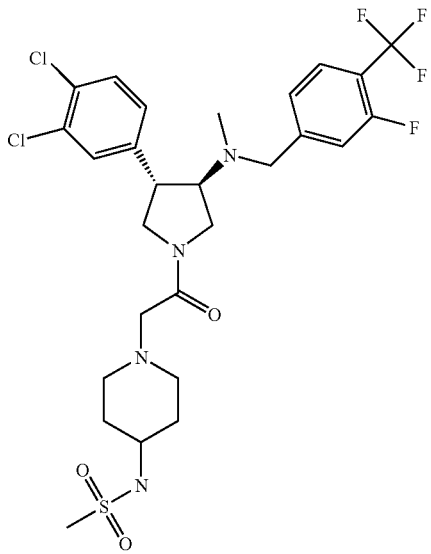

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N-Piperidin-4-yl-methanesulfonamide (commercially available),
ES-MS m/e: 638.9 (M+H$^+$).

Example 144

N-[1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperidin-4-yl]-N-methyl-methanesulfonamide

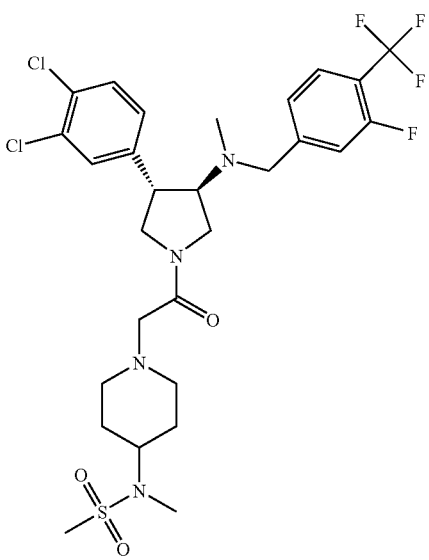

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N-Methyl-N-piperidin-4-yl-methanesulfonamide (described in WO20080707740),
ES-MS m/e: 652.7 (M+H$^+$).

Example 145

4-[1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperidin-4-yl]-morpholin-3-one

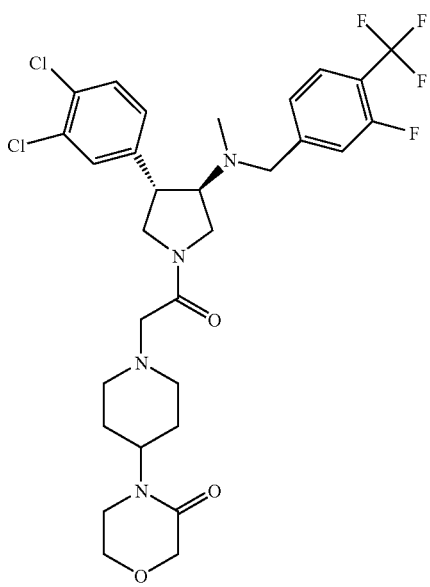

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: 4-Piperidin-4-yl-morpholin-3-one (described in WO2006/055951),
ES-MS m/e: 644.8 (M+H$^+$).

Example 146

1'-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-[1,4']bipiperidinyl-2-one

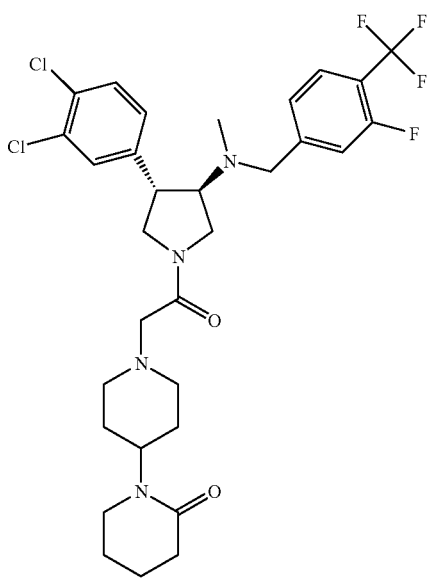

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: [1,4']Bipiperidinyl-2-one (described in WO2006/055951),
ES-MS m/e: 642.8 (M+H$^+$).

Example 147

N-[1-(2-{(3SR,4RS)-3-(3,4-Dichloro-phenyl)-4-[(3-fluoro-4-trifluoromethyl-benzyl)-methyl-amino]-pyrrolidin-1-yl}-2-oxo-ethyl)-piperidin-4-yl]-N-methyl-acetamide

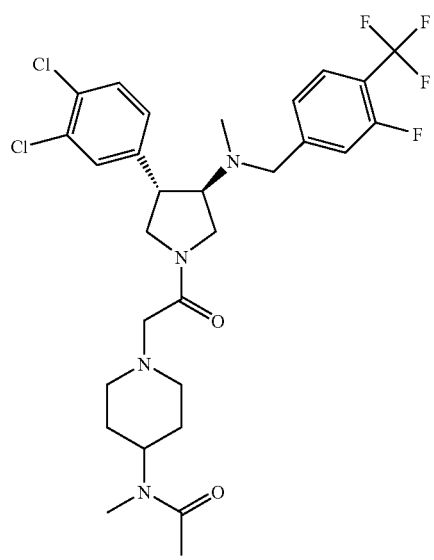

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: N-Methyl-N-piperidin-4-yl-acetamide (commercially available),
ES-MS m/e: 617.2 (M+H$^+$).

Example 148

1-{(3SR,4RS)-3-(3,4-Dichloro-phenyl)-4-[(3-fluoro-4-trifluoromethyl-benzyl)-methyl-amino]-pyrrolidin-1-yl}-2-(1S,4R)-2-oxa-5-aza-bicyclo[2.2.1]hept-5-yl-ethanone

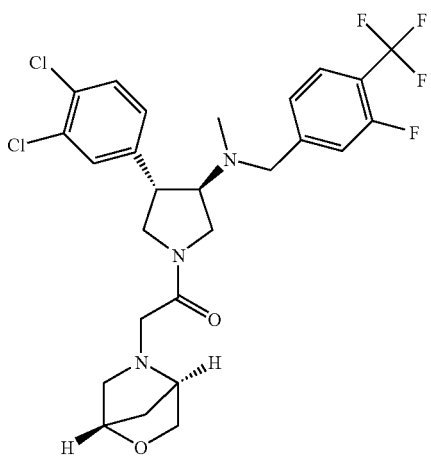

Coupling reaction according to general procedure VI:
2-Bromo-1-{(3SR,4RS)-3-(3,4-dichloro-phenyl)-4-[(3-fluoro-4-trifluoromethyl-benzyl)-methyl-amino]-pyrrolidin-1-yl}-ethanone (XIV-1)
Amine: (1S,4R)-2-Oxa-5-aza-bicyclo[2.2.1]heptane (commercially available),
ES-MS m/e: 561.8 (M+H$^+$).

Example 149

{(3SR,4RS)-3-(3,4-Dichloro-phenyl)-4-[(3-fluoro-4-trifluoromethyl-benzyl)-methyl-amino]-pyrrolidin-1-yl}-[1-(1-methyl-cyclopropanecarbonyl)-piperidin-4-yl]-methanone

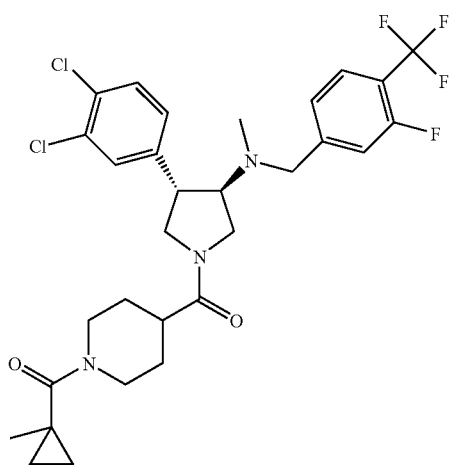

Reductive amination according to general procedure III:
Pyrrolidine intermediate: [(3SR,4RS)-3-(3,4-Dichloro-phenyl)-4-methylamino-pyrrolidin-1-yl]-[1-(1-methyl-cyclopropanecarbonyl)-piperidin-4-yl]-methanone (XII-4),
Aldehyde: 3-Fluoro-4-trifluoromethyl-benzaldehyde (commercially available),
ES-MS m/e: 614.3 (M+H$^+$)

Experimental Procedures

As mentioned earlier, the compounds of formula I and their pharmaceutically usable addition salts possess valuable pharmacological properties. The compounds of the present invention are antagonists of neurokinin 3 (NK-3) receptors. The compounds were investigated in accordance with the tests given hereinafter.

Experimental Procedure

The compounds were investigated in accordance with the tests given hereinafter
[$^3$H]SR142801 Competition Binding Assay
hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H]SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual K$_i$ values was calculated.

Results of some of the compounds of the invention with a hNK-3 receptor affinity<0.10 µM are shown in the following table 1.

TABLE 1

| Example | Data K$_i$ [µM] |
|---------|-----------------|
| 17 | 0.0909 |
| 19 | 0.0807 |
| 23 | 0.091 |
| 26 | 0.0825 |
| 27 | 0.078 |
| 29 | 0.0699 |

TABLE 1-continued

| Example | Data $K_i$ [μM] |
|---|---|
| 30 | 0.0284 |
| 31 | 0.0083 |
| 32 | 0.0333 |
| 33 | 0.0336 |
| 34 | 0.0322 |
| 36 | 0.0526 |
| 37 | 0.0762 |
| 43 | 0.0849 |
| 47 | 0.0691 |
| 51 | 0.0173 |
| 52 | 0.0713 |
| 56 | 0.022 |
| 57 | 0.0748 |
| 59 | 0.0154 |
| 60 | 0.0036 |
| 62 | 0.011 |
| 63 | 0.0086 |
| 64 | 0.0028 |
| 65 | 0.0041 |
| 66 | 0.003 |
| 67 | 0.0062 |
| 68 | 0.0059 |
| 69 | 0.0047 |
| 70 | 0.0105 |
| 71 | 0.0134 |
| 72 | 0.0027 |
| 73 | 0.0019 |
| 74 | 0.0054 |
| 75 | 0.0046 |
| 76 | 0.0018 |
| 77 | 0.0268 |
| 78 | 0.0048 |
| 79 | 0.0019 |
| 80 | 0.0208 |
| 81 | 0.0146 |
| 82 | 0.0397 |
| 83 | 0.006 |
| 84 | 0.0155 |
| 86 | 0.0976 |
| 87 | 0.0512 |
| 88 | 0.0247 |
| 89 | 0.0269 |
| 90 | 0.0086 |
| 91 | 0.0572 |
| 92 | 0.0466 |
| 95 | 0.0243 |
| 98 | 0.0527 |
| 99 | 0.0366 |
| 102 | 0.0708 |
| 105 | 0.0622 |
| 107 | 0.0812 |
| 110 | 0.0267 |
| 113 | 0.0457 |
| 114 | 0.0402 |
| 115 | 0.013 |
| 116 | 0.0169 |
| 117 | 0.0193 |
| 118 | 0.0112 |
| 124 | 0.0964 |
| 125 | 0.0768 |
| 126 | 0.0805 |
| 127 | 0.0997 |
| 128 | 0.072 |
| 129 | 0.0171 |
| 130 | 0.0254 |
| 131 | 0.0334 |
| 132 | 0.0263 |
| 133 | 0.0232 |
| 134 | 0.0432 |
| 135 | 0.0437 |
| 136 | 0.0189 |
| 137 | 0.0087 |
| 138 | 0.0088 |
| 139 | 0.0249 |
| 140 | 0.0479 |
| 141 | 0.0597 |
| 142 | 0.0197 |
| 143 | 0.012 |
| 144 | 0.0059 |
| 145 | 0.0137 |
| 146 | 0.0149 |
| 147 | 0.0138 |
| 148 | 0.0251 |
| 149 | 0.0031 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula I

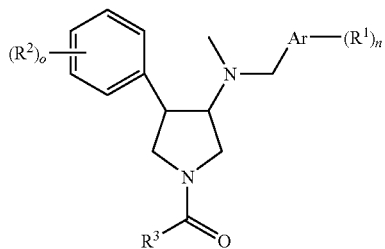

wherein
Ar is aryl;
R$^1$ is hydrogen, halogen, lower alkyl, lower alkoxy, lower alkyl substituted by halogen, lower alkoxy substituted by halogen, cyano, amino, mono or di-lower alkyl amino, C(O)-lower alkyl, aryl or heteroaryl;
R$^2$ is hydrogen or halogen;
R$^3$ is —(CH$_2$)$_p$-heterocyclyl optionally substituted by one or two substituents R$^4$; or is
lower alkyl,
lower alkoxy,
—(CH$_2$)$_p$—O-lower alkyl,
—(CH$_2$)$_p$—CN,
—O—(CH$_2$)$_p$—CN,
—(CH$_2$)$_p$-heteroaryl,
—(CH$_2$)$_p$—C(O)-heteroaryl,
—O—(CH$_2$)$_p$-heterocyclyl,
—(CH$_2$)$_p$-aryl optionally substituted by lower alkoxy or halogen,
—(CH$_2$)$_p$—O-aryl optionally substituted by lower alkyl,
—(CH$_2$)$_p$—NR'-heterocyclyl optionally substituted by lower alkyl,
—CH$_2$)$_p$—NR'R",
—CH$_2$)$_p$—NR'—CH$_2$)$_{p'}$—NR'R",
—CH$_2$)$_p$—NR'—CH$_2$)$_{p'}$—CN,
—CH$_2$)$_p$—C(O)—NR'R" or
—O—(CH$_2$)$_p$—NR'R";
R$^4$ is hydroxy, lower alkyl, —(CH$_2$)$_p$—OH, —(CH$_2$)$_p$—NR'R", —NR'—C(O)-lower alkyl, —(CH$_2$)$_p$—CN, —S(O)$_2$-lower alkyl, —NR'—S(O)$_2$-lower alkyl, —S(O)$_2$—NR'R", —C(O)-lower alkyl, —C(O)-lower cycloalkyl wherein the cycloalkyl is optionally substituted by lower alkyl, —C(O)—NR'R", heterocyclyl which is optionally substituted by =O, heteroaryl which is optionally substituted by alkoxy or cyano, aryl which is optionally substituted by alkoxy or cyano, or is 2-oxa-5-aza-bicyclo[2.2.1]hept-5-yl;
R' and R" are each independently hydrogen, lower alkyl or —(CH$_2$)$_p$—OH,
n is 1 or 2; wherein when n is 2, each R$^1$ is the same or different;
o is 1 or 2; wherein when o is 2, each R$^2$ is the same or different;
p and p' are each independently 0, 1, 2, 3 or 4;
or a pharmaceutically active salt, racemic mixture, enantiomer, optical isomer or tautomeric form thereof.

2. The compound of claim 1, wherein Ar is phenyl.
3. The compound of claim 2, wherein R$^3$ is unsubstituted —(CH$_2$)$_p$-heterocyclyl.
4. The compound of claim 3, selected from the group consisting of
1-{(3SR,4RS)-3-(3,4-dichloro-phenyl)-4-[(3-fluoro-4-trifluoromethyl-benzyl)-methyl-amino]-pyrrolidin-1-yl}-5-morpholin-4-yl-pentan-1-one;
1-{(3SR,4RS)-3-(3,4-dichloro-phenyl)-4-[methyl-(4-trifluoromethyl-benzyl)-amino]-pyrrolidin-1-yl}-morpholin-4-yl-pentan-1-one;
1-{(3SR,4RS)-3-(3,4-dichloro-phenyl)-4-[(3-fluoro-4-trifluoromethyl-benzyl)-methyl-amino]-pyrrolidin-1-yl}-5-piperazin-1-yl-pentan-1-one;
1-{(3SR,4RS)-3-(3,4-dichloro-phenyl)-4-[(3-fluoro-4-trifluoromethyl-benzyl)-methyl-amino]-pyrrolidin-1-yl}-5-pyrrolidin-1-yl-pentan-1-one;
1-{(3SR,4RS)-3-(3-chloro-phenyl)-4-[(3-fluoro-4-trifluoromethyl-benzyl)-methyl-amino]-pyrrolidin-1-yl}-5-morpholin-4-yl-pentan-1-one;
1-{(3S,4R)-3-(3,4-dichloro-phenyl)-4-[(3-fluoro-4-trifluoromethyl-benzyl)-methyl-amino]-pyrrolidin-1-yl}-3-morpholin-4-yl-propan-1-one;
1-{(3SR,4RS)-3-(3,4-dichloro-phenyl)-4-[(3-fluoro-4-trifluoromethyl-benzyl)-methyl-amino]-pyrrolidin-1-yl}-2-morpholin-4-yl-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-piperazin-1-yl-ethanone; and
1-{(3S,4R)-3-(3,4-dichloro-phenyl)-4-[(3-fluoro-4-trifluoromethyl-benzyl)-methyl-amino]-pyrrolidin-1-yl}-2-(1,1-dioxo-λ$^6$-thiomorpholin-4-yl)-ethanone.

5. The compound of claim 2, wherein $R^3$ is —$(CH_2)_p$-heterocyclyl substituted by one or two substituents $R^4$.

6. The compound of claim 5, wherein $R^4$ is —$S(O)_2$-lower alkyl.

7. The compound of claim 6, selected from the group consisting of
{(3RS,4SR)-3-[(3-fluoro-4-trifluoromethyl-benzyl)-methyl-amino]-4-phenyl-pyrrolidin-1-yl}-(4-methanesulfonyl-piperazin-1-yl)-methanone;
{(3SR,4RS)-3-(4-chloro-phenyl)-4-[(3,4-dichloro-benzyl)-methyl-amino]-pyrrolidin-1-yl}-(4-methanesulfonyl-piperazin-1-yl)-methanone;
[(3RS,4SR)-(biphenyl-4-ylmethyl-methyl-amino)-4-(4-chloro-phenyl)-pyrrolidin-1-yl]-(4-methanesulfonyl-piperazin-1-yl)-methanone;
[(3RS,4SR)-3-[(4-chloro-3-fluoro-benzyl)-methyl-amino]-4-(4-chloro-phenyl)-pyrrolidin-1-yl]-(4-methanesulfonyl-piperazin-1-yl)-methanone;
{(3SR,4RS)-3-(4-chloro-phenyl)-4-[(3-fluoro-4-trifluoromethyl-benzyl)-methyl-amino]-pyrrolidin-1-yl}-(4-methanesulfonyl-piperazin-1-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-methanesulfonyl-piperazin-1-yl)-methanone;
[(3RS,4SR)-3-[(3,4-dichloro-benzyl)-methyl-amino]-4-(3,4-dichloro-phenyl)-pyrrolidin-1-yl]-(4-methanesulfonyl-piperazin-1-yl)-methanone;
[(3RS,4SR)-3-[(4-chloro-benzyl)-methyl-amino]-4-(3,4-dichloro-phenyl)-pyrrolidin-1-yl]-(4-methanesulfonyl-piperazin-1-yl)-methanone;
4-({[(3RS,4SR)-4-(3,4-dichloro-phenyl)-1-(4-methanesulfonyl-piperazine-1-carbonyl)-pyrrolidin-3-yl]-methyl-amino}-methyl)-benzonitrile; and
{(3SR,4RS)-3-(3,4-dichloro-phenyl)-4-[(3,4-difluoro-benzyl)-methyl-amino]-pyrrolidin-1-yl}-(4-methanesulfonyl-piperazin-1-yl)-methanone.

8. The compound of claim 6, selected from the group consisting of
{(3SR,4RS)-3-(3,4-dichloro-phenyl)-4-[(2,3-dihydro-benzofuran-6-ylmethyl)-methyl-amino]-pyrrolidin-1-yl}-(4-methanesulfonyl-piperazin-1-yl)-methanone;
{(3SR,4RS)-3-(3,4-dichloro-phenyl)-4-[(4-fluoro-3-methyl-benzyl)-methyl-amino]-pyrrolidin-1-yl}-(4-methanesulfonyl-piperazin-1-yl)-methanone;
{(3SR,4RS)-3-(3,4-dichloro-phenyl)-4-[(1H-indol-6-ylmethyl)-methyl-amino]-pyrrolidin-1-yl}-(4-methanesulfonyl-piperazin-1-yl)-methanone;
4-({[(3RS,4SR)-4-(3,4-dichloro-phenyl)-1-(4-methanesulfonyl-piperazine-1-carbonyl)-pyrrolidin-3-yl]-methyl-amino}-methyl)-2-fluoro-benzonitrile;
{(3SR,4RS)-3-(3,4-dichloro-phenyl)-4-[(3-fluoro-4-trifluoromethyl-benzyl)-methyl-amino]-pyrrolidin-1-yl}-((S)-4-methanesulfonyl-3-methyl-piperazin-1-yl)-methanone;
{(3SR,4RS)-3-(3,4-dichloro-phenyl)-4-[(3-fluoro-4-trifluoromethyl-benzyl)-methyl-amino]-pyrrolidin-1-yl}-((R)-4-methanesulfonyl-3-methyl-piperazin-1-yl)-methanone;
{(3SR,4RS)-3-(4-chloro-3-fluoro-phenyl)-4-[(3-fluoro-4-trifluoromethyl-benzyl)-methyl-amino]-pyrrolidin-1-yl}-(4-methanesulfonyl-piperazin-1-yl)-methanone;
{(3SR,4RS)-3-(4-chloro-3-fluoro-phenyl)-4-[(3-fluoro-4-trifluoromethyl-benzyl)-methyl-amino]-pyrrolidin-1-yl}-(4-methanesulfonyl-[1,4]diazepan-1-yl)-methanone;
{(3SR,4RS)-3-(3,4-dichloro-phenyl)-4-[methyl-(4-trifluoromethyl-benzyl)-amino]-pyrrolidin-1-yl}-(4-methanesulfonyl-piperazin-1-yl)-methanone; and
1-{(3SR,4RS)-3-(3,4-dichloro-phenyl)-4-[(3-fluoro-4-trifluoromethyl-benzyl)-methyl-amino]-pyrrolidin-1-yl}-2-(4-methanesulfonyl-piperazin-1-yl)-ethanone.

9. The compound of claim 5, wherein $R^4$ is lower alkyl.

10. The compound of claim 9, selected from the group consisting of
1-{(3SR,4RS)-3-(3,4-dichloro-phenyl)-4-[(3-fluoro-4-trifluoromethyl-benzyl)-methyl-amino]-pyrrolidin-1-yl}-5-(4-methyl-piperazin-1-yl)-pentan-1-one;
1-{(3SR,4RS)-3-(3,4-dichloro-phenyl)-4-[(3-fluoro-4-trifluoromethyl-benzyl)-methyl-amino]-pyrrolidin-1-yl}-2-(4-methyl-piperazin-1-yl)-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-(3,5-dimethyl-piperazin-1-yl)-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-((S)-3-methyl-piperazin-1-yl)-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-((R)-3-methyl-piperazin-1-yl)-ethanone; and
1-{(3SR,4RS)-3-(3,4-dichloro-phenyl)-4-[(3-fluoro-4-trifluoromethyl-benzyl)-methyl-amino]-pyrrolidin-1-yl}-2-(2,6-dimethyl-morpholin-4-yl)-ethanone.

11. The compound of claim 5, wherein $R^4$ is —$S(O)_2$—NR'R".

12. The compound of claim 11, selected from the group consisting of
4-{(3SR,4RS)-3-(3,4-dichloro-phenyl)-4-[(3-fluoro-4-trifluoromethyl-benzyl)-methyl-amino]-pyrrolidine-1-carbonyl}-piperazine-1-sulfonic acid dimethylamide;
4-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperazine-1-sulfonic acid dimethylamide; and
4-(5-{(3SR,4RS)-3-(3,4-dichloro-phenyl)-4-[(3-fluoro-4-trifluoromethyl-benzyl)-methyl-amino]-pyrrolidin-1-yl}-5-oxo-pentyl)-piperazine-1-sulfonic acid dimethylamide.

13. The compound of claim 5, wherein $R^4$ is —NR'—$S(O)_2$-lower alkyl.

14. The compound of claim 13, selected from the group consisting of
N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-methanesulfonamide and
N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-N-methyl-methanesulfonamide.

15. The compound of claim 5, wherein $R^4$ is —C(O)-lower alkyl.

16. The compound of claim 15, selected from the group consisting of
1-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-ethanone and
2-(4-acetyl-piperazin-1-yl)-1-{(3SR,4RS)-3-(3,4-dichloro-phenyl)-4-[(3-fluoro-4-trifluoromethyl-benzyl)-methyl-amino]-pyrrolidin-1-yl}-ethanone.

17. The compound of claim 5, wherein $R^4$ is —NR'—C(O)-lower alkyl.

18. The compound of claim 17, selected from the group consisting of
- N-[1-(5-{(3SR,4RS)-3-(3,4-dichloro-phenyl)-4-[(3-fluoro-4-trifluoromethyl-benzyl)-methyl-amino]-pyrrolidin-1-yl}-5-oxo-pentyl)-piperidin-4-yl]-acetamide;
- N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-N-methyl-acetamide;
- N-[(S)-1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-pyrrolidin-3-yl]-acetamide;
- N-[(R)-1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-pyrrolidin-3-yl]-acetamide; and
- N-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-acetamide.

19. The compound of claim 5, wherein $R^4$ is —$(CH_2)_p$—NR'R"—.

20. The compound of claim 19, selected from the group consisting of
- {(3 SR,4RS)-3-(3,4-dichloro-phenyl)-4-[(3-fluoro-4-trifluoromethyl-benzyl)-methyl-amino]-pyrrolidin-1-yl}-((R)-3-dimethylamino-pyrrolidin-1-yl)-methanone;
- 1-{(3SR,4RS)-3-(3,4-dichloro-phenyl)-4-[(3-fluoro-4-trifluoromethyl-benzyl)-methyl-amino]-pyrrolidin-1-yl}-2-[4-(2-dimethylamino-ethyl)-piperazin-1-yl]-ethanone;
- {(3SR,4RS)-3-(3,4-dichloro-phenyl)-4-[(3-fluoro-4-trifluoromethyl-benzyl)-methyl-amino]-pyrrolidin-1-yl}-[4-(3-dimethylamino-propyl)-piperazin-1-yl]-methanone;
- {(3SR,4RS)-3-(3,4-dichloro-phenyl)-4-[(3-fluoro-4-trifluoromethyl-benzyl)-methyl-amino]-pyrrolidin-1-yl}-[4-(2-dimethylamino-ethyl)-piperazin-1-yl]-methanone; and
- 1-{(3SR,4RS)-3-(3,4-dichloro-phenyl)-4-[(3-fluoro-4-trifluoromethyl-benzyl)-methyl-amino]-pyrrolidin-1-yl}-2-(4-dimethylamino-piperidin-1-yl)-ethanone.

21. The compound of claim 5, wherein $R^4$ is heteroaryl optionally substituted by alkoxy or cyano.

22. The compound of claim 21, selected from the group consisting of
- {(3SR,4RS)-3-(3,4-dichloro-phenyl)-4-[(3-fluoro-4-trifluoromethyl-benzyl)-methyl-amino]-pyrrolidin-1-yl}-(4-pyrimidin-2-yl-piperazin-1-yl)-methanone;
- {(3SR,4RS)-3-(3,4-dichloro-phenyl)-4-[(3-fluoro-4-trifluoromethyl-benzyl)-methyl-amino]-pyrrolidin-1-yl}-(4-pyridin-2-yl-piperazin-1-yl)-methanone;
- {(3SR,4RS)-3-(3,4-dichloro-phenyl)-4-[(3-fluoro-4-trifluoromethyl-benzyl)-methyl-amino]-pyrrolidin-1-yl}-(4-pyridin-4-yl-piperazin-1-yl)-methanone;
- {(3SR,4RS)-3-(3,4-dichloro-phenyl)-4-[(3-fluoro-4-trifluoromethyl-benzyl)-methyl-amino]pyrrolidin-1-yl}-(2,3,5,6-tetrahydro-[1,2]bipyrazinyl-4-yl)-methanone;
- 2-(4-{(3S,4R)-3-(3,4-dichloro-phenyl)-4-[(3-fluoro-4-trifluoromethyl-benzyl)-methyl-amino]-pyrrolidine-1-carbonyl}-piperazin-1-yl)-nicotinonitrile;
- 6-{4-(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-nicotinonitrile; and
- {(3SR,4RS)-3-(3,4-dichloro-phenyl)-4-[(3-fluoro-4-trifluoromethyl-benzyl)-methyl-amino]-pyrrolidin-1-yl}-[4-(6-methoxy-pyridin-2-yl)-piperazin-1-yl]-methanone.

23. The compound of claim 5, wherein $R^4$ is aryl, optionally substituted by alkoxy or cyano.

24. The compound of claim 23, selected from the group consisting of
- {(3SR,4RS)-3-(3,4-dichloro-phenyl)-4-[(3-fluoro-4-trifluoromethyl-benzyl)-methyl-amino]-pyrrolidin-1-yl}-[4-(4-methoxy-phenyl)-piperazin-1-yl]-methanone;
- 2-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-benzonitrile; and
- 4-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-benzonitrile.

25. The compound of claim 5, wherein $R^4$ is —$(CH_2)_p$OH—.

26. The compound of claim 25, selected from the group consisting of
- {(3SR,4RS)-3-(3,4-dichloro-phenyl)-4-[(3-fluoro-4-trifluoromethyl-benzyl)-methyl-amino]-pyrrolidin-1-yl}-[4-(3-hydroxy-propyl)-piperazin-1-yl]-methanone;
- {(3SR,4RS)-3-(3,4-dichloro-phenyl)-4-[(3-fluoro-4-trifluoromethyl-benzyl)-methyl-amino]-pyrrolidin-1-yl}-[4-(2-hydroxy-ethyl)-piperazin-1-yl]-methanone;
- 1-{(3SR,4RS)-3-(3,4-dichloro-phenyl)-4-[(3-fluoro-4-trifluoromethyl-benzyl)-methyl-amino]-pyrrolidin-1-yl}-2-[4-(3-hydroxy-propyl)-piperazin-1-yl]-ethanone;
- 1-{(3SR,4RS)-3-(3,4-dichloro-phenyl)-4-[(3-fluoro-4-trifluoromethyl-benzyl)-methyl-amino]-pyrrolidin-1-yl}-2-(4-hydroxy-piperidin-1-yl)-ethanone; and
- {(3SR,4RS)-3-(3,4-dichloro-phenyl)-4-[(3-fluoro-4-trifluoromethyl-benzyl)-methyl-amino]-pyrrolidin-1-yl}-(4-hydroxy-3,4,5,6-tetrahydro-2H-[4,4']bipyridinyl-1-yl)-methanone.

27. The compound of claim 5, wherein $R^4$ is —C(O)—NR'R".

28. The compound of claim 27, wherein the compound is 4-{(3SR,4RS)-3-(3,4-dichloro-phenyl)-4-[(3-fluoro-4-trifluoromethyl-benzyl)-methyl-amino]-pyrrolidine-1-carbonyl}-piperazine-1-carboxylic acid diethylamide.

29. The compound of claim 5, wherein $R^4$ is —$(CH_2)_p$CN—.

30. The compound of claim 29, selected from the group consisting of
- 3-(4-{(3SR,4RS)-3-(3,4-dichloro-phenyl)-4-[(3-fluoro-4-trifluoromethyl-benzyl)-methyl-amino]-pyrrolidine-1-carbonyl}-piperazin-1-yl)-propionitrile;
- 3-[4-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperazin-1-yl]-propionitrile; and
- 1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidine-4-carbonitrile.

31. The compound of claim 5, wherein $R^4$ is heterocyclyl, optionally substituted by =O.

32. The compound of claim 31, selected from the group consisting of
- 4-[1-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-piperidin-4-yl]-morpholin-3-one and
- 1'-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-[1,4']bipiperidinyl-2-one.

33. The compound of claim 5, wherein $R^4$ is 2-oxa-5-aza-bicyclo[2.2.1]hept-5-yl.

34. The compound of claim 33, wherein the compound is 1-{(3SR,4RS)-3-(3,4-dichloro-phenyl)-4-[(3-fluoro-4-trifluoromethyl-benzyl)-methyl-amino]-pyrrolidin-1-yl}-2-(1S,4R)-2-oxa-5-aza-bicyclo[2.2.1]hept-5-yl-ethanone.

35. The compound of claim 5, wherein $R^4$ is —C(O)-lower cycloalkyl, substituted by lower alkyl.

36. The compound of claim 35, wherein the compound is (3 SR,4RS)-3-(3,4-dichloro-phenyl)-4-[(3-fluoro-4-trifluoromethyl-benzyl)-methyl-amino]-pyrrolidin-1-yl}-[1-(1-methyl-cyclopropanecarbonyl)-piperidin-4-yl]-methanone.

37. The compound of formula I according to claim 2, wherein $R^3$ is —$(CH_2)_p$NR'R".

38. The compound of formula I according to claim 37, selected from the group consisting of
1-{(3SR,4RS)-3-(3,4-dichloro-phenyl)-4-[(3-fluoro-4-trifluoromethyl-benzyl)-methyl-amino]pyrrolidin-1-yl}-5-methylamino-pentan-1-one and
1-{(3SR,4RS)-3-(3,4-dichloro-phenyl)-4-[(3-fluoro-4-trifluoromethyl-benzyl)-methyl-amino]-pyrrolidin-1-yl}-5-dimethylamino-pentan-1-one.

39. The compound of claim 2, wherein $R^3$ is —$(CH_2)_p$-heteroaryl.

40. The compound of claim 39, wherein the compound is 1-{(3SR,4RS)-3-(3,4-dichloro-phenyl)-4-[(3-fluoro-4-trifluoromethyl-benzyl)-methyl-amino]-pyrrolidin-1-yl}-5-imidazol-1-yl-pentan-1-one.

41. The compound of claim 2, wherein $R^3$ is —$(CH_2)_p$—C(O)-heteroaryl.

42. The compound of claim 41, wherein the compound is 1-{(3SR,4RS)-3-(3,4-dichloro-phenyl)-4-[(3-fluoro-4-trifluoromethyl-benzyl)-methyl-amino]-pyrrolidin-1-yl}-6-pyridin-2-yl-hexane-1,6-dione.

43. The compound of claim 2, wherein $R^3$ is —$(CH_2)_p$—C(O)—NR'R".

44. The compound of claim 43, wherein the compound is 6-{(3SR,4RS)-3-(3,4-dichloro-phenyl)-4-[(3-fluoro-4-trifluoromethyl-benzyl)-methyl-amino]-pyrrolidin-1-yl}-6-oxo-hexanoic acid amide.

45. The compound of claim 2, wherein $R^3$ is —$(CH_2)_p$—O-lower alkyl.

46. The compound of claim 45, wherein the compound is 1-{(3S,4R)-3-(3,4-dichloro-phenyl)-4-[(3-fluoro-4-trifluoromethyl-benzyl)-methyl-amino]-pyrrolidin-1-yl}-5-methoxy-pentan-1-one.

47. The compound of claim 2, wherein $R^3$ is —$(CH_2)_p$—CN.

48. The compound of claim 47, wherein the compound is 6-{(3SR,4RS)-3-(3,4-dichloro-phenyl)-4-[(3-fluoro-4-trifluoromethyl-benzyl)-methyl-amino]-pyrrolidin-1-yl}-6-oxo-hexanenitrile.

49. The compound of claim 2, wherein $R^3$ is —$(CH_2)_p$—NR'—$(CH_2)_{p'}$,NR'R".

50. The compound of claim 49, selected from the group consisting of
1-{(3SR,4RS)-3-(3,4-dichloro-phenyl)-4-[(3-fluoro-4-trifluoromethyl-benzyl)-methyl-amino]-pyrrolidin-1-yl}-2-(2-dimethylamino-ethylamino)-ethanone;
1-{(3SR,4RS)-3-(3,4-dichloro-phenyl)-4-[(3-fluoro-4-trifluoromethyl-benzyl)-methyl-amino]-pyrrolidin-1-yl}-2-(3-dimethylamino-propylamino)-ethanone; and
1-{(3SR,4RS)-3-(3,4-dichloro-phenyl)-4-[(3-fluoro-4-trifluoromethyl-benzyl)-methyl-amino]-pyrrolidin-1-yl}-2-[(3-dimethylamino-propyl)-methyl-amino]-ethanone.

51. The compound of claim 2, wherein $R^3$ is —$(CH_2)_p$—NR'—$(CH_2)p'$-CN.

52. The compound of claim 51, wherein the compounds are 3-(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethylamino)-propionitrile and
3-[(2-{(3SR,4RS)-3-(3,4-dichloro-phenyl)-4-[(3-fluoro-4-trifluoromethyl-benzyl)-methyl-amino]-pyrrolidin-1-yl}-2-oxo-ethyl)-methyl-amino]-propionitrile.

53. A pharmaceutical composition comprising a therapeutically effective amount of a compound of formula I

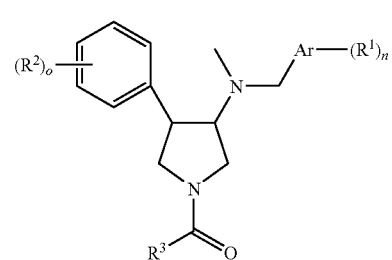

wherein
Ar is aryl;
$R^1$ is hydrogen, halogen, lower alkyl, lower alkoxy, lower alkyl substituted by halogen, lower alkoxy substituted by halogen, cyano, amino, mono or di-lower alkyl amino, C(O)-lower alkyl, aryl or heteroaryl;
$R^2$ is hydrogen or halogen;
$R^3$ is —$(CH_2)_p$-heterocyclyl optionally substituted by one or two substituents $R^4$; or is
lower alkyl,
lower alkoxy,
—$(CH_2)_p$—O-lower alkyl,
—$(CH_2)_p$—CN,
—O—$(CH_2)_p$—CN,
—$(CH_2)_p$-heteroaryl,
—$(CH_2)_p$—C(O)-heteroaryl,
—O—$(CH_2)_p$-heterocyclyl,
—$(CH_2)_p$-aryl optionally substituted by lower alkoxy or halogen,
—$(CH_2)_p$—O-aryl optionally substituted by lower alkyl,
—$(CH_2)_p$—NR'-heterocyclyl optionally substituted by lower alkyl,
—$CH_2)_p$—NR'R",
—$CH_2)_p$—NR'—$CH_2)_{p'}$—NR'R",
—$CH_2)_p$—NR'—$CH_2)_{p'}$—CN,
—$CH_2)_p$—C(O)—NR'R" or
—O—$(CH_2)_p$—NR'R";
$R^4$ is hydroxy, lower alkyl, —$(CH_2)_p$—OH, —$(CH_2)_p$—NR'R", —NR'—C(O)-lower alkyl, —$(CH_2)_p$—CN, —$S(O)_2$-lower alkyl, —NR'—$S(O)_2$-lower alkyl, —$S(O)_2$—NR'R", —C(O)-lower alkyl, —C(O)-lower cycloalkyl wherein the cycloalkyl is optionally substituted by lower alkyl, —C(O)—NR'R", heterocyclyl which is optionally substituted by =O, heteroaryl which is optionally substituted by alkoxy or cyano, aryl which is optionally substituted by alkoxy or cyano, or is 2-oxa-5-aza-bicyclo[2.2.1]hept-5-yl;
R' and R" are each independently hydrogen, lower alkyl or —$(CH_2)_p$—OH,
n is 1 or 2; wherein when n is 2, each $R^1$ is the same or different;
o is 1 or 2; wherein when o is 2, each $R^2$ is the same or different;
p and p' are each independently 0, 1, 2, 3 or 4;
or a pharmaceutically active salt, racemic mixture, enantiomer, optical isomer or tautomeric form thereof and a pharmaceutically acceptable carrier.

* * * * *